United States Patent
Stahmann et al.

(10) Patent No.: US 7,610,094 B2
(45) Date of Patent: Oct. 27, 2009

(54) SYNERGISTIC USE OF MEDICAL DEVICES FOR DETECTING MEDICAL DISORDERS

(75) Inventors: Jeffrey E. Stahmann, Ramsey, MN (US); Jesse W. Hartley, Lino Lakes, MN (US); Kent Lee, Fridley, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 762 days.

(21) Appl. No.: 10/939,586

(22) Filed: Sep. 13, 2004

(65) Prior Publication Data
US 2005/0076909 A1    Apr. 14, 2005

Related U.S. Application Data

(60) Provisional application No. 60/504,476, filed on Sep. 18, 2003.

(51) Int. Cl.
*A61N 1/08* (2006.01)
*A61B 5/08* (2006.01)

(52) U.S. Cl. .......................... 607/42; 600/529
(58) Field of Classification Search ................ 128/920; 607/42
See application file for complete search history.

(56) References Cited

U.S. PATENT DOCUMENTS

| | | | |
|---|---|---|---|
| 4,312,734 A | 1/1982 | Nichols | |
| 4,365,636 A | 12/1982 | Barker | |
| 4,390,405 A | 6/1983 | Hahn et al. | |
| 4,562,841 A | 1/1986 | Brockway et al. | |
| 4,702,253 A | 10/1987 | Nappholz et al. | |
| 4,721,110 A | 1/1988 | Lampadius | |
| 4,777,962 A | 10/1988 | Watson et al. | |
| 4,802,485 A | 2/1989 | Bowers et al. | |
| 4,807,629 A | 2/1989 | Baudino et al. | |
| 4,813,427 A | 3/1989 | Schlaefke et al. | |
| 4,827,935 A | 5/1989 | Geddes et al. | |
| 4,830,008 A | 5/1989 | Meer | |
| 4,836,219 A | 6/1989 | Hobson et al. | |
| 4,856,524 A | 8/1989 | Baker, Jr. | |

(Continued)

FOREIGN PATENT DOCUMENTS

EP    0 940 155 A    9/1999

(Continued)

OTHER PUBLICATIONS

Balaban et al., *Feasibility of Screening for Sleep Apnea Using Pacemaker Impedance Sensor*, NASPE (2001).

(Continued)

*Primary Examiner*—Carl H. Layno
*Assistant Examiner*—Tammie K. Heller
(74) *Attorney, Agent, or Firm*—Hollingsworth & Funk, LLC

(57) ABSTRACT

Methods and systems for detecting medical disorders through synergistic use of one or more medical devices are described. One or more medical devices are selected to sense one or more physiological parameters associated with a medical disorder. A presence of the medical disorder is assessed based on the sensed parameters. The medical devices used for sensing may be selected from a plurality of patient internal and/or patient-external medical devices.

20 Claims, 36 Drawing Sheets

U.S. PATENT DOCUMENTS

| | | |
|---|---|---|
| 4,875,477 A | 10/1989 | Waschke et al. |
| 4,886,064 A | 12/1989 | Strandberg |
| 4,928,688 A | 5/1990 | Mower |
| 4,958,632 A | 9/1990 | Duggan |
| 4,961,423 A | 10/1990 | Canducci |
| 4,982,738 A | 1/1991 | Griebel |
| 5,024,222 A | 6/1991 | Thacker |
| 5,036,849 A | 8/1991 | Hauck et al. |
| 5,047,930 A | 9/1991 | Martens et al. |
| 5,105,354 A | 4/1992 | Nishimura |
| 5,123,425 A | 6/1992 | Shannon, Jr. et al. |
| 5,146,918 A | 9/1992 | Kallok et al. |
| 5,174,287 A | 12/1992 | Kallok et al. |
| 5,178,156 A | 1/1993 | Takishima et al. |
| 5,183,038 A | 2/1993 | Hoffman et al. |
| 5,187,657 A | 2/1993 | Forbes |
| 5,199,424 A | 4/1993 | Sullivan et al. |
| 5,203,348 A | 4/1993 | Dahl et al. |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,243,979 A | 9/1993 | Stein et al. |
| 5,245,995 A | 9/1993 | Sullivan et al. |
| 5,259,373 A | 11/1993 | Gruenke et al. |
| 5,275,159 A | 1/1994 | Griebel |
| 5,280,791 A | 1/1994 | Lavie |
| 5,284,136 A | 2/1994 | Hauck et al. |
| 5,299,118 A | 3/1994 | Martens et al. |
| 5,301,677 A | 4/1994 | Hsung |
| 5,313,953 A | 5/1994 | Yomtov et al. |
| 5,334,222 A | 8/1994 | Salo et al. |
| 5,335,657 A | 8/1994 | Terry, Jr. et al. |
| 5,353,788 A | 10/1994 | Miles |
| 5,360,442 A | 11/1994 | Dahl et al. |
| 5,363,842 A | 11/1994 | Mishelevich et al. |
| 5,366,496 A | 11/1994 | Dahl et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,398,682 A | 3/1995 | Lynn |
| 5,404,877 A | 4/1995 | Nolan et al. |
| 5,411,031 A | 5/1995 | Yomtov |
| 5,466,245 A | 11/1995 | Heemels et al. |
| 5,482,969 A | 1/1996 | Testerman et al. |
| 5,483,969 A | 1/1996 | Testerman et al. |
| 5,485,851 A | 1/1996 | Erickson |
| 5,487,755 A | 1/1996 | Snell et al. |
| 5,517,983 A | 5/1996 | Deighan et al. |
| 5,520,176 A | 5/1996 | Cohen |
| 5,522,382 A | 6/1996 | Sullivan et al. |
| 5,522,862 A | 6/1996 | Testerman et al. |
| 5,540,727 A | 7/1996 | Tockman et al. |
| 5,545,186 A | 8/1996 | Olson et al. |
| 5,545,202 A | 8/1996 | Dahl et al. |
| 5,549,655 A | 8/1996 | Erickson |
| 5,590,648 A | 1/1997 | Mitchell et al. |
| 5,593,431 A | 1/1997 | Sheldon |
| 5,603,732 A | 2/1997 | Dahl et al. |
| 5,605,151 A | 2/1997 | Lynn |
| 5,632,281 A | 5/1997 | Rayburn |
| 5,645,570 A | 7/1997 | Corbucci |
| 5,693,000 A | 12/1997 | Crosby et al. |
| 5,697,951 A | 12/1997 | Harpstead et al. |
| 5,701,894 A | 12/1997 | Cherry et al. |
| 5,704,345 A | 1/1998 | Berthon-Jones |
| 5,713,933 A | 2/1998 | Greeninger |
| 5,715,812 A | 2/1998 | Deighan et al. |
| 5,720,771 A | 2/1998 | Snell |
| 5,738,102 A | 4/1998 | Lemelson |
| 5,792,188 A | 8/1998 | Starkweather et al. |
| 5,794,615 A | 8/1998 | Estes |
| 5,800,470 A | 9/1998 | Stein et al. |
| 5,813,836 A | 9/1998 | Starkweather et al. |
| 5,814,087 A | 9/1998 | Renirie |
| 5,826,579 A | 10/1998 | Remmers et al. |
| 5,836,987 A | 11/1998 | Baumann et al. |
| 5,839,430 A | 11/1998 | Cama |
| 5,844,680 A | 12/1998 | Sperling |
| 5,855,593 A | 1/1999 | Olson et al. |
| 5,861,011 A | 1/1999 | Stoop |
| 5,891,023 A | 4/1999 | Lynn |
| 5,902,250 A | 5/1999 | Verrier et al. |
| 5,911,218 A | 6/1999 | DiMarco |
| 5,916,243 A | 6/1999 | KenKnight et al. |
| 5,944,680 A | 8/1999 | Christopherson et al. |
| 5,957,861 A | 9/1999 | Combs et al. |
| 5,964,778 A | 10/1999 | Fugoso et al. |
| 5,970,975 A | 10/1999 | Estes et al. |
| 5,974,340 A | 10/1999 | Kadhiresan |
| 5,974,349 A | 10/1999 | Levine |
| 6,015,388 A | 1/2000 | Sackner et al. |
| 6,021,351 A | 2/2000 | Kadhiresan et al. |
| 6,026,320 A | 2/2000 | Carlson et al. |
| 6,044,297 A | 3/2000 | Sheldon et al. |
| 6,044,298 A | 3/2000 | Salo et al. |
| 6,045,513 A | 4/2000 | Stone et al. |
| 6,047,203 A | 4/2000 | Sackner et al. |
| 6,055,454 A | 4/2000 | Heemels |
| 6,059,725 A | 5/2000 | Steinschneider |
| 6,064,910 A | 5/2000 | Andersson et al. |
| 6,076,015 A | 6/2000 | Hartley et al. |
| 6,091,973 A | 7/2000 | Colla et al. |
| 6,091,986 A | 7/2000 | Keimel |
| 6,099,479 A | 8/2000 | Christopherson et al. |
| 6,105,575 A | 8/2000 | Estes et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,144,866 A | 11/2000 | Miesel et al. |
| 6,148,814 A | 11/2000 | Clemmer et al. |
| 6,155,976 A | 12/2000 | Sackner et al. |
| 6,161,042 A | 12/2000 | Hartley et al. |
| 6,168,568 B1 | 1/2001 | Gavriely |
| 6,181,961 B1 | 1/2001 | Prass |
| 6,190,326 B1 | 2/2001 | McKinnon et al. |
| 6,200,265 B1 | 3/2001 | Walsh et al. |
| 6,212,435 B1 | 4/2001 | Lattner et al. |
| 6,221,011 B1 | 4/2001 | Bardy |
| 6,236,873 B1 | 5/2001 | Holmström |
| 6,240,316 B1 | 5/2001 | Richmond et al. |
| 6,251,126 B1 | 6/2001 | Ottenhoff et al. |
| 6,258,039 B1 | 7/2001 | Okamoto et al. |
| 6,259,947 B1 | 7/2001 | Olson et al. |
| 6,261,238 B1 | 7/2001 | Gavriely |
| 6,263,244 B1 | 7/2001 | Mann et al. |
| 6,264,606 B1 | 7/2001 | Ekwall et al. |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,286,508 B1 | 9/2001 | Remmers et al. |
| 6,287,264 B1 | 9/2001 | Hoffman |
| 6,312,378 B1 | 11/2001 | Bardy |
| 6,331,536 B1 | 12/2001 | Radulovacki et al. |
| 6,336,903 B1 | 1/2002 | Bardy |
| 6,351,669 B1 | 2/2002 | Harley et al. |

| | | | | | | |
|---|---|---|---|---|---|---|
| 6,351,670 B1 | 2/2002 | Kroll | | 6,912,419 B2 | 6/2005 | Hill et al. |
| 6,353,759 B1 | 3/2002 | Harley et al. | | 6,928,324 B2 | 8/2005 | Park et al. |
| 6,357,444 B1 | 3/2002 | Parker | | 6,932,084 B2 | 8/2005 | Estes et al. |
| 6,358,203 B2 | 3/2002 | Bardy | | 6,951,539 B2 | 10/2005 | Bardy |
| 6,361,494 B1 | 3/2002 | Lindenthaler | | 6,964,641 B2 | 11/2005 | Cho et al. |
| 6,361,522 B1 | 3/2002 | Scheiner et al. | | 6,988,498 B2 | 1/2006 | Berthon-Jones et al. |
| 6,363,270 B1 | 3/2002 | Colla et al. | | 6,999,817 B2 | 2/2006 | Park et al. |
| 6,366,813 B1 | 4/2002 | DiLorenzo | | 7,025,730 B2 | 4/2006 | Cho et al. |
| 6,368,284 B1 | 4/2002 | Bardy | | 7,027,871 B2 * | 4/2006 | Burnes et al. ................. 607/60 |
| 6,368,287 B1 | 4/2002 | Hadas | | 7,062,308 B1 | 6/2006 | Jackson |
| 6,371,922 B1 | 4/2002 | Baumann et al. | | 7,065,409 B2 | 6/2006 | Mazar |
| 6,375,621 B1 | 4/2002 | Sullivan | | 7,089,936 B2 | 8/2006 | Madaus et al. |
| 6,375,623 B1 | 4/2002 | Gavriely | | 7,092,755 B2 | 8/2006 | Florio |
| 6,387,907 B1 | 5/2002 | Hendricks et al. | | 7,101,341 B2 | 9/2006 | Tsukashima et al. |
| 6,397,845 B1 | 6/2002 | Burton | | 7,117,036 B2 | 10/2006 | Florio |
| 6,398,728 B1 | 6/2002 | Bardy | | 7,127,290 B2 | 10/2006 | Girouard |
| 6,398,739 B1 | 6/2002 | Sullivan et al. | | 7,127,300 B2 | 10/2006 | Mazar et al. |
| 6,409,675 B1 | 6/2002 | Turcott | | 7,130,687 B2 | 10/2006 | Cho et al. |
| 6,409,676 B2 | 6/2002 | Ruton et al. | | 7,136,704 B2 | 11/2006 | Schulman |
| 6,411,848 B2 | 6/2002 | Kramer et al. | | 7,155,278 B2 | 12/2006 | King et al. |
| 6,411,850 B1 | 6/2002 | Kay et al. | | 7,160,252 B2 | 1/2007 | Cho |
| 6,414,183 B1 | 7/2002 | Scheiner et al. | | 7,184,817 B2 | 2/2007 | Zhu et al. |
| 6,415,183 B1 | 7/2002 | Scheiner et al. | | 7,189,204 B2 | 3/2007 | Ni et al. |
| 6,424,865 B1 | 7/2002 | Ding | | 7,204,805 B2 | 4/2007 | Dean |
| 6,431,171 B1 | 8/2002 | Burton | | 7,206,635 B2 | 4/2007 | Cho et al. |
| 6,438,407 B1 | 8/2002 | Ousdigian et al. | | 7,207,945 B2 | 4/2007 | Bardy |
| 6,438,410 B2 | 8/2002 | Hsu et al. | | 7,212,862 B2 | 5/2007 | Park et al |
| 6,440,066 B1 | 8/2002 | Bardy | | 7,225,013 B2 | 5/2007 | Geva et al. |
| 6,442,413 B1 | 8/2002 | Silver | | 7,225,021 B1 | 5/2007 | Park et al. |
| 6,447,459 B1 | 9/2002 | Larom | | 7,225,809 B1 | 6/2007 | Bowen et al. |
| 6,449,503 B1 | 9/2002 | Hsu | | 7,231,250 B2 | 6/2007 | Band et al. |
| 6,454,719 B1 | 9/2002 | Greenhut | | 7,245,971 B2 | 7/2007 | Park et al. |
| 6,459,929 B1 | 10/2002 | Hopper et al. | | 7,252,640 B2 | 8/2007 | Ni et al. |
| 6,463,326 B1 | 10/2002 | Hartley et al. | | 7,269,459 B1 | 9/2007 | Koh |
| 6,467,333 B2 | 10/2002 | Lewis et al. | | 7,302,295 B2 | 11/2007 | Stahmann et al. |
| 6,468,219 B1 | 10/2002 | Njemanze | | 7,308,311 B2 | 12/2007 | Sorensen |
| 6,480,733 B1 | 11/2002 | Turcott | | 7,314,046 B2 | 1/2008 | Schroeder et al. |
| 6,487,443 B2 | 11/2002 | Olson et al. | | 7,376,463 B2 | 5/2008 | Salo et al. |
| 6,497,658 B2 | 12/2002 | Roizen et al. | | 7,396,333 B2 | 7/2008 | Stahmann et al. |
| 6,527,729 B1 | 3/2003 | Turcott | | 7,400,928 B2 | 7/2008 | Hatlestad |
| 6,542,775 B2 | 4/2003 | Ding et al. | | 7,413,549 B1 | 8/2008 | Koh |
| 6,547,743 B2 | 4/2003 | Brydon | | 7,425,200 B2 | 9/2008 | Brockway et al. |
| 6,572,543 B1 | 6/2003 | Christopherson et al. | | 7,428,468 B2 | 9/2008 | Takemura et al. |
| 6,574,507 B1 | 6/2003 | Bonnet | | 7,435,221 B1 | 10/2008 | Bharmi et al. |
| 6,580,944 B1 | 6/2003 | Katz et al. | | 7,438,686 B2 | 10/2008 | Cho |
| 6,589,188 B1 | 7/2003 | Street et al. | | 7,440,795 B2 | 10/2008 | Poezevara |
| 6,595,928 B2 | 7/2003 | Mansy et al. | | 7,469,697 B2 | 12/2008 | Lee et al. |
| 6,597,951 B2 | 7/2003 | Kramer et al. | | 2001/0018547 A1 | 8/2001 | Mechlenburg et al. |
| 6,600,949 B1 | 7/2003 | Turcott | | 2001/0031930 A1 | 10/2001 | Roizen et al. |
| 6,606,993 B1 | 8/2003 | Wiesmann et al. | | 2002/0193685 A1 | 12/2002 | Mate et al. |
| 6,641,542 B2 | 11/2003 | Cho et al. | | 2002/0193697 A1 | 12/2002 | Cho et al. |
| 6,658,292 B2 | 12/2003 | Kroll et al. | | 2002/0193839 A1 | 12/2002 | Cho et al. |
| 6,662,032 B1 | 12/2003 | Gavish et al. | | 2003/0050538 A1 * | 3/2003 | Naghavi et al. ............. 600/300 |
| 6,679,250 B2 | 1/2004 | Walker et al. | | 2003/0055461 A1 | 3/2003 | Girouard et al. |
| 6,694,186 B2 | 2/2004 | Bardy | | 2003/0073919 A1 | 4/2003 | Hampton et al. |
| 6,723,055 B2 | 4/2004 | Hoffman | | 2003/0083241 A1 | 5/2003 | Young |
| 6,731,984 B2 | 5/2004 | Cho et al. | | 2003/0121519 A1 | 7/2003 | Estes et al. |
| 6,741,885 B1 | 5/2004 | Park et al. | | 2003/0139780 A1 | 7/2003 | Markowitz et al. |
| 6,748,252 B2 | 6/2004 | Lynn et al. | | 2003/0153953 A1 | 8/2003 | Park et al. |
| 6,752,765 B1 | 6/2004 | Jensen et al. | | 2003/0153954 A1 | 8/2003 | Park et al. |
| 6,752,766 B2 | 6/2004 | Kowallik et al. | | 2003/0153955 A1 | 8/2003 | Park et al. |
| 6,765,062 B2 | 7/2004 | Chin et al. | | 2003/0153956 A1 | 8/2003 | Park et al. |
| 6,770,022 B2 | 8/2004 | Mechlenburg et al. | | 2003/0163059 A1 | 8/2003 | Poezevara et al. |
| 6,770,029 B2 | 8/2004 | Iliff | | 2003/0171687 A1 | 9/2003 | Irie et al. |
| 6,773,404 B2 | 8/2004 | Poezevera et al. | | 2003/0178031 A1 | 9/2003 | Du Pen et al. |
| 6,786,866 B2 | 9/2004 | Odagiri et al. | | 2003/0187336 A1 | 10/2003 | Odagiri et al. |
| 6,810,287 B2 | 10/2004 | Zhu et al. | | 2003/0195571 A1 | 10/2003 | Burnes et al. |
| 6,830,548 B2 | 12/2004 | Bonnet et al. | | 2003/0199945 A1 | 10/2003 | Ciulla |
| 6,832,609 B2 | 12/2004 | Wright et al. | | 2003/0204213 A1 | 10/2003 | Jensen et al. |
| 6,881,192 B1 | 4/2005 | Park | | 2003/0209246 A1 | 11/2003 | Schroeder et al. |
| 6,895,275 B2 | 5/2005 | Markowitz et al. | | 2003/0216789 A1 | 11/2003 | Deem et al. |
| 6,904,320 B2 | 6/2005 | Park et al. | | 2004/0002742 A1 | 1/2004 | Florio |
| 6,910,481 B2 | 6/2005 | Kimmel et al. | | 2004/0030362 A1 | 2/2004 | Hill et al. |

| | | |
|---|---|---|
| 2004/0039605 A1 | 2/2004 | Bardy |
| 2004/0059240 A1 | 3/2004 | Cho et al. |
| 2004/0073093 A1* | 4/2004 | Hatlestad ............... 600/300 |
| 2004/0088027 A1 | 5/2004 | Burnes et al. |
| 2004/0102814 A1 | 5/2004 | Sorensen et al. |
| 2004/0111040 A1 | 6/2004 | Ni et al. |
| 2004/0116981 A1 | 6/2004 | Mazar |
| 2004/0122487 A1 | 6/2004 | Hatlestad et al. |
| 2004/0122488 A1 | 6/2004 | Mazar et al. |
| 2004/0128161 A1 | 7/2004 | Mazar et al. |
| 2004/0133079 A1 | 7/2004 | Mazar et al. |
| 2004/0138719 A1 | 7/2004 | Cho et al. |
| 2004/0163648 A1 | 8/2004 | Burton |
| 2004/0176695 A1 | 9/2004 | Poezevara |
| 2004/0176809 A1 | 9/2004 | Cho et al. |
| 2004/0186523 A1 | 9/2004 | Florio |
| 2004/0210154 A1 | 10/2004 | Kline |
| 2004/0210155 A1 | 10/2004 | Takemura et al. |
| 2005/0039745 A1 | 2/2005 | Stahmann et al. |
| 2005/0042589 A1 | 2/2005 | Hatlestad et al. |
| 2005/0043644 A1 | 2/2005 | Stahmann et al. |
| 2005/0043652 A1 | 2/2005 | Lovett et al. |
| 2005/0043772 A1 | 2/2005 | Stahmann et al. |
| 2005/0065447 A1 | 3/2005 | Lee et al. |
| 2005/0065572 A1 | 3/2005 | Hartley et al. |
| 2005/0085865 A1 | 4/2005 | Tehrani |
| 2005/0101841 A9* | 5/2005 | Kaylor et al. ............... 600/300 |
| 2005/0107838 A1 | 5/2005 | Lovett et al. |
| 2005/0119711 A1 | 6/2005 | Cho et al. |
| 2005/0142070 A1 | 6/2005 | Hartley et al. |
| 2005/0145246 A1 | 7/2005 | Hartley et al. |
| 2005/0159784 A1 | 7/2005 | Arceta |
| 2005/0240240 A1 | 10/2005 | Park et al. |
| 2006/0195041 A1 | 8/2006 | Lynn et al. |
| 2006/0293714 A1 | 12/2006 | Salo et al. |
| 2007/0005114 A1 | 1/2007 | Salo et al. |
| 2007/0055115 A1 | 3/2007 | Kwok et al. |
| 2007/0112388 A1 | 5/2007 | Salo |
| 2007/0149860 A1 | 6/2007 | Lynn et al. |
| 2007/0150014 A1 | 6/2007 | Kramer et al. |
| 2007/0161873 A1 | 7/2007 | Ni et al. |
| 2007/0282215 A1 | 12/2007 | Ni et al. |
| 2008/0045813 A1 | 2/2008 | Phuah et al. |
| 2009/0007918 A1 | 1/2009 | Darkin et al. |

FOREIGN PATENT DOCUMENTS

| | | |
|---|---|---|
| EP | 1 151 718 A | 11/2001 |
| EP | 1162125 | 12/2001 |
| EP | 1172125 | 1/2002 |
| WO | WO8402080 | 7/1984 |
| WO | WO9203983 | 3/1992 |
| WO | 99/04841 | 4/1999 |
| WO | WO 00/01438 A | 1/2000 |
| WO | 0017615 | 3/2000 |
| WO | WO 00/17615 | 3/2000 |
| WO | 02/087696 | 11/2002 |
| WO | WO03075744 | 9/2003 |
| WO | WO2004062485 | 7/2004 |
| WO | WO2005028029 | 3/2005 |

OTHER PUBLICATIONS

Bradley et al., Pathophysiologic and Therapeutic Implications of Sleep Apnea in Congestive Heart Failure, 3 J. Cardiac Failure 223-240 (1996). Abstract only.

Bradley et al., Sleep Apnea and Heart Failure, Park I: Obstructive Sleep Apnea, 107 Circulation 1671-1678 (2003).

Garrigue et al., Night Atrial Overdrive with DDD Pacing Results in a Significant Reduction of Sleep Apnea Episodes and QOL Improvement in Heart Failure Patients, NASPE (2001).

Garrigue et al., Benefit of Atrial Pacing in Sleep Apnea Syndrome, 346 N. Engl. J. Med. 404-412 (2002). Abstract only.

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769 (1999). Abstract only.

Jais et al., Night Atrial Overdrive with DDD Pacing: a New Therapy for Sleep Apnea Syndrome, NASPE (2000).

Javaheri et al., Sleep Apnea in 81 Ambulatory Male Patients with Stable Heart Failure: Types and Their Prevalences, Consequences, and Presentations, 97 Circulation 2154-2159 (1998).

Olusola et al., Nightcap: Laboratory and home-based evaluation of a portable sleep monitor, 32 Psychophysiology, 32-98 (1995). Abstract only.

Verrier et al., Sleep, dreams, and sudden death: the case for sleep as an autonomic stress test for the heart, 31 Cardiovascular Research 181-211 (1996).

Verrier et al., Sleep Related Cardiovascular Risk: New Home-Based Monitoring Technology for Improved Diagnosis and Therapy, 2 A.N.E. 158-175 (1997).

Roche et al., Screening of Obstructive Sleep Apnea Syndrome by Heart Rate Variability Analysis, 100 Circulation 1411-1455 (1999).

Shahrokh, A Mechanism of Central Sleep Apnea in Patients With Heart Failure, 341 N. Engl. J. Med. 949-954 (1999). Abstract only.

Vanninen et al., Cardiac Sympathovagal Balance During Sleep Apnea Episodes, 16 Clin. Physiol. 209-216 (1996). Abstract only.

Waldemark et al., Detection of Apnea using Short Window FFT Technique and Artificial Neural Network, 3390 SPIE International Society for Optical Engineering 122-133 (1998).

Young et al., The Occurrence of Sleep-Disordered Breathing Among Middle Aged Adults, N. Engl. J. Med. 1230-1235 (1993). Abstract only.

Aircraft Noise and Sleep Disturbance final report http /www.caa.co.uk/docs/33/ERCD%208008.

Bradley et al, Cardiac Output Response To Continuous Positive Airway Pressure In Congestive Heart Failure, 145 Am. Rev. Respir. Dis. 377-382 (1992). (Abstract only).

Bradley et al., Sleep Apnea and Heart Failure. Park I: Obstructive Sleep Apnea, 107 Circulation 1671-1678 (2003).

Buda et al., Effect Of Intrathoracic Pressure On Left Ventricular Performance, 301 Engl. J. Med. 453-459 (1979). (Abstract only).

Calvin et al., Positive End-Expiratory Pressure (PEEP) Does Not Depress Left Ventricular Function In Patients With Pulmonary Edema, 124 Am. Rev. Respir. Dis. 121-128 (1981). (Abstract only).

Dark et al., Breathing Pattern Abnormalities and Arterial Oxygen Desaturation During Sleep in the Congestive Heart Failure Syndrome, Chest, 6:833-6 (Jun. 1987).

De Hoyos et al., Haemodynamic Effects Of Continuous Positive Airway Pressure In Humans With Normal And Impaired Left Ventricular Function, 88 Clin. Sci. (Lond). 173-8 (1995). (Abstract only).

Giardino et al., Respiratory Sinus Arrhythmia is Associated with the Efficiency of Pulmonary Gas Exchange in Healthy Humans, 284 Am. J. Physiol. H1585-1591 (2003).

Hanson et al., Cardiac Gated Ventilation, 2433 SPIE 303-308 (1995).

Hoffman et al., Cheyne-Stokes Respiration in Patients Recovering from Acute Cardiogenic Pulmonary Edema, Chest, 97:410-12 (1990).

Kaye et al., Acute Effects Of Continuous Positive Airway Pressure On Cardiac Sympathetic Tone In Congestive Heart Failure, 103 Circulation 2336-24338 (2001).

Mansfield, D. et al., Effects of Continuous Positive Airway Pressure on Lung Function in Patients with Chronic Obstructive Pulmonary Disease and Sleep Disordered Breathing, Respirology 365-70 (1999). Abstract only.

Mehta et al., Effects Of Continuous Positive Airway Pressure On Cardiac Volumes In Patients With Ischemic And Dilated Cardiomyopathy, 161 Am. J. Respir. Crit. Care Med. 128-134 (2000).

Naughton et al., Effects Of Continuous Positive Airway Pressure On Intrathoracic And Left Ventricular Transmural Pressure In Congestive Heart Failure, 91 Circulation 1725-1731 (1995).

Pinsky et al., Hemodynamic Effect Of Cardiac Cycle-Specific Increases In Intrathoracic Pressure, 6 J. Appl. Physiol. 604-612 (1986).

Potkin et al., *Effect of positive end-expiratory pressure on right and left ventricular function in patients with the adult respiratory distress syndrome*, 135 Am. Rev. Respir. Dis. 307-311 (1987). (Abstract only).

Reddel et al., *Analysis of Adherence to Peak Flow Monitoring When Recording of Data is Electronic*, BMJ 146-147 (2002).

Rees et al., *Paroxysmal Nocturnal Dyspnoea and Periodic Respiration*, The Lancet, Dec. 22-29, pp. 1315-1317 (1979). (Abstract only).

Scharf, *Effects Of Continuous Positive Airway Pressure On Cardiac Output In Experimental Heart Failure*, 19 Sleep S240-2 (1996). (Abstract only).

Steltner et al., *Diagnosis of Sleep Apnea by Automatic Analysis of Nasal Pressure and Forced Oscillation Impedance*. Am. Journal Respiratory Critical Care Medicine, vol. 165, pp. 940-944 (2002).

Tkacova et al., *Left Ventricular Volume in Patients with Heart Failure and Cheyne-Strokes Respiration during Sleep*, Am. Journal, Respir. Crit. Care Med., vol. 156, pp. 1549-1555 (1997).

Weber et al. *Effects of CPAP and BIPAP on stroke volume in patients with obstructive sleep apnea syndrome*. Pneumolgie Mar. 1995;49(3):233-5. Translated Abstract only.

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769, 1999.

Office Action dated Jun. 29, 2007 from co-pending U.S. Appl. No. 10/643,016, filed Aug. 18, 2003.

\* cited by examiner

Fig. 6D-2

DETECTION OF PULMONARY DISEASES/DISORDERS
Conditions and Sensors

| | Transthoracic Impedance | Blood Pressure | Blood Gas |
|---|---|---|---|
| CRM Sensors | X | X | |
| CPAP Sensors | | | |
| External Non-CPAP/CRM | X | X | X |

| Physiological Changes | Respiration Rate | Tidal Volume | Minute Ventilation | Inspiration Time | Exhalation Time | Heart Motion Morphology | DC Thoracic Impedance | Systolic Blood Pressure | Diastolic Blood Pressure | Pulse Pressure | Wedge Pressure | Contractility (dP/dt) | Blood pO2 | Blood pCO2 | Arterial / Venous pO2 |
|---|---|---|---|---|---|---|---|---|---|---|---|---|---|---|---|
| Cardiovascular | | | | | | | | | | | | | | | |
| Pulmonary Hypertension | | | | | | | | | | | | | | | |
| High Pulmonary Vascular Resistance | | | | | | | | | | | | | | | |
| Tachycardia | | | | | | | X | | | | | | | | |
| Circulatory Collapse | | | | | | | | X | X | X | X | X | | X | X |
| Pulsus Paradoxicus | | | | | | | | X | X | X | X | X | X | X | |
| Syncope | | | | | | | | X | X | D | D | | | X | |
| Hypertension | | | | | | | | X | | | | | | | |
| S3 Heart Sound | | | | | | | | | | | | | | | |
| Split S2 Heart Sound | | | | | | | | | | | | | | | |
| RV Hypertrophy | | | | | | | | | | | | | | | |
| Systolic Murmur | | | | | | | | | | | | | | | |
| General Systemic | | | | | | | | | | | | | | | |
| Fever | | | | | | | | | | | | | | | |
| Weight Loss | | | | | | | | | | | | | | | |
| Weight Gain | | | | | | | | | | | | | | | |
| Night Sweats | | | | | | | | | | | | | | | |
| Peripheral Edema | | | | | | | | | | | | | | | |
| High Hemoglobin | | | | | | | | | | | | | | | |
| Fatigue | | | X | | | | | | | | | | | | |
| Joint Pain | | | X | | | | | | | | | | | | |
| Hypersomnolence | | | X | | | | | | | | | | | | |

Fig. 6D-4

DETECTION OF PULMONARY DISEASES/DISORDERS

Conditions and Sensors (601)

| | Vent Gas | Vent Flow | Vent Pres | pH | Finger | Scale | Temp | Data Base | Direct Patient Query |
|---|---|---|---|---|---|---|---|---|---|
| CRM Sensors | | | | | | | | x | |
| CPAP Sensors | x | x | x | | | | | x | |
| External Non-CPAP/CRM | x | x | x | x | x | x | x | x | x |

Physiological Changes (604) vs sensor columns: Exhaled %O2, Exhaled %CO2, Expiratory Flow, Inspiratory Flow, Expiratory Pressure, Inspiratory Pressure, Relative Pulse Pressure, Blood pH, Blood pO2, Weight, Core Temperature, Medications, History, Pain, Abnormal Breathing/Coughing, Duration of Symptoms, Falls, Other Symptoms (616-2)

Cardiovascular
- Pulmonary Hypertension
- High Pulmonary Vascular Resistance
- Tachycardia — Exhaled %O2: X; Exhaled %CO2: X
- Circulatory Collapse — Blood pH: X; Blood pO2: X
- Pulsus Paradoxicus — Blood pO2: X
- Syncope
- Hypertension
- S3 Heart Sound
- Split S2 Heart Sound
- RV Hypertrophy
- Systolic Murmur

General Systemic
- Fever — Core Temperature: X
- Weight Loss — Weight: X; Medications: X
- Weight Gain — Weight: X
- Night Sweats — Weight: X; Medications: ?
- Peripheral Edema — Pain: X; Other: D; Falls: D; Duration: D
- High Hemoglobin — Other: D; Falls: D; Duration: D
- Fatigue — Other: D; Falls: D; Duration: D
- Joint Pain — Other: D; Falls: D; Duration: D
- Hypersomnolence — Other: D; Falls: D; Duration: D

DETECTION OF PULMONARY DISEASES/DISORDERS

| Pulmonary Diseases/Disorders | | | | | | | | | | | | | | | | | | |
|---|---|---|---|---|---|---|---|---|---|---|---|---|---|---|---|---|---|---|
| | Obstructive | | Restictive | | Infectious | | | Pul Vasculature | | | Pleural | | Rhythm | | Other | | |
| Physiological Changes | Chronic Bronchitis | Emphysema | Asthma | Sarcoidosis | Pulmonary Fibrosis | Pneumoconiosis | Bronchitis | Pneumonia | Bronchiolitis | Tuberculosis | Bronchiectasis | Pulmonary Hypertension | Pulmonary Edema | Atelectasis | Pleural Effusion | Pneumothorax | Hemothorax | Apnea (See Pleural Effusion) Hypopnea (obstructive & central) | Cheyne-Stokes Periodic Breathing | Lung Cancer | ARDS |
| Dyspnea | | | | | | | | | | | | | | | | | | | | | |
| Non-specific Dyspnea | X | X | X | X | X | | | X | | X | X | X | X | | X | | | X | | | |
| Orthopnea | | X | | | | | | | | | | X | X | | | | | | | | |
| Exertional Dyspnea | X | | | X | X | | | | | | X | X | | | | | | | | | |
| Paroxysmal Noctural Dyspnea | X | | | | | | | | | | | | X | | | | | | | | |
| Blood / Respiratory Gases | | | | | | | | | | | | | | | | | | | | | |
| Cyanosis | X | X | | X | | | | | | X | X | X | X | | X | X | X | X | | | |
| Hypoxemia | X | X | | X | X | | | | | | X | X | X | | X | X | X | X | X | | |
| Hypercapnea | X | X | | X | X | | | | | | | | | | X | X | X | X | X | | |
| Low pCO2 | | | | X | | | | | | | | | | | | X | X | X | | | |
| Arterial acidosis | X | | | | | | | | | | | | | | | | | | | | |
| High Alveolar-Arterial pO2 Diff | X | | | | | | | | | | | | X | | | | | | | | |
| Respiratory Sounds | | | | | | | | | | | | | | | | | | | | | |
| Wheezing | X | | X | X | | | | X | X | X | X | | | | | | | | | | |
| Crackles | X | X | | | | X | | | | | X | | | | | | | X | | | |
| Rhonchi | X | X | | | | X | | | | | X | | | | | | | | | | |
| Fiction Rub | | | | | | | | | | | | | X | | | | | | | | |
| Attenuated Breath Sounds | X | | | | | | | | | | | | | X | X | X | X | | | | |
| Snoring | X | | | | | | | | | | | | | | | | | X | | | |

Fig. 6F-2

DETECTION OF PULMONARY DISEASES/DISORDERS

| Pulmonary Diseases/Disorders | | Physiological Changes (604) | | | | | | | | | | |
|---|---|---|---|---|---|---|---|---|---|---|---|---|
| Category | Disease | Pulmonary Function Low FEV, FVC, FEV/FVC | Low FEF | High FRC, TLC | High RV | High Lung Compliance | Slow Exhalation | Tachypnea | Shallow (Low Tidal Volume) Breathing | High Minute Ventilation | Respiratory Failure | Reduced Diffusion Capacity |
| Obstructive (COPD) | Chronic Bronchitis | X | X | | X | | | X | X | | X | X |
| Obstructive (COPD) | Emphysema | X | X | | X | | | | | | | |
| Obstructive | Asthma | | | | | | | | | | | |
| Restrictive | Sarcoidosis | | | | | | | X | X | | | X |
| Restrictive | Pulmonary Fibrosis | | | | | | | X | X | | | |
| Restrictive | Pneumoconiosis | | | | | | | | | | | |
| Restrictive | Bronchitis | | | | | | | | | | | |
| Infectious | Pneumonia | | | | | | | X | X | | | |
| Infectious | Bronchiolitis | | | | | | | | | | | |
| Infectious | Tuberculosis | | | | | | | | | | | |
| Infectious | Bronchiectasis | | | | | | | X | X | | | |
| Pul Vasculature | Pulmonary Hypertension | | | | | | | | | | | |
| Pul Vasculature | Pulmonary Edema | | | | | | | X | | | | |
| Pul Vasculature | Atelectasis | | | | | | | | | | | |
| Pul Vasculature | Pleural Effusion | | | | | | | | | | | |
| Pul Vasculature | Pulmonary Embolism | | | | | | | | | | X | |
| Pleural | Hemothorax | | | | | | | | | | | |
| Pleural | Pneumothorax | | | | | | | | | | | |
| Pleural | Apnea (obstructive & central) | | | | | | | | | | | |
| Pleural | Hypopnea (See Pleural Effusion) | | | | | | | | | | | |
| Rhythm | Cheyne-Stokes (obstructive & central) | | | | | | | | | | | |
| Rhythm | Periodic Breathing | | | | | | | | | | | |
| Other | Lung Cancer | | | | | | | | | | | |
| Other | ARDS | X | | | | | | | | | | |

620-2

Fig. 6G-1 — DETECTION OF PULMONARY DISEASES/DISORDERS

Pulmonary Diseases/Disorders (622-1) vs. Physiological Changes (604)

| Physiological Changes \ Disease | Chronic Bronchitis | Emphysema | Asthma | Sarcoidosis | Pulmonary Fibrosis | Pneumoconiosis | Bronchitis | Pneumonia | Bronchiolitis | Tuberculosis | Bronchiectasis | Pulmonary Hypertension | Pulmonary Edema | Atelectasis | Pleural Effusion | Pneumothorax | Hemothorax | Apnea (obstructive & central) | Hypopnea (see Pleural Effusion) | Cheyne-Stokes | Periodic Breathing | Lung Cancer | ARDS |
|---|---|---|---|---|---|---|---|---|---|---|---|---|---|---|---|---|---|---|---|---|---|---|---|
| Other Pulmonary | | | | | | | | | | | | | | | | | | | | | | | |
| Hemoptysis | X | X | | | | | X | X | X | X | X | X | | | | | | | | | | | |
| Cough | X | X | X | | | | X | X | X | X | X | | | | | | | | | | | | |
| Pleuritic Chest Pain | | | | | | | | X | | | | | | | | | | | | | | | |
| Local Inflammation | | | | | X | X | | | | | | | | | | | | | | | | | |
| Excess Mucous Production | X | | | | | | X | | | | | | | | | | | | | | | | |
| Chest Pain | X | | | | | | X | X | | X | | X | | X | X | | | | | | | | |
| Respiratory Infection (slight. elev. WBC) | X | X | | | | | X | X | | | | | | | | | | | | | | | |
| Pulmonary Mucus | X | X | | | | | X | X | | | | | | | | | | | | | | | |
| Overinflat. Lungs→barrel-shaped chest | | X | | | | | | | | | | | | | | | | | | | | | |
| Alveolar wall breakdown | | X | | | | | | | | | | | | | | | | | | | | | |
| Mucosal Pulmonary Edema | X | X | X | | | | | | | | | | | | | | | | | | | | |
| Ventilation-perfusion mismatch | X | X | X | | | | | | | | | | | | | | | | | | | | |
| Subepithelial Fibrosis (chronically) | | | X | | | | | | | | | | | | | | | | | | | | |
| Respiratory Muscle Fatigue | | | | | | | | | | | X | | | | | | | | | | | | |
| High small airway resistance | X | | | | | | | | | | | | | | | | | | | | | | |
| Hoarseness | | | | | | | | | | | | | | | | | | | | | | | |

Fig. 6G-2

DETECTION OF PULMONARY DISEASES/DISORDERS

Pulmonary Diseases/Disorders (604)

| Physiological Changes | Obstructive: Chronic Bronchitis | Obstructive: Emphysema | Obstructive: Asthma | COPD: Sarcoidosis | COPD: Pulmonary Fibrosis | Restrictive: Pneumoconiosis | Restrictive: Bronchitis | Restrictive: Pneumonia | Restrictive: Bronchiolitis | Infectious: Tuberculosis | Infectious: Bronchiectasis | Infectious: Pulmonary Hypertension | Pul Vasculature: Pulmonary Edema | Pul Vasculature: Atelectasis | Pul Vasculature: Pleural Effusion | Pleural: Pneumothorax | Pleural: Hemothorax | Pleural: Apnea (obstructive & central) | Pleural: Hypopnea (See Pleural Effusion) | Rhythm: Cheyne-Stokes Periodic Breathing | Other: Lung Cancer | Other: ARDS |
|---|---|---|---|---|---|---|---|---|---|---|---|---|---|---|---|---|---|---|---|---|---|---|
| Cardiovascular | | | | | | | | | | | | | | | | | | | | | | |
| Pulmonary Hypertension | X | X | | X | X | | | | | X | X | | | | | | | | | | | |
| High Pulmonary Vascular Resistance | X | X | X | X | | | | | | X | | | | | | | | | | | | |
| Tachycardia | X | X | | | | X | | | | | | | | | | | | | | | | |
| Circulatory Collapse | | | | | | | | | | | | | | | | | | | | | | X |
| Pulsus Paradoxicus | X | | X | | | | | | | | | | | | | | | | | | | |
| Syncope | | | | | | | | | | | | | | | | | | | | | | |
| Hypertension | | | | | | | X | | | | X | X | | | | | | | | | | |
| S3 Heart Sound | | | | | | | | | | | | | | | | | | | | | | |
| Split S2 Heart Sound | | | | | | | | | | | | | X | | | | | X | | | | |
| RV Hypertrophy | | | | | | | | | | | | | | | | | | | | | | |
| Systolic Murmur | | | | | | | | | | | | | | | | | | | | | | |
| General Systemic | | | | | | | | | | | | | | | | | | | | | | |
| Fever | | | | | | | X | X | X | | X | | | | | | | | | | | |
| Weight Loss | X | | X | | | | | | | X | X | | | | | | | | | | | |
| Weight Gain | | | | | | | | | | | | | | | | | | | | | | |
| Night Sweats | | | | | | | | | | X | | | | | | | | | | | | |
| Peripheral Edema | X | X | | X | | | | | | | | | | | | | | | | | | |
| High Hemoglobin | X | X | | X | | | | | | | | | | | | | X | | | | | |
| Fatigue | | | | X | | | | | | | | | | | | | | | | | | |
| Joint Pain | | | | | | | | | | | | | | | | | X | | | | | |
| Hypersomnolence | X | | | | | | | | | | | | | | | | X | | | | | |

DETECTION OF CARDIAC DISEASES/DISORDERS
Conditions and Sensors

| Physiological Changes | Blood Pressure | | | | Blood Gas | | | | Vent Gas | | pH |
|---|---|---|---|---|---|---|---|---|---|---|---|
| | Systolic Blood Pressure | Diastolic Blood Pressure | Pulse Pressure | Wedge Pressure | Contractility (dP/dt) | Blood pO2 | Blood pCO2 | Arterial / Venous pO2 | Exhaled % O2 | Exhaled % CO2 | Blood pH |
| Cardiac | | | | | | | | | | | |
| Heart Rate | | | | | D | D | D | X | X | | |
| Blood Pressure | D | D | | | D | D | | X | | | |
| Pulse Pressure | | | | | | | | | | | |
| Ectopic Beat (PVC) Density | | | | | | | | | | | |
| ST Segment Elevation | | | | | | | | | | | |
| Mitral Regurgitation | | | | | | | | | | | |
| Hypertrophy | | | | | | | | | | | |
| Chest Pain | | | | | | | | | | | |
| Stoke Volume | | | X | X | | | | | | | |
| Ventricular Contractility | X | X | X | X | | | | | | | |
| Pulse Alternans | X | X | X | X | | | | | | | |
| Syncope | X | X | X | | | | | X | | | |

Fig. 6J-1

DETECTION OF CARDIAC DISEASES/DISORDERS
Conditions and Sensors

| Physiological Changes | Blood Pressure | | | Blood Gas | | Vent Gas | | | | | |
|---|---|---|---|---|---|---|---|---|---|---|---|
| | Systolic Blood Pressure | Diastolic Blood Pressure | Pulse Pressure | Wedge Pressure | Contractility (dP/dt) | Blood pO2 | Blood pCO2 | Arterial / Venous pO2 | Exhaled % O2 | Exhaled % CO2 | pH | Blood pH |
| Pulmonary | | | | | | | | | | | | |
| Pulmonary Edema | | | | | | X | | X | X | | | X |
| Pleural Effusion | | | | | | X | | X | X | | | |
| Tidal Volume | | | | | | | | | | | | |
| Cough at Rest | | | | | | | | | | | | |
| Dyspnea | | | | | | X | | X | X | X | | X |
| Respiration Rate | | | | | | | | | | | | |
| Wheezing | | | | | | | | | | | | |
| General systemic | | | | | | | | | | | | |
| Central Apnea | | | X | X | | | | | | | | |
| Activity Level | | | | | | | | | | | | |
| O2 Saturation | | | | | | | X | | X | X | | |
| Autonomic Balance | | | | | | | | | | | | |
| Heart Rate Variability (HRV) | | | | | | | | | | | | |
| Heart Rate / Activity Profile | | | | | | | | | | | | |
| Chenye-Stokes Respiration | | | X | X | | | | | | | | |
| Weight | | | | | | | | | | | | |

Fig. 6L-1

DETECTION OF CARDIAC DISEASES/DISORDERS

| Physiological Changes | Diseases/Disorders — Rhythm | | | | Acute MI | Ischemia | CAD — Low Output | CAD — Congestion | Heart Failure | Heart Failure — Systolic | Heart Failure — Diastolic | Heart Failure | Hypertension | Hypertension | Hypertension | Other |
|---|---|---|---|---|---|---|---|---|---|---|---|---|---|---|---|---|
| | Bradycardia | Ventricular Tachy/Fib | Paroxysmal Atrial Tachy/Fib | Chronic Atrial Tachy/Fib | | | | | | | | | | | | |
| Cardiac | | | | | | | | | | | | | | | | |
| Heart Rate | X | X | X | X | X | | X | | | | | | | | | |
| Blood Pressure | X | X | X | X | X | X | X | X | | X | X | | | | | |
| Pulse Pressure | X | X | X | X | X | X | X | | | X | X | | | | | |
| Ectopic Beat (PVC) Density | X | X | X | X | X | | | | | | | | | | | |
| ST Segment Elevation | | X | X | X | X | X | | | | | | | | | | |
| Mitral Regurgitation | | X | X | X | X | | X | | | | | | | | | |
| Hypertrophy | | | | | X | | | | | | | | | | | |
| Chest Pain | | | X | | X | | | | | | | | | | | |
| Stoke Volume | | X | | | | | X | | | | | | | | | |
| Ventricular Contractility | | X | | | X | | X | | | X | | | | | | |
| Pulse Alternans | | X | | | | | X | | | | | | | | | |
| Syncope | X | X | X | X | X | | X | | | | | | | | | |

Fig. 6M

SYNERGISTIC USE OF MEDICAL DEVICES FOR DETECTING MEDICAL DISORDERS

RELATED PATENT DOCUMENTS

This application claims the benefit of Provisional Patent Application Ser. No. 60/504,476, filed on Sep. 18, 2003, to which priority is claimed pursuant to 35 U.S.C. §119(e) and which is hereby incorporated herein by reference.

FIELD OF THE INVENTION

The present invention relates generally to methods and systems for detecting medical disorders.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiration system, through the breathing mechanism, performs the function of exchanging these gases with the external environment. Together, the cardiac and respiration systems form a larger anatomical and functional unit denoted the cardiopulmonary system.

Various disorders may affect the cardiovascular, respiratory, and other physiological systems. For example, heart failure (HF) is a clinical syndrome that impacts a number of physiological processes. Heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

Pulmonary diseases or disorders may be organized into various categories, including, for example, breathing rhythm disorders, obstructive diseases, restrictive diseases, infectious diseases, pulmonary vasculature disorders, pleural cavity disorders, and others. Symptoms of pulmonary dysfunction may include symptoms such as apnea, dyspnea, changes in blood or respiratory gases, symptomatic respiratory sounds, e.g., coughing, wheezing, respiratory insufficiency, and/or general degradation of pulmonary function, among other symptoms.

Breathing rhythm disorders involve patterns of interrupted and/or disrupted breathing. Sleep apnea syndrome (SAS) and Cheyne-Stokes respiration (CSR) are examples of breathing rhythm disorders. Breathing rhythm disorders may be caused by an obstructed airway or by derangement of the signals from the brain controlling respiration. Disordered breathing rhythm during sleep is particularly prevalent and is associated with excessive daytime sleepiness, systemic hypertension, increased risk of stroke, angina, and myocardial infarction. Breathing rhythm disorders can be particularly serious for patients concurrently suffering from cardiovascular deficiencies.

Obstructive pulmonary diseases may be associated with a decrease in the total volume of exhaled airflow caused by a narrowing or blockage of the airways. Examples of obstructive pulmonary diseases include asthma, emphysema and bronchitis. Chronic obstructive pulmonary disease (COPD) refers to chronic lung diseases that result in blocked airflow in the lungs. Chronic obstructive pulmonary disease may develop over many years, typically from exposure to cigarette smoke, pollution, or other irritants. Over time, the elasticity of the lung tissue is lost, the lung's air sacs may collapse, the lungs may become distended, partially clogged with mucus, and lose the ability to expand and contract normally. As the disease progresses, breathing becomes labored, and the patient grows progressively weaker. Many people with COPD concurrently have both emphysema and chronic bronchitis.

Restrictive pulmonary diseases involve a decrease in the total volume of air that the lungs are able to hold. Often the decrease in total lung volume is due to a decrease in the elasticity of the lungs themselves, or may be caused by a limitation in the expansion of the chest wall during inhalation. Restrictive pulmonary disease can be caused by scarring from pneumonia, tuberculosis, or sarcoidosis. A decrease in lung volume may be the result of various neurologic and muscular diseases affecting the neural signals and/or muscular strength of the chest wall and lungs. Examples of neurologic and/or muscular diseases that may affect lung volume include poliomyelitis and multiple sclerosis. Lung volume deficiencies may also be related to congenital or acquired deformities of the chest.

Pulmonary dysfunctions may also involve disorders of the pleural cavity and/or pulmonary vasculature. Pulmonary vasculature disorders may include pulmonary hypertension, pulmonary edema, and pulmonary embolism. Disorders of the pleural cavity include conditions such as pleural effusion, pneumothorax, and hemothorax, for example.

Pulmonary diseases may be caused by infectious agents such as viral and/or bacterial agents. Examples of infectious pulmonary diseases include pneumonia, tuberculosis, and bronchiectasis. Non-infectious pulmonary diseases include lung cancer and adult respiratory distress syndrome (ARDS), for example.

There are a number of cardiovascular system disorders that have secondary effects with respect to other physiological systems. When functioning properly, the human heart maintains its own intrinsic rhythm, and is capable of pumping an adequate amount of blood throughout the body's circulatory system. However, some people have abnormal cardiac rhythms, referred to as cardiac arrhythmias, that cause a decrease in cardiac output.

Bradycardia is a condition that involves a heart beat that is abnormally slow, causing insufficient blood supply to the body's tissues. Tachyarrhythmia occurs when the patient's cardiac rhythm is too fast. The excessively rapid cardiac contractions result in diminished blood circulation because the heart has insufficient time to fill with blood before contracting to expel the blood. Ventricular fibrillation is a particularly dangerous form of tachyarrhythmia, and may result in death within minutes if the heart's normal rhythm is not restored.

Because of the complex interactions between the cardiovascular, pulmonary and other systems, an effective approach to monitoring, diagnosis, and treatment of various disorders is needed. The present invention fulfills these and other needs, and addresses other deficiencies of prior art implementations and techniques.

Early detection and assessment of various types of medical disorders improves the likelihood of successful treatment. The onset of some types of medical disorders is very gradual. Early detection may depend on the recognition of subtle changes in various patient conditions that may not be apparent during yearly or even monthly check-ups. The patient may compensate for decreases in physiological capacity, further obscuring detection and assessment. Methods and systems providing earlier and more accurate detection of medical disorders are desirable.

SUMMARY OF THE INVENTION

Embodiments of the invention are directed to methods and systems for detecting medical disorders through synergistic use of one or more medical devices. One embodiment involves an automated method for detecting a presence of a medical disorder. In accordance with this method one or more medical devices are selected to sense one or more conditions/parameters associated with a medical disorder. The conditions/parameters are sensed using the selected medical devices and a presence of the medical disorder is assessed based on the sensed conditions/parameters.

In accordance with various aspects of the invention, the one or more medical devices may be selected from a plurality of patient internal and patient-external medical devices. The selection may be made, for example, based on various sensing characteristics of the devices. The selection of medical devices used to sense the conditions/parameters may be altered for a variety of purposes.

In accordance with another embodiment of the invention, a system for assessing a disease presence a plurality of medical devices. Each medical device comprises a sensing system configured to sense one or more physiological conditions. A selection processor is coupled to the plurality of medical devices. The selection processor is configured to select one or more medical devices to sense one or more physiological conditions. A diagnosis processor coupled to the sensing systems of the plurality of medical devices and configured to assess a presence of a medical disorder based on the one or more physiological conditions.

The medical devices may include one or more implantable device and/or one or more patient-external devices. The system may further include a therapy unit configured to delivering patient therapy based on the assessment of the presence of the medical disorder. The therapy unit may be a component of the medical devices and may be configured, for example, to deliver cardiac electrical therapy and/or an external respiratory therapy.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
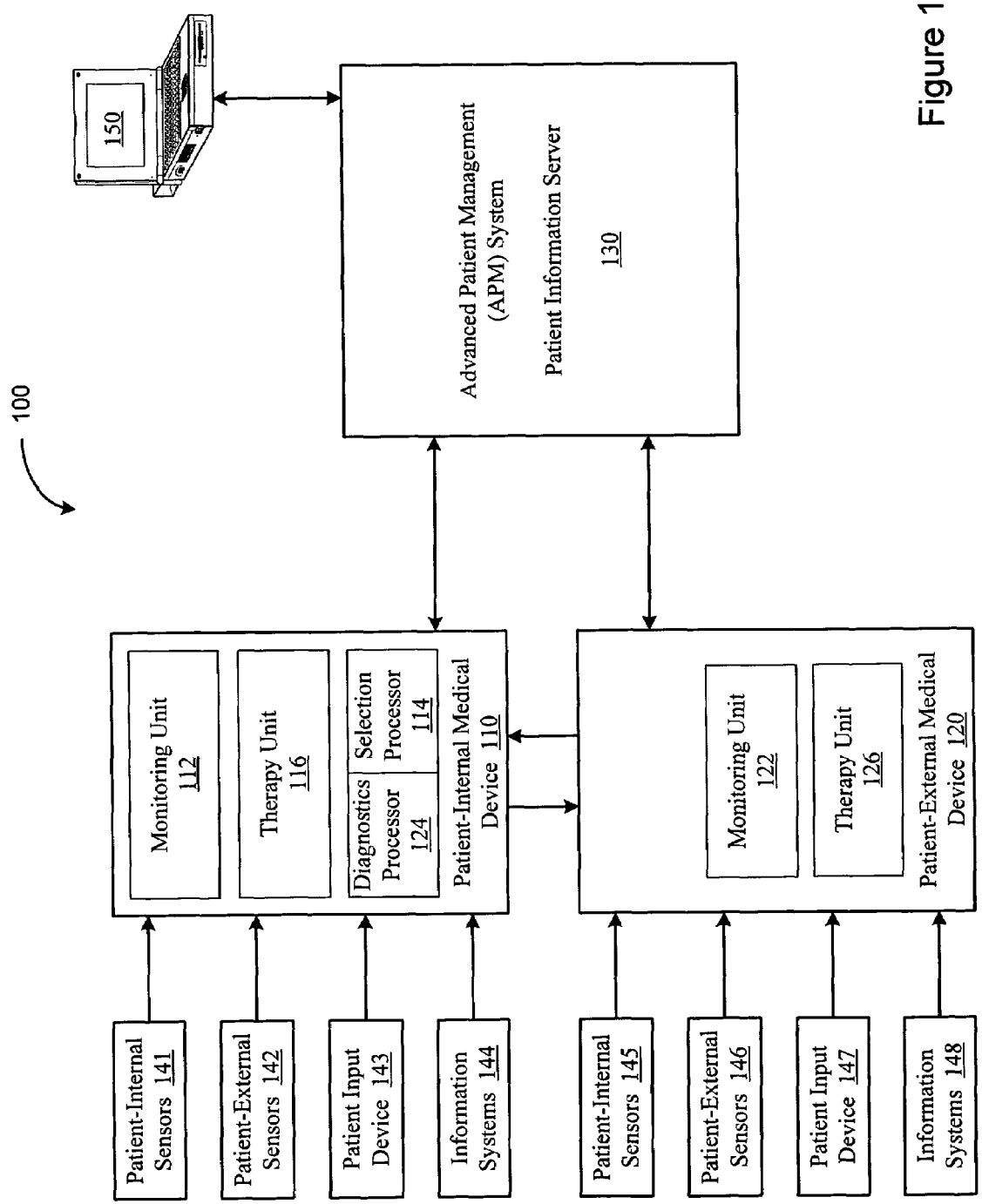
FIG. 1 is a block diagram of a medical system that may be used to implement synergistic use of medical devices for detection and/or monitoring of a medical disease/disorder in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Disorders and diseases affecting the interdependent physiological systems of the human body may be more effectively detected and assessed using a coordinated approach. Various embodiments of the invention are implemented using medical devices employing one or a number of patient-external and/or patient-internal medical devices. The medical devices may provide various medical procedures to the patient, including, for example, monitoring, diagnosis and/or therapy. The medical devices may communicate or otherwise operate in concert to provide a comprehensive patient monitoring methodology.

Embodiments of the invention are directed to synergistic use of medical devices for detecting the presence of a medical disease or disorder. Processes described herein involve automatically selecting one or more medical devices to sense one or more physiological conditions. A monitoring unit, which may be distributed among the selected medical devices, for example, collects data based on the one or more sensed conditions. A diagnostics unit detects a presence of a medical disorder based on the collected data and may assess the progression of the disorder.

FIG. 1 is a block diagram of a medical system 100 that may be used to implement coordinated detection and/or assessment of various medical disorders in accordance with embodiments of the invention. The system may additionally provide therapy to treat the detected medical disorders and/or other medical disorders of the patient. The medical system 100 may include, for example, one or more patient-internal medical devices 110 and one or more patient-external medical devices 120. Each of the patient-internal 110 and patient-external 120 medical devices may include a patient monitoring unit 112, 122 and/or a therapy unit 116, 126.

The patient-internal medical device 110 is typically a fully or partially implantable device that performs monitoring, diagnosis, and/or therapy functions. The patient-external medical device 120 performs monitoring, diagnosis and/or therapy functions external to the patient (i.e., not invasively implanted within the patient's body). The patient-external medical device 120 may be positioned on the patient, near the patient, or in any location external to the patient. It is understood that a portion of a patient-external medical device 120 may be positioned within an orifice of the body, such as the nasal cavity or mouth, yet can be considered external to the patient (e.g., mouth pieces/appliances, tubes/appliances for nostrils, or temperature sensors positioned in the ear canal).

The patient-internal and patient-external medical devices 110, 120 may be coupled to one or more sensors 141, 142, 145, 146, patient input devices 143, 147 and/or other information acquisition devices 144, 148. The sensors 141, 142, 145, 146, patient input devices 144, 147, and/or other information acquisition devices 144, 148 may be employed to detect conditions relevant to the monitoring, diagnostic, and/or therapeutic functions of the patient-internal and patient-external medical devices 110, 120.

The medical devices 110, 120 may each be coupled to one or more patient-internal sensors 141, 145 that are fully or partially implantable within the patient. The medical devices 110, 120 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 141 may be coupled to the patient-internal medical device 110 through internal leads. In one example, an internal endocardial lead system used to couple cardiac electrodes to an implantable pacemaker or other cardiac rhythm management device. One or more patient-internal sensors 141 may be equipped with transceiver circuitry to support wireless communications between the one or more patient-internal sensors 141 and the patient-internal medical device 110 and/or the patient-external medical device 120.

The patient-external sensors 142 may be coupled to the patient-internal medical device 110 and/or the patient-external medical device 120 through leads or through wireless connections. Patient-external sensors 142 preferably communicate with the patient-internal medical device 110 wirelessly. Patient-external sensors 146 may be coupled to the patient-external medical device 120 through leads or through a wireless link.

The medical devices 110, 120 may be coupled to one or more patient-input devices 143, 147. The patient-input devices are used to allow the patient to manually transfer information to the medical devices 110, 120. The patient input devices 143, 147 may be particularly useful for inputting information concerning patient perceptions, such as how well the patient feels, and information such as patient smoking, drug use, or other activities that are not automatically sensed or detected by the medical devices 110, 120.

The medical devices 110, 120 may be connected to one or more information systems 144, 148, for example, a database that stores information useful in connection with the monitoring, diagnostic, or therapy functions of the medical devices 110, 120. For example, one or more of the medical devices 110, 120 may be coupled through a network to a information system server that provides information about environmental conditions affecting the patient, e.g., the pollution index for the patient's location.

In accordance with embodiments of the invention, the system includes a selection processor 114 and a diagnostics processor 124. The selection and diagnostics processors 114, 124 may be implemented as components of the patient-internal medical device 110, the patient-external medical device 120, or as a unit separate from the patient-internal medical device 110 and the patient-external medical device 120. The selection and diagnostics processors 114, 124 may be implemented as components of an advanced patient management (APM) system 130, for example.

The selection processor 114 is configured to select one or more medical devices to sense patient conditions. The selection of the medical devices may be based, for example, on patient usage and/or on the proficiency or accuracy of the sensing system associated with a particular medical device. In one implementation, if the selection processor determines that the patient is not using the patient-external device, then the sensing function may be transferred to the patient-internal device.

The monitoring units 112, 122 of the patient-internal and patient external medical devices 110, 120 collect data based on conditions sensed or detected through the use of the sensors 141, 142, 145, 146, patient input devices 143, 146, and/or information systems 144, 148 coupled to the patient-internal and patient-external devices 110, 120. The collected data is transferred to a diagnostics unit 124 which is depicted in FIG. 1 as being a component of the patient-internal medical device 110. The diagnostics processor 124 is configured to detect the presence of the medical disease or disorder based on the collected data. The diagnostics processor 124 may also assess and/or monitor the progression, of the medical disease or disorder. Monitoring the progression of the disease may involve, for example, periodically evaluating one or more physiological changes or symptoms of the disease. Evaluating the one or more physiological changes or symptoms may be accomplished by sensing conditions associated with the symptoms or physiological changes and storing information about the sensed conditions. Monitoring disease progression may involve, for example, monitoring the severity of the disease, monitoring disease onset, progression, regression and offset, and/or monitoring other aspects of the disease.

In one embodiment, the patient-internal medical device 110 and the patient-external medical device 120 may communicate through a wireless link between the medical devices 110, 120. For example, the patient-internal and patient-external devices 110, 120 may be coupled through a short-range radio link, such as Bluetooth or a proprietary wireless link. The communications link may facilitate uni-directional or bi-directional communication between the patient-internal 110 and patient-external 120 medical devices. Data and/or control signals may be transmitted between the patient-internal 110 and patient-external 120 medical devices to coordinate the functions of the medical devices 110, 120.

In an embodiment of the invention, the patient-internal and patient-external medical devices 110, 120 may be used within the structure of an advanced patient management system. Advanced patient management systems involve a system of medical devices that are accessible through various communications technologies. For example, patient data may be downloaded from one or more of the medical devices periodically or on command, and stored at a patient information server. The physician and/or the patient may communicate with the medical devices and the patient information server, for example, to acquire patient data or to initiate, terminate or modify therapy.

In the implementation illustrated in FIG. 1, the patient-internal medical device 110 and the patient-external medical device 120 may be coupled through a wireless or wired communications link to a patient information server that is part of an advanced patient management (APM) system 130. The APM patient information server 130 may be used to download and store data collected by the patient-internal and patient-external medical devices 110, 120.

The data stored on the APM patient information server 130 may be accessible by the patient and the patient's physician through terminals 150, e.g., remote computers located in the patient's home or the physician's office. The APM patient information server 130 may be used to communicate to one or more of the patient-internal and patient-external medical devices 110, 120 to effect remote control of the monitoring, diagnosis, and/or therapy functions of the medical devices 110, 120.

In one scenario, the patient's physician may access patient data transmitted from the medical devices 110, 120 to the APM patient information server 130. After evaluation of the patient data, the patient's physician may communicate with one or more of the patient-internal or patient-external devices 110, 120 through the APM system 130 to initiate, terminate, or modify the monitoring, diagnostic, and/or therapy functions of the patient-internal and/or patient-external medical systems 110, 120. Systems and methods involving advanced patient management techniques, aspects of which may be utilized in connection with a medical disorder detection system in accordance with embodiments of the invention, are further described in U.S. Pat. Nos. 6,336,903, 6,312,378, 6,270,457, 6,398,728, and 6,440,066 which are incorporated herein by reference.

The patient-internal and patient-external medical devices 110, 120 may not communicate directly, but may communicate indirectly through the APM system 130. In this embodiment, the APM system 130 may operate as an intermediary between two or more of the medical devices 110, 120. For example, data and/or control information may be transferred from one of the medical devices 110, 120 to the APM system 130. The APM system 130 may transfer the data and/or control information to another of the medical devices 110, 120.

In one scenario, the APM system may communicate directly with the patient-internal and/or patient-external medical devices 110, 120. The advanced patient management (APM) information server 130 may be used to download and store data collected by the patient-internal and patient-external medical devices 110, 120.

Figure 2:
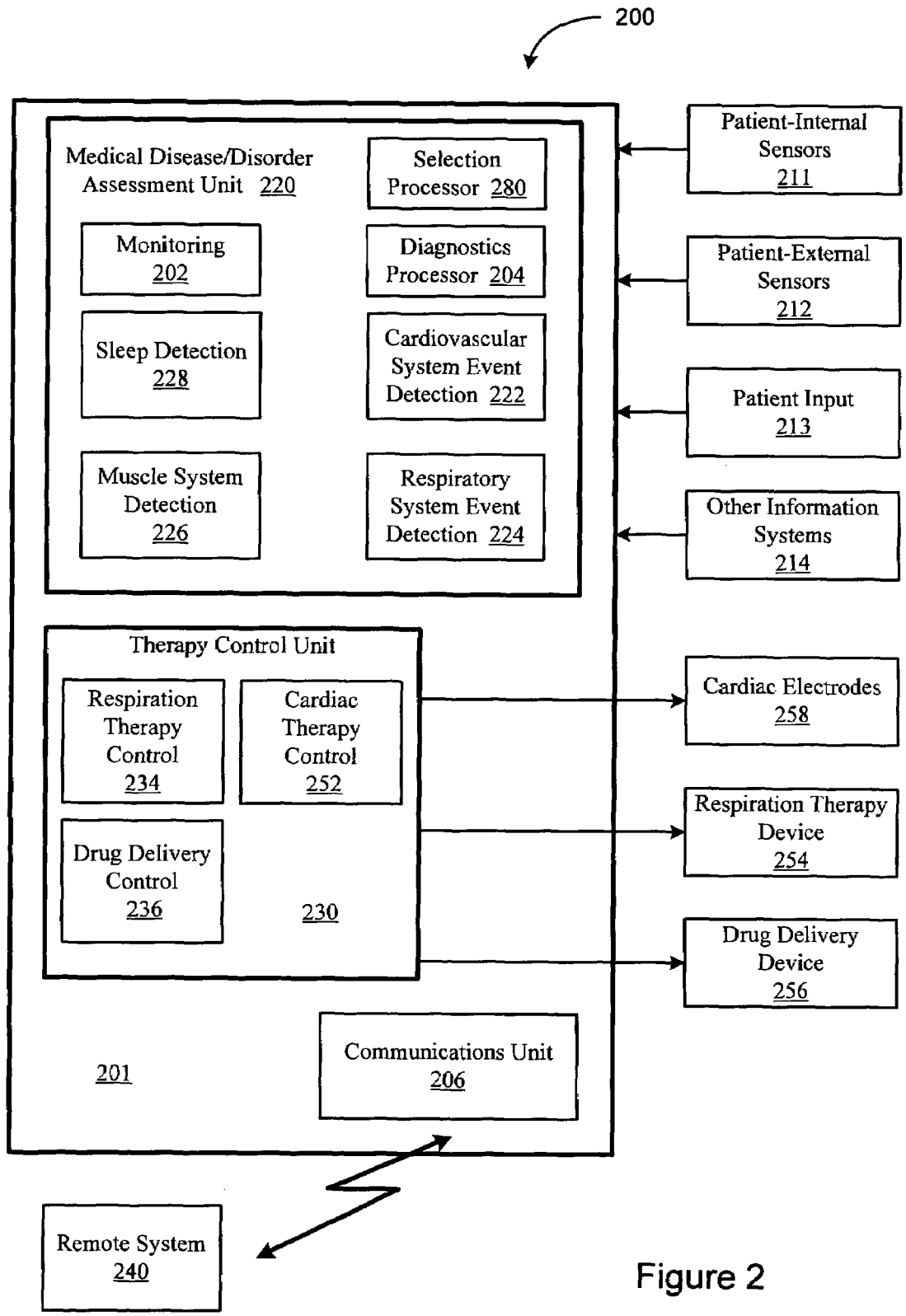
FIG. 2 is a block diagram of an implantable medical device that may be utilized in connection with a medical disease/disorder detection and/or monitoring system in accordance with embodiments of the invention.

The block diagram of FIG. 2 provides an example of a coordinated monitoring, diagnosis and/or therapeutic system 200 in accordance with embodiments of the invention. The system 200 employs a medical device 201 that may be fully or partially implantable, or may be positioned on, near, or at a remote location external to the patient.

The medical device 201 may be coupled to an array of data acquisition devices, including patient-internal sensors 211, patient-external sensors 212, patient input devices 213, and/or other information systems 214 as described above in connection with FIG. 1. The patient-internal sensors 211, patient-external sensors 212, patient input devices 213, and/or other information systems 214 are used to input a variety of conditions affecting the patient and useful for the monitoring, diagnostic, and/or therapeutic functions of the medical device 201. One or more patient conditions may also be sensed using a remote system 240. The data collected based on the conditions sensed by the remote system 240 may be transmitted to the medical device 201 through a communications unit 206.

Patient conditions may include both physiological and non-physiological conditions affecting the patient. Physiological conditions may include a broad category of conditions associated with the internal functioning of the patient's physiological systems, including the cardiovascular, respiratory, nervous, muscle and other systems. Examples of physiological conditions include blood chemistry, patient posture, patient activity, respiration quality, sleep quality, among others.

Non-physiological conditions generally encompass contextual, patient-external or background conditions. Non-physiological conditions may be broadly defined to include, for example, present environmental conditions, such as patient location, ambient temperature, humidity, air pollution index. Non-physiological conditions may also include historical/background conditions relating to the patient, including the patient's normal sleep time and the patient's medical history, for example. Methods and systems for detecting some contextual conditions, including, for example, proximity to bed detection, are described in commonly owned U.S. patent application Ser. No. 10/269,611, filed Oct. 11, 2002, which is incorporated by reference herein in its entirety.

Table 1 provides a representative set of patient conditions that may be used in connection with a coordinated approach to patient monitoring, diagnostics, and/or therapy in accordance with embodiments of the invention. Table 1 also provides illustrative sensing methods that may be employed to sense the conditions. It will be appreciated that patient conditions and detection methods other than those listed in Table 1 may be used in connection with patient monitoring, diagnosis, and/or therapy and are considered to be within the scope of the invention.

TABLE 1

| Condition Type | | Condition | Sensor type or Detection method |
|---|---|---|---|
| Physiological | Cardiovascular System | Heart rate | EGM, ECG |
| | | Heart rate variability | |
| | | QT interval | |
| | | Ventricular filling pressure | Intracardiac pressure sensor |
| | | Blood pressure | Blood pressure sensor |

TABLE 1-continued

| Condition Type | | Condition | Sensor type or Detection method |
|---|---|---|---|
| | Respiratory System | Snoring | Accelerometer Microphone |
| | | Respiration pattern (Tidal volume Minute ventilation Respiratory rate) | Transthoracic impedance sensor (AC) |
| | | Patency of upper airway | Intrathoracic impedance sensor |
| | | Pulmonary congestion | Transthoracic impedance sensor (DC) |
| | Nervous System | Sympathetic nerve activity | Muscle sympathetic nerve Activity sensor |
| | | Brain activity | EEG |
| | Blood Chemistry | CO2 saturation O2 saturation Blood alcohol content Adrenalin Brain Natriuretic Peptide (BNP) C-Reactive Protein Drug/Medication/Tobacco use | Blood analysis |
| | Muscle System | Muscle atonia | EMG |
| | | Eye movement | EOG |
| | | Patient activity | Accelerometer, MV, etc. |
| | | Limb movements | Accelerometer, EMG |
| | | Jaw movements | Accelerometer, EMG |
| | | Posture | Multi-axis accelerometer |
| Contextual | Environmental | Ambient temperature | Thermometer |
| | | Humidity | Hygrometer |
| | | Pollution | Air quality website |
| | | Time | Clock |
| | | Barometric pressure | Barometer |
| | | Ambient noise | Microphone |
| | | Ambient light | Photodetector |
| | | Altitude | Altimeter |
| | | Location | GPS, proximity sensor |
| | | Proximity to bed | Proximity to bed sensor |
| | Historical/Background | Historical sleep time | Patient input, previously detected sleep onset times |
| | | Medical history Age Recent exercise Weight Gender Body mass index Neck size Emotional state Psychological history Daytime sleepiness Patient perception of sleep quality Drug, alcohol, nicotine use | Patient input |

The medical device 201 of FIG. 2 includes a medical disease/disorder assessment unit 220 that processes data collected from one or more of the patient-internal sensors 211, patient-external sensors 212, patient input devices 213, information systems 214, and/or data collected from the remote system 240 to assess the presence of various medical diseases and/or disorders. The assessment unit 220 may include detection circuitry for detecting the occurrence of various physiological events. For example, the assessment unit 220 may include one or more of a cardiovascular system event/condition detector 222, a respiratory event/condition detector 224, a muscle system event/condition detector 226 and/or a sleep stage detector 228. Other event detection components may also be included in the assessment unit 220. The event/condition detectors 222, 224, 226, 228 may be used to detect normal and/or abnormal physiological system events or conditions. For example, the cardiovascular system event/condition detector 222 may used to detect abnormal or unusual events of the cardiovascular system such as ventricular tachycardia or fibrillation. The cardiovascular system event/condition detector 222 may also be used to detect normal cardiac beats or other events or conditions associated with the usual functioning of the heart.

The respiratory system event detector 224 may be used to detect events or conditions associated with various respiratory system disorders, such as a disordered breathing event or a pulmonary congestion condition. The respiratory system event/condition detector 224 may also be used to detect the inspiratory and expiratory phases of normal respiration cycles, for example. Various methods and systems for detecting disordered breathing are described in commonly owned U.S. patent application Ser. No. 10/309,770, filed on Dec. 4, 2002 and incorporated herein by reference.

The muscle system event/condition detector 226 may be used to detect normal or abnormal conditions, such as normal muscle atonia associated with REM sleep or abnormal muscle tone of the upper airway associated with obstructive sleep apnea events. The muscle system event/condition detector 226 may also be used, for example, to detect the level of patient activity. Patient activity information may be useful, for example, in assessing the overall activity level of the patient, or determining if the patient is asleep. Methods and systems for detecting and quantifying the effects of disordered movements occurring during sleep are described in commonly owned U.S. patent application Ser. No. 10/642,998, filed Aug. 18, 2003, which is incorporated herein by reference.

The assessment unit 220 may also include a sleep stage detector 228. The sleep stage detector 228 may analyze various inputs from the patient-internal sensors 211, patient-external sensors 212, patient input devices 213, other information systems 214 and/or events/conditions detected by the event/condition detectors 222, 224, 226, to detect sleep-related events, including, for example, sleep onset, sleep offset, sleep stages, and arousals from sleep. Methods and systems for detecting sleep, sleep stages, and/or sleep quality, aspects of which may be utilized in connection with synergistic use of medical devices for disease detection in accordance with embodiments of the invention, are described in commonly owned U.S. patent applications Ser. No. 10/309,771, filed Dec. 4, 2002, Ser. No. 10/643,006, filed Aug. 18, 2003, and Ser. No. 10/920,675, entitled "Autonomic Arousal Detection System and Method," filed Aug. 17, 2004, all of which are incorporated herein by reference.

Components of the detection unit 220 may cooperate with a monitoring unit 202. The monitoring unit 202 may incorporate a memory to store data derived from signals produced by the patient-internal sensors 211, patient-external sensors 212, patient input devices 213, and/or other information systems 214 and information derived from the event/condition detectors 222, 224, 226, 228. The stored data may be transmitted to another component of the medical device 201 or to a separate device for storage, further processing, trending, analysis and/or display, for example. In one scenario, the stored data can be downloaded to a separate device periodically or on command. The stored data may be presented to the patient's health care professional on a real-time basis, or as a long-term, e.g., month long or year long, trend of daily measurements.

The assessment unit 220 includes a selection processor 280 for selecting one or more medical devices used for sensing various conditions used for the detection and/or assessment of the medical disease/disorder. Data collected from the one or more medical devices is evaluated in a diagnostics processor 204. The diagnostics unit 204 may evaluate events or conditions detected by the selected medical devices to provide diagnostic information related to various medical disorders or diseases affecting the patient. The diagnostics processor 204 may detect a presence of a medical disease or disorder based on the data collected by the selected medical devices. The diagnostics processor 204 may also assess the onset, progression, regression, and/or offset of the medical disease or disorder. Information related to the sensed conditions and/or disease or disorder diagnostics may be stored, analyzed, trended, transmitted to a separate device, printed and/or displayed, for example. In some implementations, the information may be transmitted to a device not used to sensed physiological conditions for medical disease diagnosis, for example. In some implementations, an alert may be activated based on detection or assessment of one or more medical diseases/disorders, for example a visual or audible alert.

The medical device 201 may also include a therapy control unit 230 that controls one or more types of therapy delivered to the patient. For example, the medical device may include a cardiac therapy control unit 252 for controlling cardiac electrical stimulation delivered to the heart through one or more cardiac electrodes 258. The therapy control unit 230 may also include respiration therapy control unit 234 that provides control signals to a respiratory therapy device 254 and a drug control unit 236 that provides control signals to a drug delivery device 256. In one configuration, the medical device 201 may control the therapy delivered by a separate therapy delivery device 254, 256 by communicating directly with the separate therapy delivery device 254, 256. In another configuration, the medical device 201 may communicate with another medical device, e.g., APM system or programmer, to indirectly affect or control the therapy delivery device 254, 256. Methods and systems for providing therapy for breathing rhythm disorders, aspects of which may be implemented by embodiments of the invention, are described in commonly owned U.S. patent application Ser. No. 10/643,203, filed Aug. 18, 2003, which is incorporated herein by reference. Methods and systems for implementing therapy delivery based on cardiopulmonary status are described in commonly owned U.S. patent application Ser. No. 10/930,346, entitled "Therapy Control Based on Cardiopulmonary Status," filed Aug. 31, 2004 and incorporated herein by reference.

The medical device 201 may further include a communications unit 206 that controls communications between the medical device 201 and other devices or systems. For example, the communications unit 206 may be used to provide wireless or wired communications links between the medical device 201 and one or more of the patient-internal sensors 211, patient-external sensors 212, patient input devices 213, and information systems 214. The communications unit 206 may also facilitate communication between the medical device 201 and the therapy delivery devices 254, 256 through wireless or wired connections. The communications unit 206 may also facilitate communications between the medical device 201 and a remote device 240 such as another medical device, a remote programmer and/or an APM system as described previously in connection with FIG. 1. The wireless connections coupling the medical device 201 to various other devices and systems may utilize a variety of wireless protocols, including, for example, Bluetooth, IEEE 802.11, and/or a proprietary wireless protocol.

Figure 3:
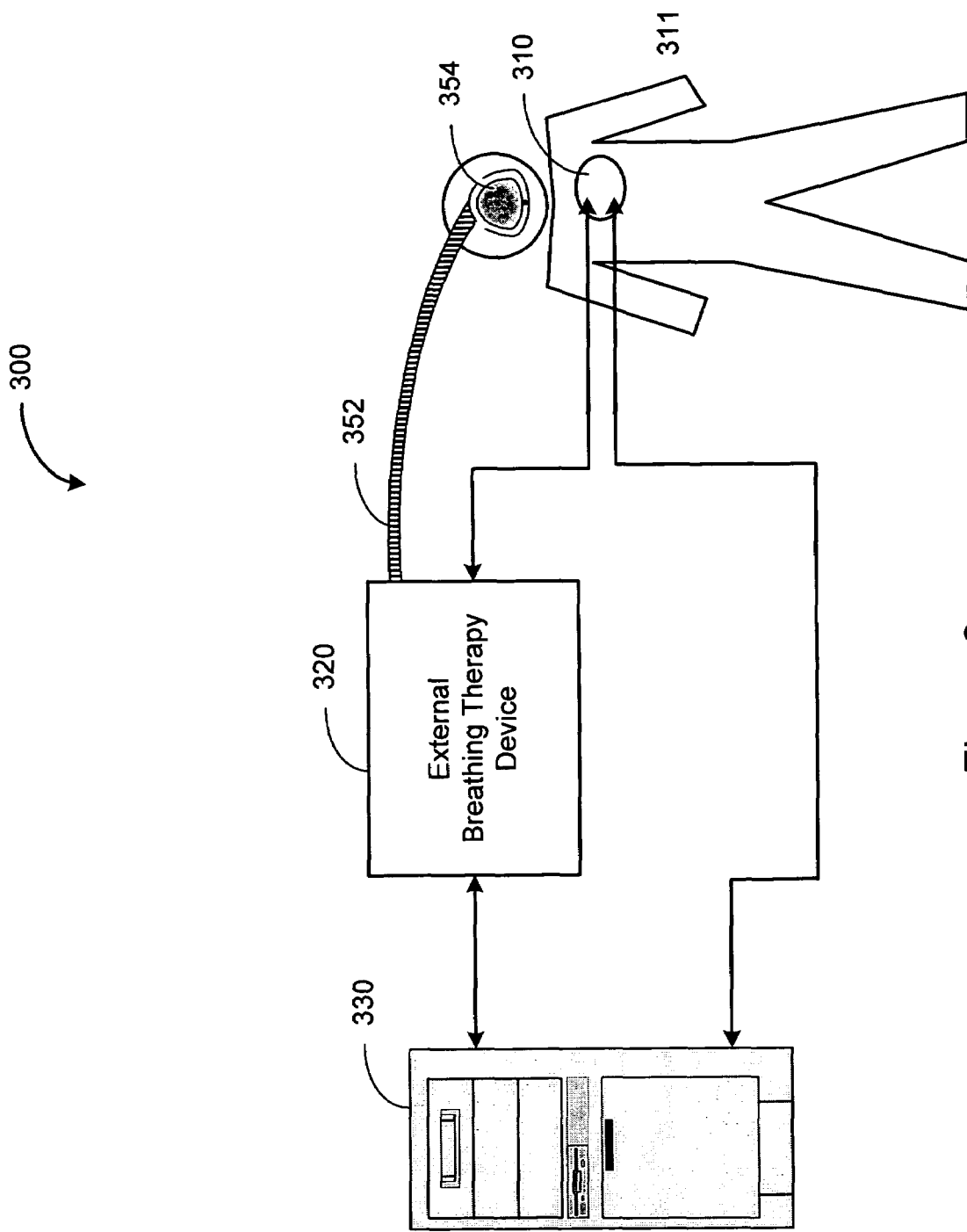
FIG. 3 illustrates a medical system including an implantable cardiac rhythm management device that cooperates with a patient-external respiration therapy device to provide medical disease/disorder detection and/or monitoring in accordance with embodiments of the invention.

According to one embodiment of the invention, illustrated in FIG. 3, a medical system 300 may include an implantable cardiac rhythm management device 310 that cooperates with a patient-external respiration therapy device 320 to provide synergistic medical disorder detection and/or assessment. In this configuration, the implantable cardiac rhythm management (CRM) device 310 operates as the patient-internal medical device described in connection with FIG. 1. The CRM device 310 may provide a first set of monitoring and/or therapeutic functions to the patient. The CRM device 310 may also include a medical disease/disorder assessment unit, including a selection processor and a diagnostics processor as described in connection with FIG. 1 above. The selection processor may determine whether to use sensors coupled to the CRM device 310 or to the CPAP device 320 to sense one or more conditions indicative of symptoms of a disease.

The CRM device 310 may be electrically coupled to the patient's heart through electrodes placed in, on, or about the heart. The cardiac electrodes may sense cardiac signals produced by the heart and/or provide therapy to one or more heart chambers. For example, the cardiac electrodes may deliver electrical stimulation to one or more heart chambers, and/or to one or multiple sites within the heart chambers. The CRM device 310 may directly control delivery of various cardiac therapies, such as cardiac pacing, defibrillation, cardioversion, cardiac resynchronization, and/or other cardiac therapies, for example. In addition, the CRM device 310 may facilitate the control of the mechanical respiration device 320. Further, the CRM device 310 may perform various monitoring and/or diagnostic functions in relation to the cardiovascular system and/or other physiological systems.

The medical system 300 may also include a mechanical respiration therapy device 320. In the example illustrated in FIG. 3, the mechanical respiration therapy device 320 comprises a positive airway pressure device that cooperates with the CRM device 310. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. Some positive airway pressure devices may also be configured to provide both positive and negative pressure, such that negative pressure is selectively used (and de-activated) when necessary, such as when treating Cheyne-Stokes breathing, for example. The term CPAP will be used herein as a generic term for any device using forms of positive airway pressure (and negative pressure when necessary), whether continuous or otherwise.

In the configuration illustrated in FIG. 3, the xPAP device 320 operates as a patient-external medical device, as discussed in connection with FIG. 1. The xPAP device 320 develops a positive air pressure that is delivered to the patient's airway through tubing 352 and mask 354 connected to the xPAP device 320. Positive airway pressure devices are often used to treat disordered breathing. In one configuration, for example, the positive airway pressure provided by the xPAP device 320 acts as a pneumatic splint keeping the patient's airway open and reducing the severity and/or number of occurrences of disordered breathing due to airway obstruction.

The xPAP device 320 may directly control the delivery of respiration therapy to the patient, and may contribute to the control of the CRM device 310. In addition, the xPAP device 320 may provide a number of monitoring and/or diagnostic functions in relation to the respiratory system and/or other physiological systems.

The CRM 310 and xPAP 320 devices may communicate directly through a wireless communications link, for example. Alternatively, or additionally, the CRM 310 and xPAP 320 devices may communicate with and/or through an APM system 330, as described above.

Although FIG. 3 illustrates a CRM device 310 used with an xPAP device 320 to provide coordinated patient monitoring, diagnosis and/or therapy, any number of patient-internal and patient-external medical devices may be included in a medical system according to embodiments of the invention. For example, a drug delivery device, such as a drug pump or controllable nebulizer, may be included in the system 300. The drug delivery device may cooperate with either or both the CRM device 310 and the xPAP device 320 and may contribute to the patient monitoring, diagnosis, and/or therapeutic functions of the medical system 300.

Figure 4:
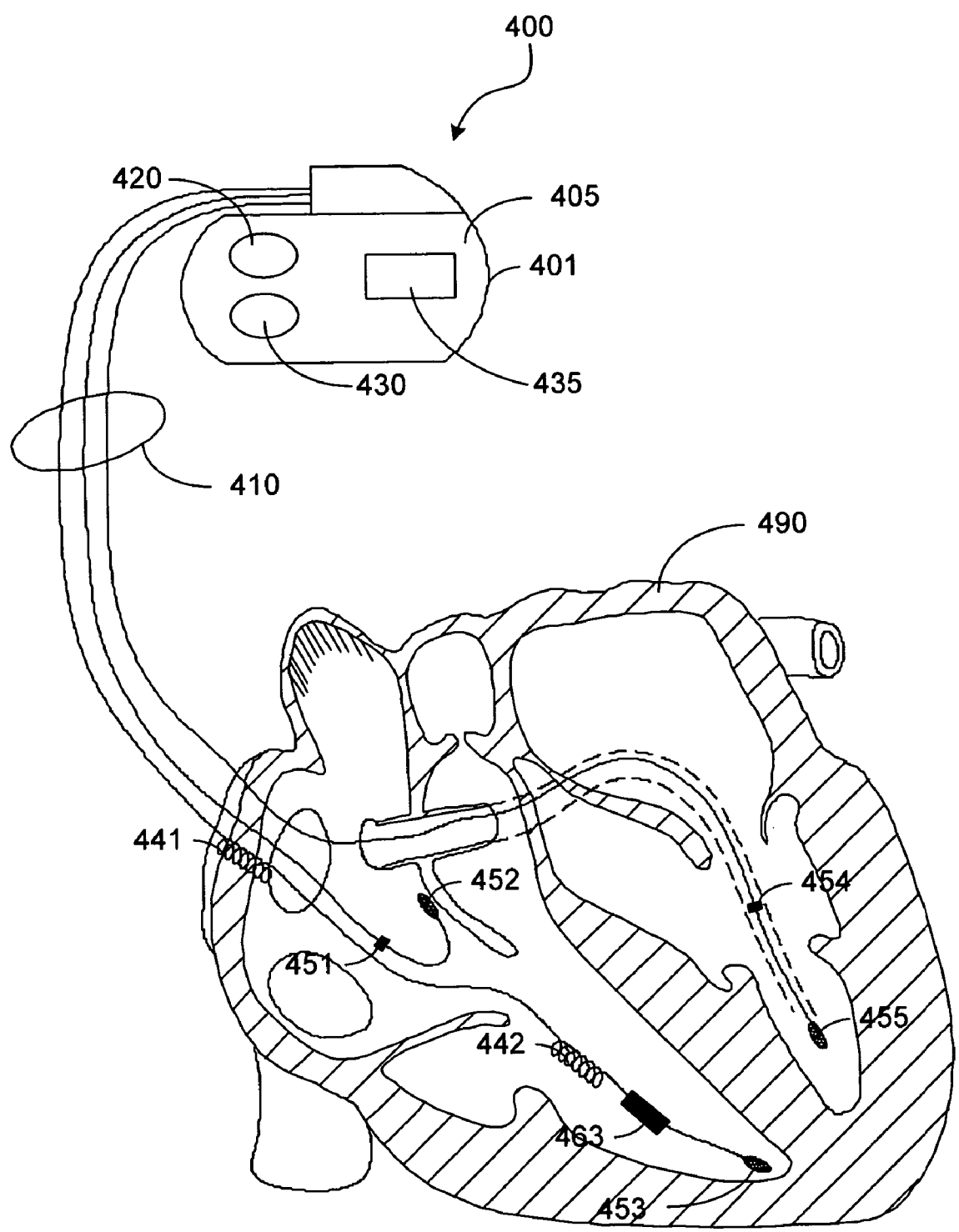
FIG. 4 is a partial view of an implantable medical device that may be used for medical disease/disorder detection and/or monitoring in accordance with embodiments of the invention.

FIG. 4 is a partial view of an implantable device that may include circuitry 435 for detecting medical disorders in accordance with embodiments of the invention. In this example, the implantable device comprises a cardiac rhythm management (CRM) device 400 including an implantable pulse generator 405 electrically and physically coupled to an intracardiac lead system 410. The circuitry for detecting medical disorders may alternatively be implemented in a variety of implantable monitoring, diagnostic, and/or therapeutic devices, such as an implantable cardiac monitoring device, an implantable drug delivery device, or an implantable neurostimulation device, for example.

Portions of the intracardiac lead system 410 are inserted into the patient's heart 490. The intracardiac lead system 410 includes one or more electrodes configured to sense electrical cardiac activity of the heart, deliver electrical stimulation to the heart, sense the patient's transthoracic impedance, and/or sense other physiological parameters, e,g, cardiac chamber pressure or temperature. Portions of the housing 401 of the pulse generator 405 may optionally serve as a can electrode.

Communications circuitry is disposed within the housing 401 for facilitating communication between the pulse generator 405 and an external communication device, such as a portable or bed-side communication station, patient-carried/worn communication station, or external programmer, for example. The communications circuitry can also facilitate unidirectional or bidirectional communication with one or more implanted, external, cutaneous, or subcutaneous physiologic or non-physiologic sensors, patient-input devices and/or information systems.

The pulse generator 405 may optionally incorporate a motion detector 420 that may be used to sense various respiration-related conditions. For example, the motion detector 420 may be optionally configured to sense snoring, activity level, and/or chest wall movements associated with respiratory effort, for example. The motion detector 420 may be implemented as an accelerometer positioned in or on the housing 401 of the pulse generator 405. If the motion sensor is implemented as an accelerometer, the motion sensor may also provide respiratory, e.g. rales, coughing, and cardiac, e.g. S1-S4 heart sounds, murmurs, and other acoustic information.

The lead system 410 of the CRM device 400 may incorporate one or more transthoracic impedance sensors that may be used to acquire the patient's respiration waveform, tidal volume, minute ventilation, and/or other respiration-related information. The transthoracic impedance sensor may include, for example, one or more intracardiac electrodes 441, 442, 451-455, 463 positioned in one or more chambers of the heart 490. The intracardiac electrodes 441, 442, 451-455, 463 may be coupled to impedance drive/sense circuitry 430 positioned within the housing of the pulse generator 405.

In one implementation, impedance drive/sense circuitry 430 generates a current that flows through the tissue between an impedance drive electrode 451 and a can electrode on the housing 401 of the pulse generator 405. The voltage at an impedance sense electrode 452 relative to the can electrode changes as the patient's transthoracic impedance changes. The voltage signal developed between the impedance sense electrode 452 and the can electrode is detected by the impedance sense circuitry 430. Other locations and/or combinations of impedance sense and drive electrodes are also possible.

The voltage signal developed at the impedance sense electrode 452 is proportional to the patient's transthoracic impedance and represents the patient's respiration waveform. The transthoracic impedance increases during respiratory inspiration and decreases during respiratory expiration. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration-expiration cycles without substantial interruptions.

The lead system 410 may include one or more cardiac pace/sense electrodes 451-455 positioned in, on, or about one or more heart chambers for sensing electrical signals from the patient's heart 490 and/or delivering pacing pulses to the heart 490. The intracardiac sense/pace electrodes 451-455, such as those illustrated in FIG. 4, may be used to sense and/or pace one or more chambers of the heart, including the left ventricle, the right ventricle, the left atrium and/or the right atrium. The lead system 410 may include one or more defibrillation electrodes 441, 442 for delivering defibrillation/cardioversion shocks to the heart.

The pulse generator 405 may include circuitry for detecting cardiac arrhythmias and/or for controlling pacing or defibrillation therapy in the form of electrical stimulation pulses or shocks delivered to the heart through the lead system 410. Circuitry for detecting medical disorders 435, including one or more of the components described in connection with FIG. 2, including monitoring circuitry 202, a sleep detector 228, muscle system event detector 226, cardiovascular system event detector 222, respiratory system event detector 224, selection processor 280, and/or diagnostics processor 204 may be housed within the pulse generator 405. The circuitry for detecting medical disorders may be coupled to various sensors, patient input devices, and/or information systems through leads or through wireless communication links.

Figure 5:
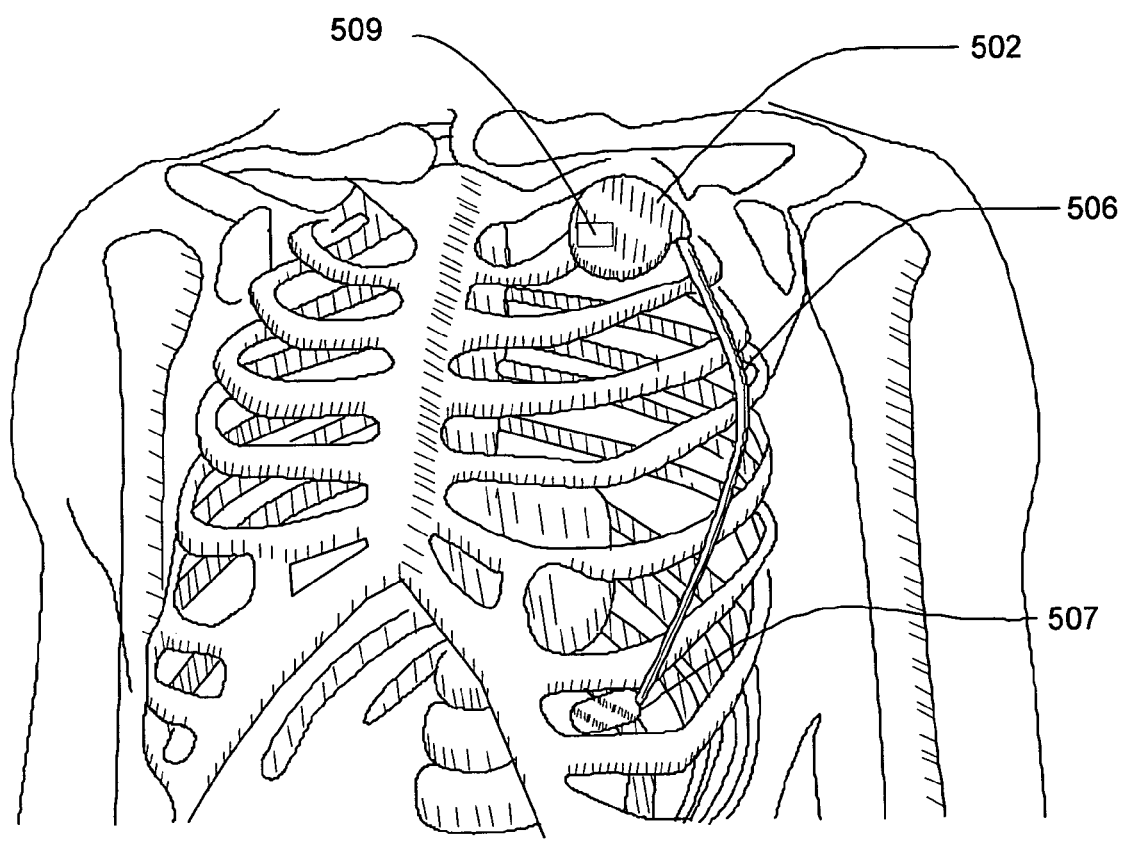
FIG. 5 is a partial view of an implantable subcutaneous medical device that may be used for medical disease/disorder detection and/or monitoring in accordance with embodiments of the invention.

FIG. 5 is a diagram illustrating an implantable transthoracic cardiac device that may be used in connection with detecting medical disorders in accordance with embodiments of the invention. The implantable device illustrated in FIG. 5 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

Circuitry for implementing a respiratory logbook system may be positioned within the primary housing of the ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In the configuration shown in FIG. 5, a subcutaneous electrode assembly 507 can be positioned under the skin in the chest region and situated distal from the housing 502. The subcutaneous and, if applicable, housing electrode(s) can be positioned about the heart at various locations and orientations, such as at various anterior and/or posterior locations relative to the heart. The subcutaneous electrode assembly 507 is coupled to circuitry within the housing 502 via a lead assembly 506. One or more conductors (e.g., coils or cables) are provided within the lead assembly 506 and electrically couple the subcutaneous electrode assembly 507 with circuitry in the housing 502. One or more sense, sense/pace or defibrillation electrodes can be situated on the elongated structure of the electrode support, the housing 502, and/or the distal electrode assembly (shown as subcutaneous electrode assembly 507 in the configuration shown in FIG. 5).

It is noted that the electrode and the lead assemblies 507, 506 can be configured to assume a variety of shapes. For example, the lead assembly 506 can have a wedge, chevron, flattened oval, or a ribbon shape, and the subcutaneous electrode assembly 507 can comprise a number of spaced electrodes, such as an array or band of electrodes. Moreover, two or more subcutaneous electrode assemblies 507 can be mounted to multiple electrode support assemblies 506 to achieve a desired spaced relationship amongst subcutaneous electrode assemblies 507.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203, 348; 5,230,337; 5,360,442; 5,366,496; 5,397,342; 5,391,200; 5,545,202; 5,603,732; and 5,916,243 and commonly owned U.S. patent applications Ser. No. 60/462,272, filed Apr. 11, 2003; Ser. No. 10/462,001, filed Jun. 13, 2003; Ser. No. 10/465,520, filed Jun. 19, 2003; Ser. No. 10/820,642, filed Apr. 8, 2004; and Ser. No. 10/821,248, filed Apr. 8, 2004, all of which are incorporated herein by reference.

The housing of the ITCS device may incorporate circuitry for detecting and/or treating various medical disorders 509, including various components illustrated in FIG. 2, such as components of the medical disease/disorder assessment unit 220 and/or components of the therapy control unit 230. components of the medical disease/disorder assessment unit 220 may be coupled to one or more sensors, patient input devices, and/or information systems as described in connection with FIG. 2.

In one implementation, the ITCS device may include an impedance sensor configured to sense the patient's transthoracic impedance. The impedance sensor may include the impedance drive/sense circuitry incorporated with the housing 502 of the ITCS device and coupled to impedance electrodes positioned on the can or at other locations of the ITCS device, such as on the subcutaneous electrode assembly 507 and/or lead assembly 506. In one configuration, the impedance drive circuitry generates a current that flows between a subcutaneous impedance drive electrode and a can electrode on the primary housing of the ITCS device. The voltage at a subcutaneous impedance sense electrode relative to the can electrode changes as the patient's transthoracic impedance changes. The voltage signal developed between the impedance sense electrode and the can electrode is sensed by the impedance drive/sense circuitry.

Communications circuitry is disposed within the housing 502 for facilitating communication between the ITCS device and an external communication device, such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors.

Figure 6A:
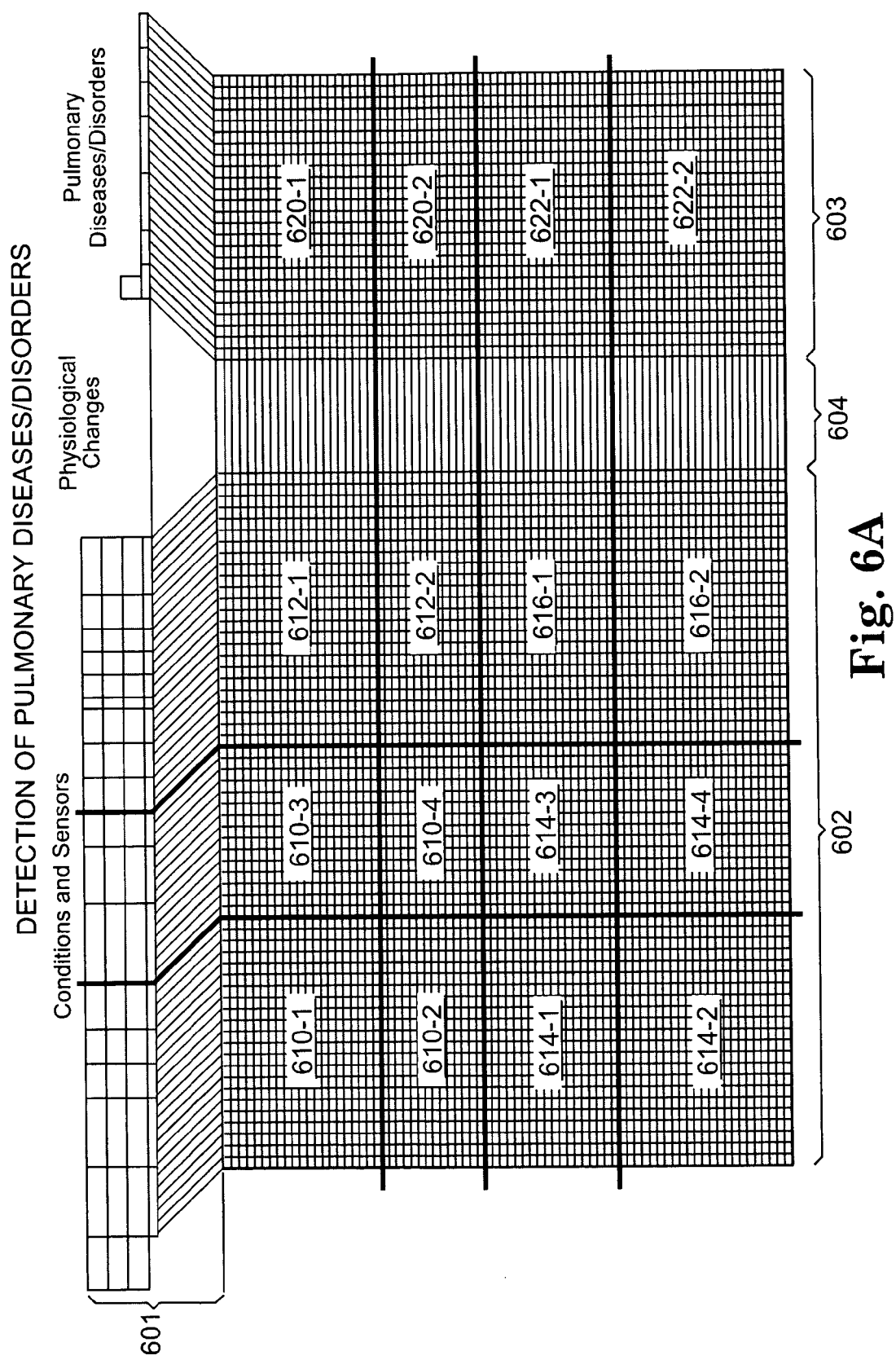
FIGS. 6A-6N depict a chart illustrating relationships between medical diseases or disorders, symptoms and/or physiological changes caused by the medical diseases or disorders, and conditions used to detect the symptoms and/or physiological changes in accordance with embodiments of the invention.

Embodiments of the invention are directed to the synergistic use of patient external and patient internal devices to detect a presence of and/or assess a variety of medical disorders, including cardiac disorders and/or pulmonary disorders. FIGS. 6A-6N list various cardiac and/or pulmonary diseases/disorders that may be detected using the approaches of the present invention.

As referenced in FIGS. 6A-6N, the term "condition," denotes an parameter that may be sensed and/or measured based on a signal generated by a sensor or other input device of the one or more medical devices. Typically, a physiological sensor generates a signal modulated by a physiological parameter. In some cases, a physiological condition may be directly measured based on the sensor signal. For example, a blood pressure measurement may directly correlate to the signal generated by a blood pressure sensor. In other cases, a condition may be derived from the sensor signal. For example, tidal volume is a respiratory system condition that may be derived from the signal generated by a transthoracic impedance sensor. In another example, heart rate is a cardiac system condition that may be derived from a cardiac electrogram sensor.

The terms "symptom" and "physiological change" refer to a manifestation of a medical disease or disorder. Symptoms and/or physiological changes may be detectable based on a sensed presence of one or more physiological conditions and/or measured values associated with the one or more sensed physiological conditions. The terms "disease" and/or "disorder" are used to refer to a medical dysfunction that is characterizable by a collection of symptoms or physiological changes.

The chart depicted in FIGS. 6A-6N illustrates relationships between various physiological changes and/or disease symptoms with medical disorders. The chart lists a representative set of medical disorders that may be evaluated in accordance with embodiments of the invention. A representative set of pulmonary medical disorders that may be evaluated includes, for example, breathing rhythm disorders (e.g., apnea, hypopnea, Cheyne-Stokes Respiration), obstructive pulmonary diseases (e.g., chronic bronchitis, emphysema, asthma), restrictive pulmonary diseases (e.g., sarcoidosis, pulmonary fibrosis, pneumoconiosis), infections pulmonary diseases (e.g., bronchitis, pneumonia, bronchiolitis, tuberculosis, and bronchiectasis), pulmonary vasculature diseases (e.g., pulmonary hypertension, pulmonary edema, pulmonary embolism, atelectasis), and diseases of the pleural cavity (e.g., pleural effusion, pneumothorax, and hemothorax).

A representative set of cardiac disorders that may be evaluated includes, for example, cardiac rhythm disorders (e.g., bradycardia, ventricular tachyarrhythmia, ventricular fibrillation, paroxymal atrial tachyarrhythmia/fibrillation, chronic atrial tachyarrhythmia/fibrillation), coronary artery disease (CAD) (e.g., acute myocardial infarction, ischemia), heart failure (e.g., low output, congestion), and hypertensive disorders (e.g., systolic hypertension, diastolic hypertension).

Each medical disease/disorder is cross-referenced with physiological changes and/or symptoms associated with the medical disorder. The physiological changes and/or symptoms are further cross referenced with conditions indicative of the physiological changes and/or symptoms. Sensors that may be used to sense the conditions indicative of the physiological changes or symptoms are also listed.

FIGS. 6A-6N reference sensors associated with a CPAP device, a CRM device, and an external non-CPAP, non-CRM device. Information available through the CPAP device may be acquired by a ventilation gas sensor, a ventilation flow sensor and/or a ventilation pressure sensor, for example. Information available through the CRM device may be acquired by a right ventricular egram, left ventricular egram, right atrial egram, left atrial egram, accelerometer, transthoracic impedance sensor, blood pressure sensor, blood gas sensor, pH sensor, and temperature sensor, for example. Information available through the external non-CPAP, non-CRM device may be acquired by any of the sensors listed in connection with the CPAP and/or CRM devices in addition to a finger sensor, scale, patient database and/or through direct patient query, for example.

The left section 602 of FIG. 6A illustrates various conditions that may be sensed using sensors of a respiratory therapy device (CPAP), a cardiac device (CRM), or an external non-CPAP, non-CRM device. The top section 601 lists various conditions that may be sensed and provides information about sensors used to sense the conditions. The center section 604 of FIG. 6A provides physiological changes and/or symptoms that may be evaluated using the conditions listed in the left section 602. The right section 603 of FIG. 6A provides pulmonary diseases/disorders. The presence of the pulmonary diseases/disorders of the right section 603 may be assessed based on the physiological changes and/or symptoms of the center section 604.

Figures 1, 6B:
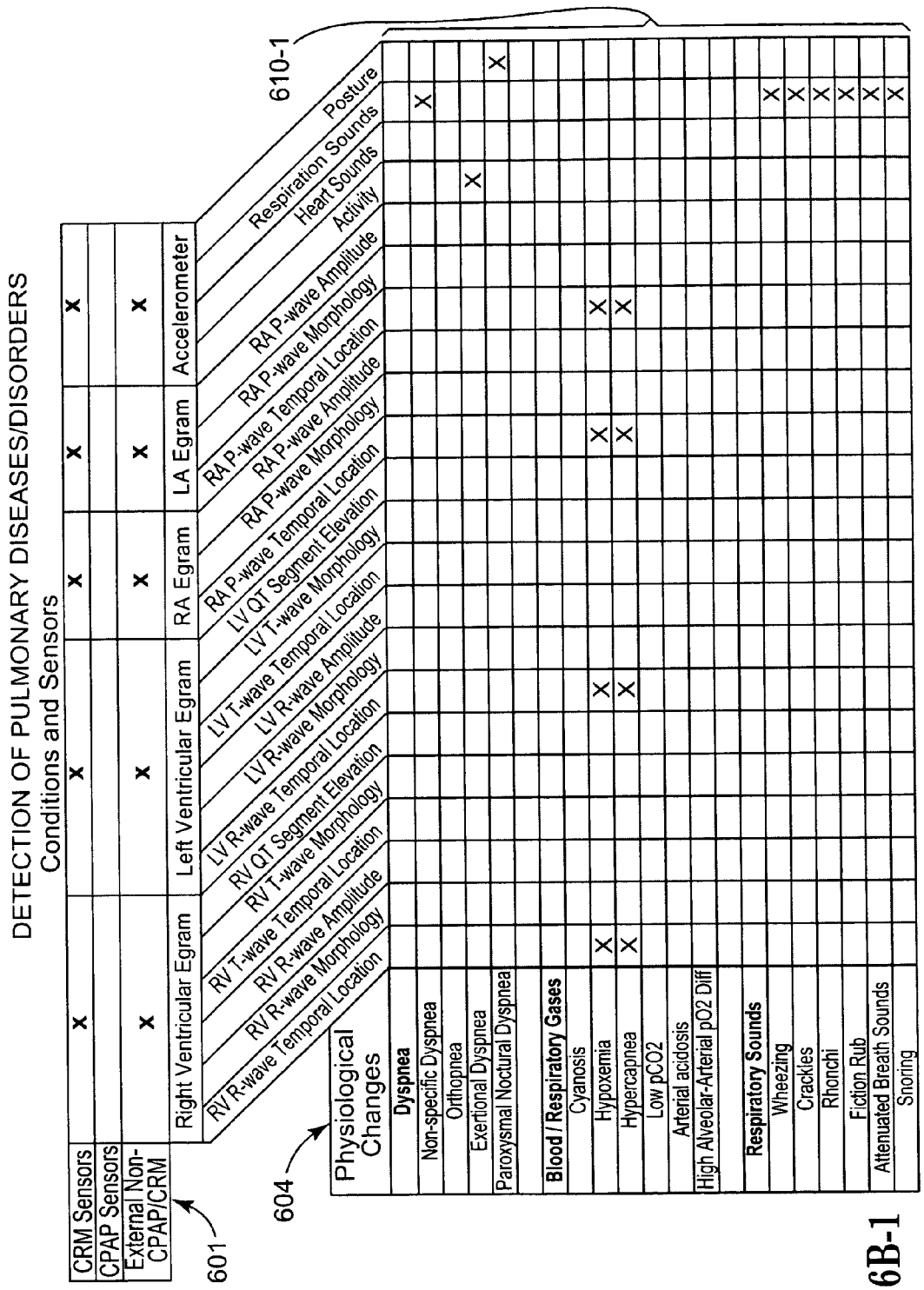
Figures 2, 6B:
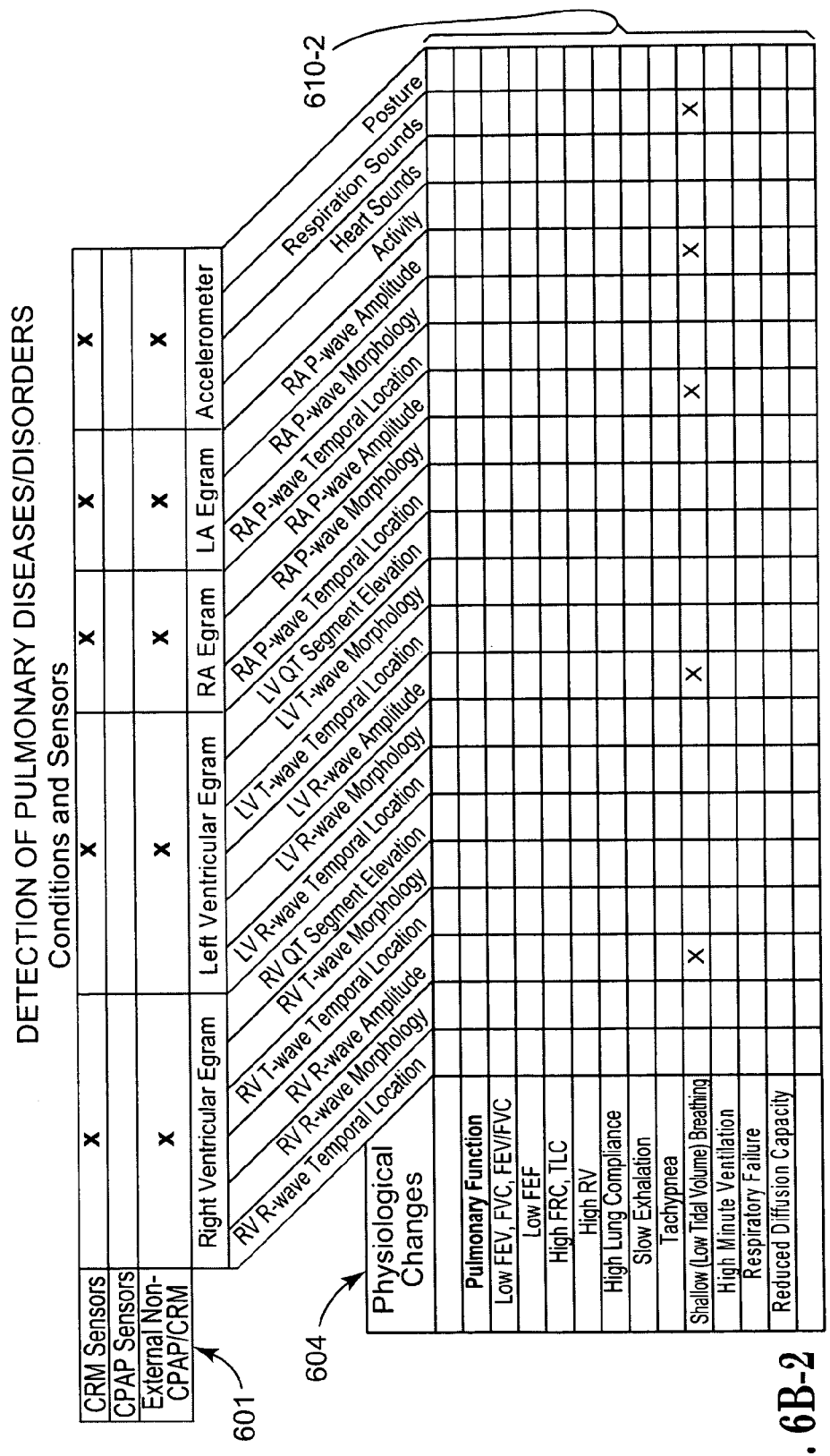
Figures 3, 6B:
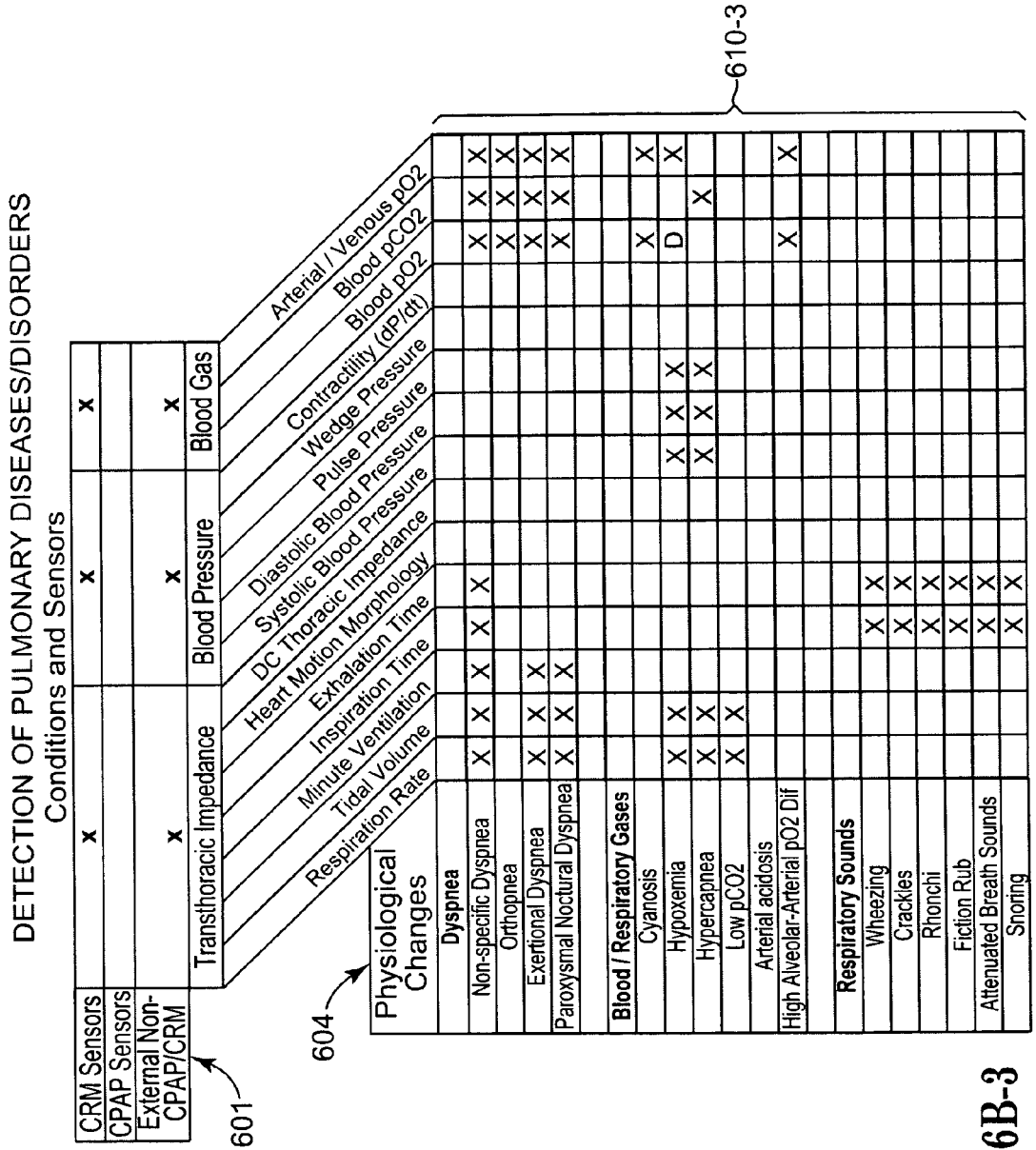
Figures 4, 6B:
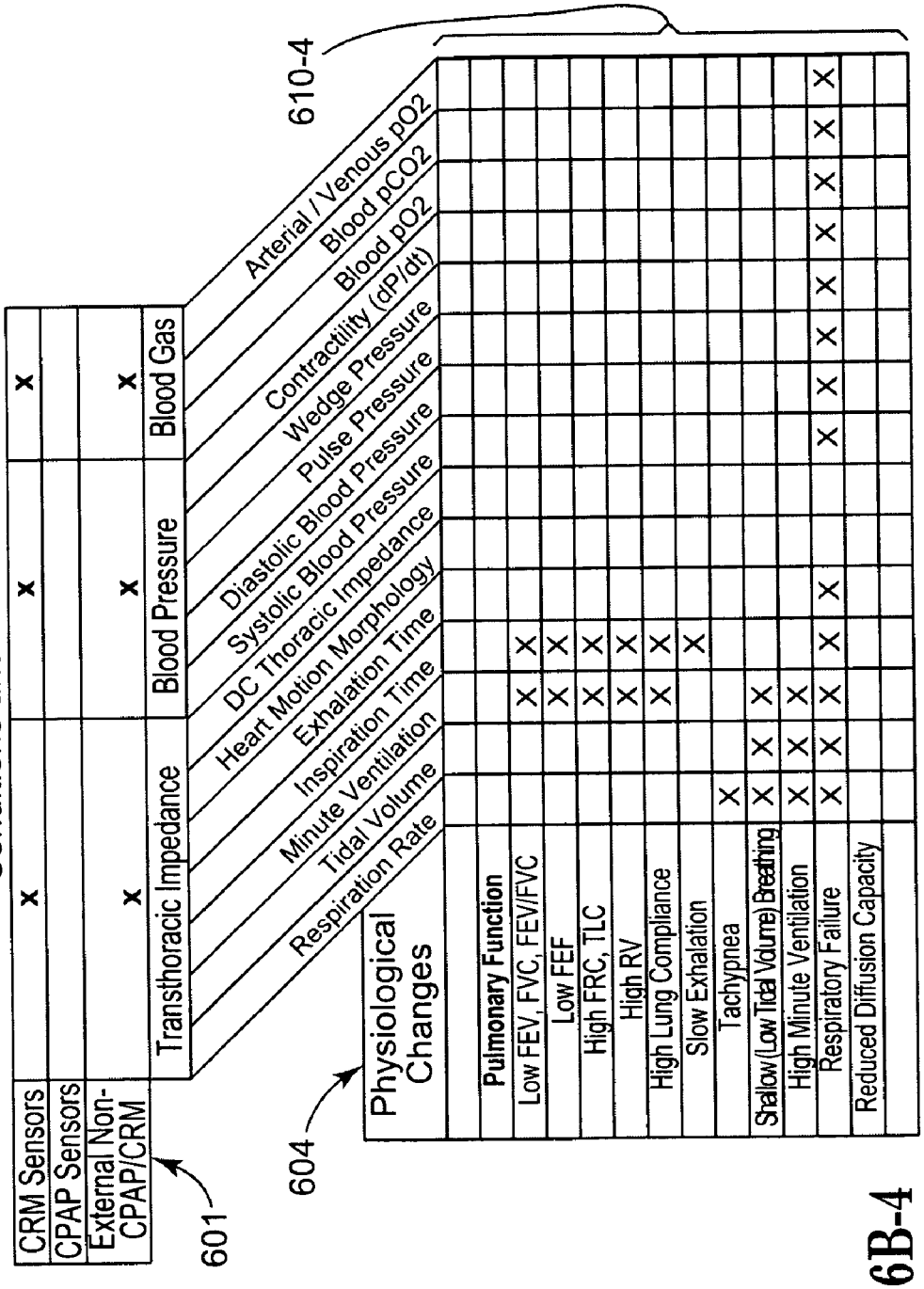
Figures 1, 6C:
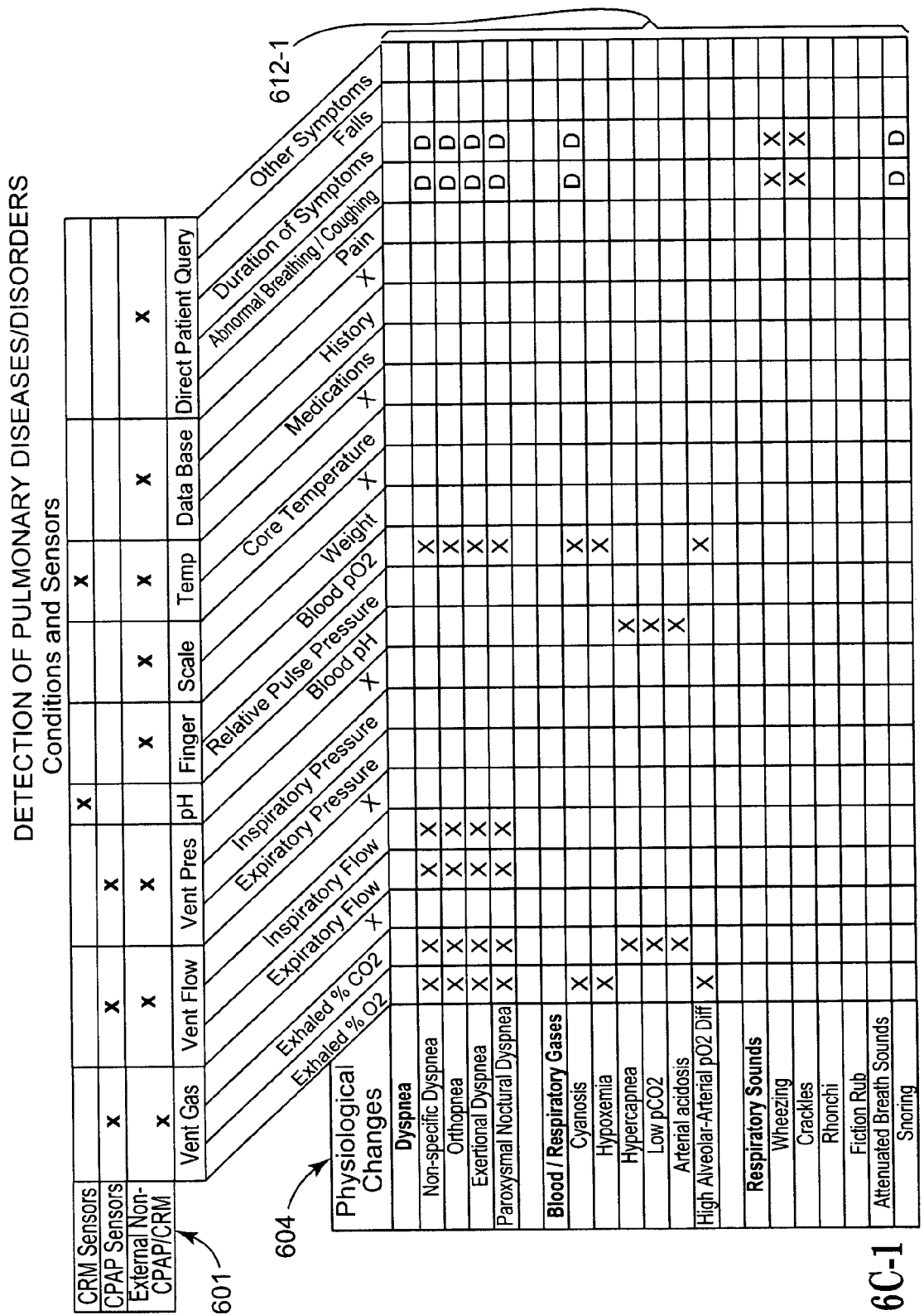
Figures 2, 6C:
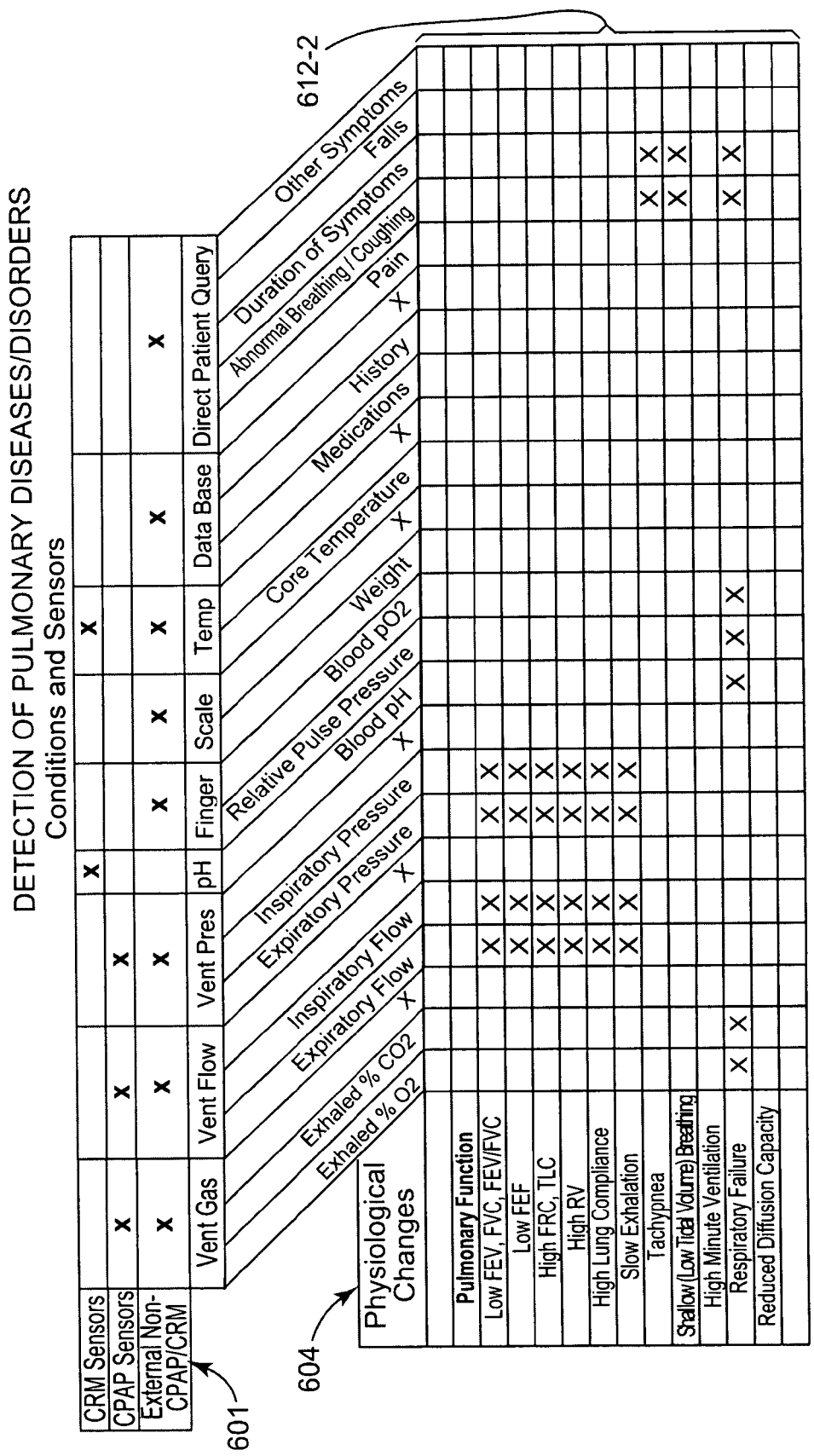
Figures 1, 6D:
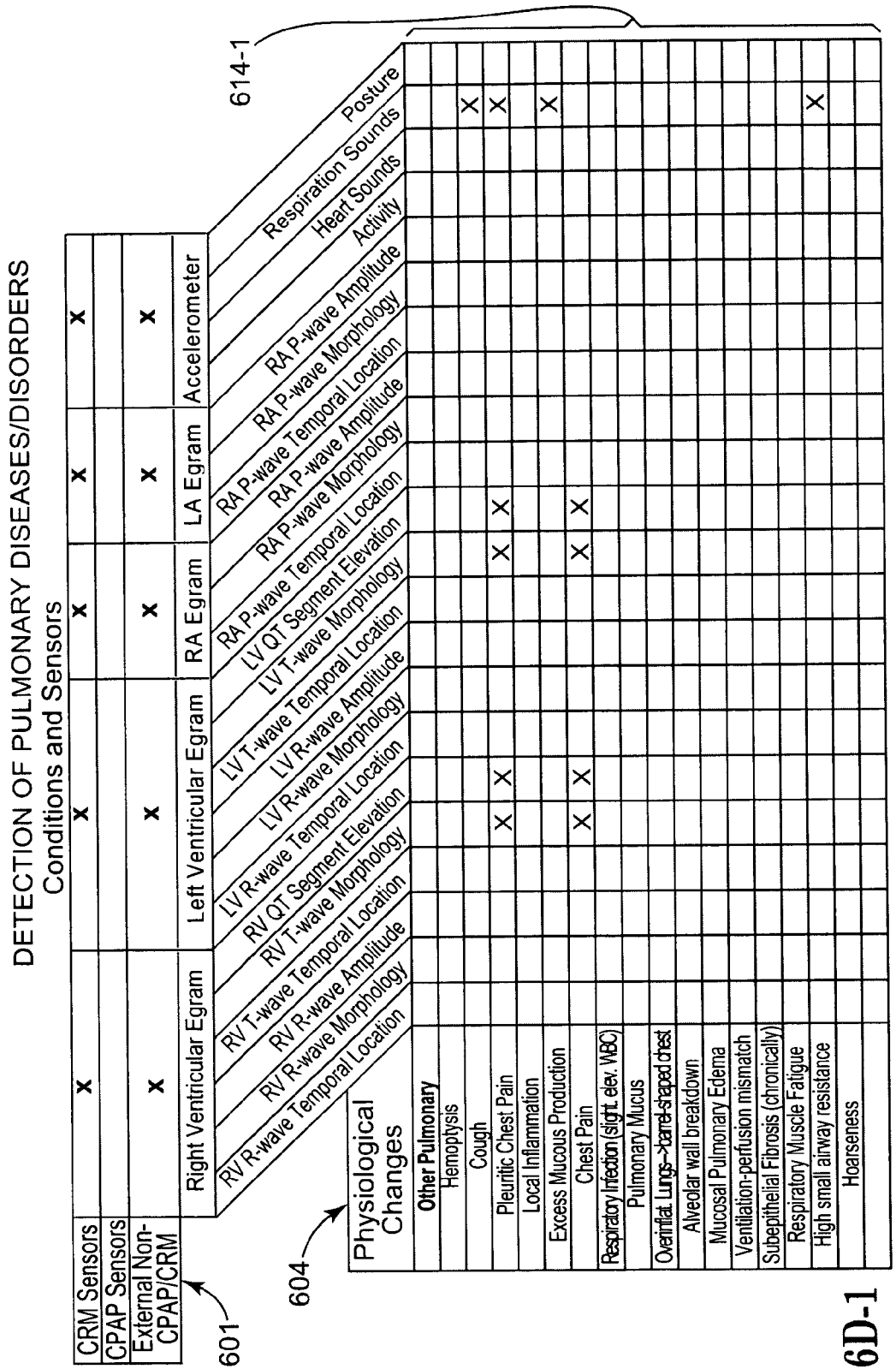
Figures 3, 6D:
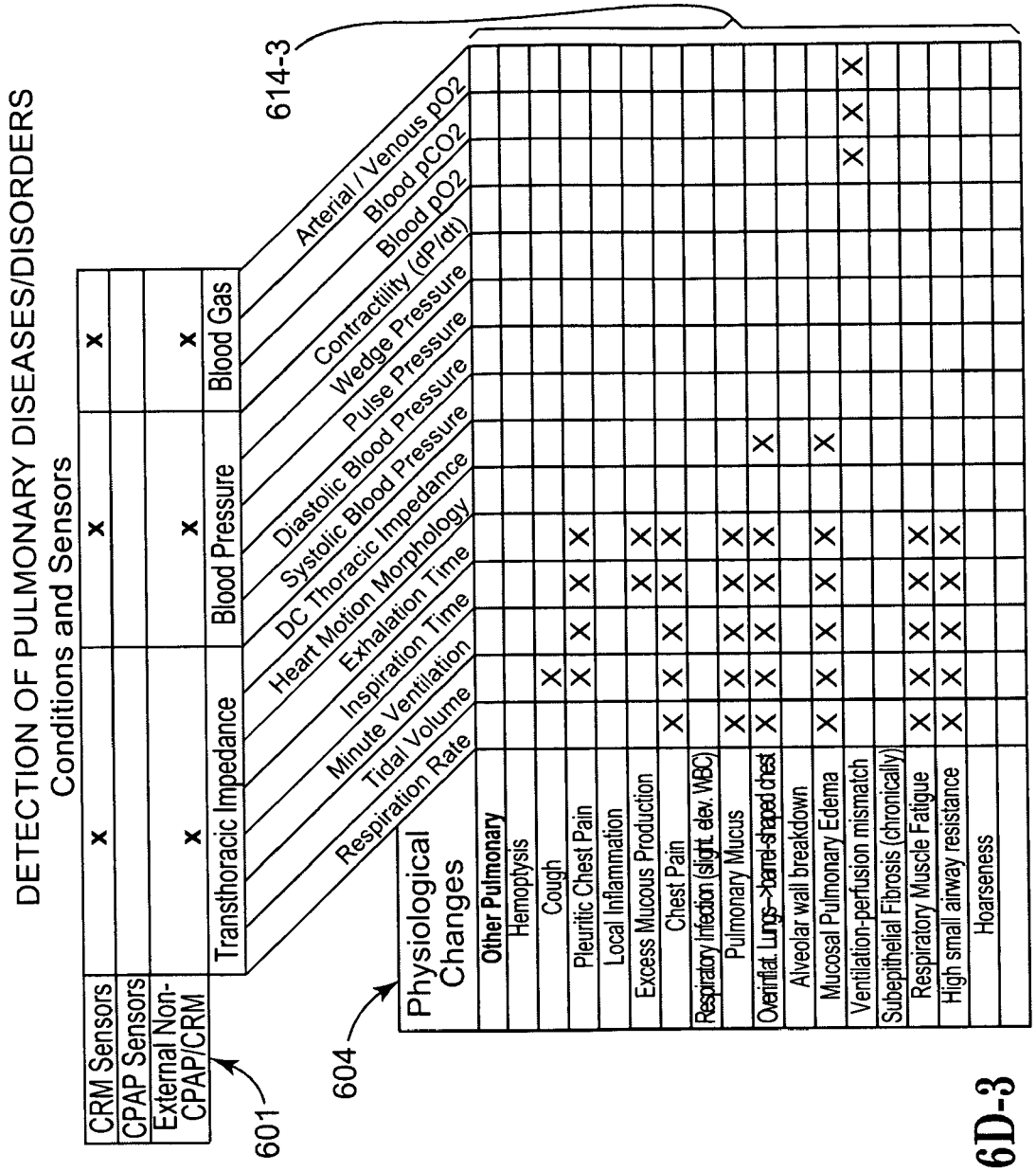
Figures 1, 6E:
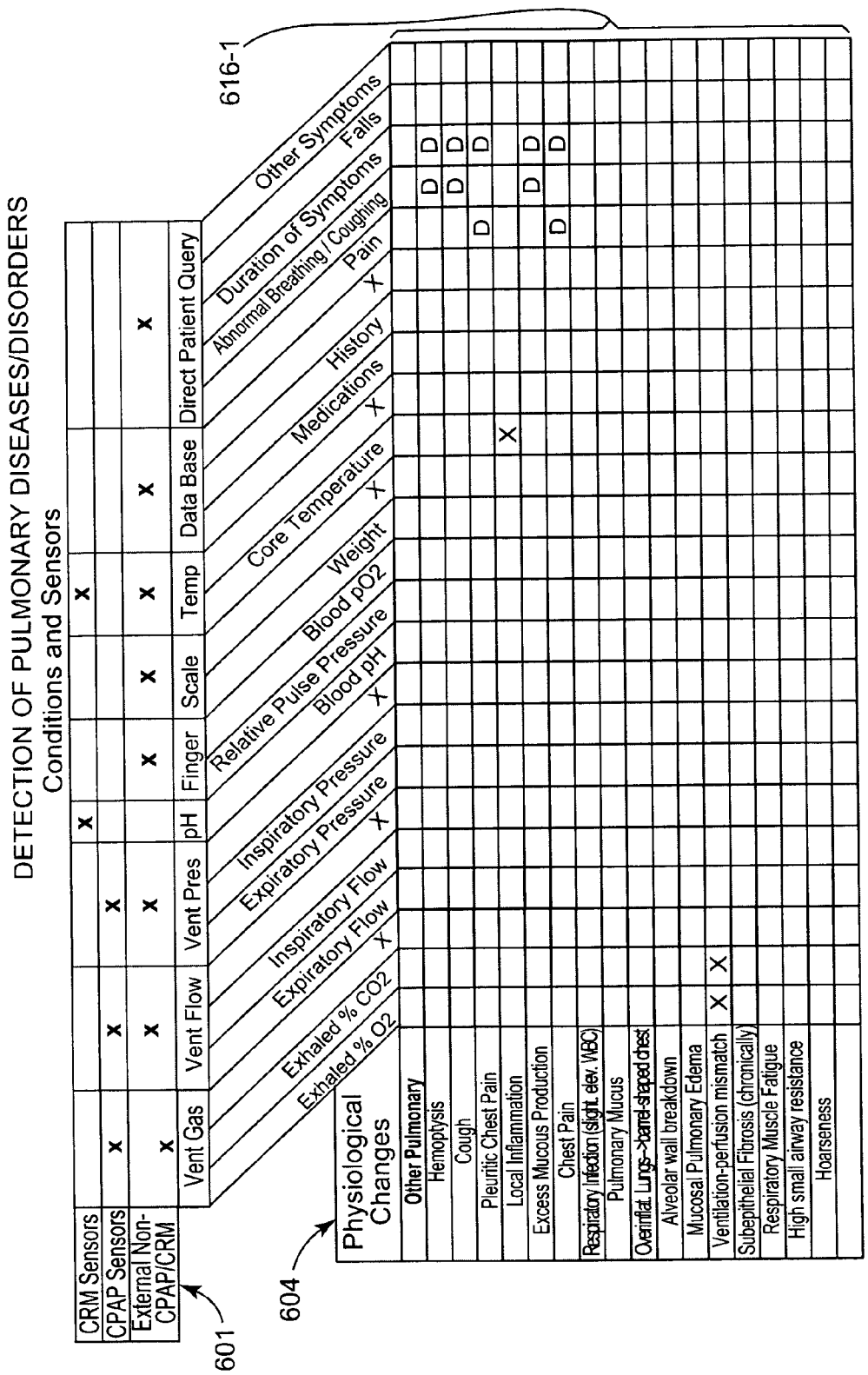

For legibility, the left and right sections 602, 603 of FIG. 6A are divided into sixteen portions, FIGS. 6B-1-6G-2. FIGS. 6B-1-6B-4 represent the upper left portion 610-1 to 610-4 of the left section 602 of FIG. 6A. FIGS. 6C-1-6C-2 represent the upper right portions 612-1 to 612-2 of the left section 602 of FIG. 6A. FIGS. 6D-1-6D-4 represent the lower left portions 614-1 to 614-4 of the left section 602 of FIG. 6A. FIGS. 6E-1-6E-2 represent the lower right portions 616-1 to 616-2 of the left section 602 of FIG. 6A. FIGS. 6F-1-6F-2 represent the upper portions 620-1 to 620-2 of the right section 604 of FIG. 6A. FIGS. 6G-1-6G-2 represent the lower portions 622-1 to 622-2 of the right section 604 of FIG. 6A. Relevant portions of the center section 604 and the top section 601 of FIG. 6A appear in each of the FIGS. 6B-1-6G-2 for convenience.

Figure 6H:
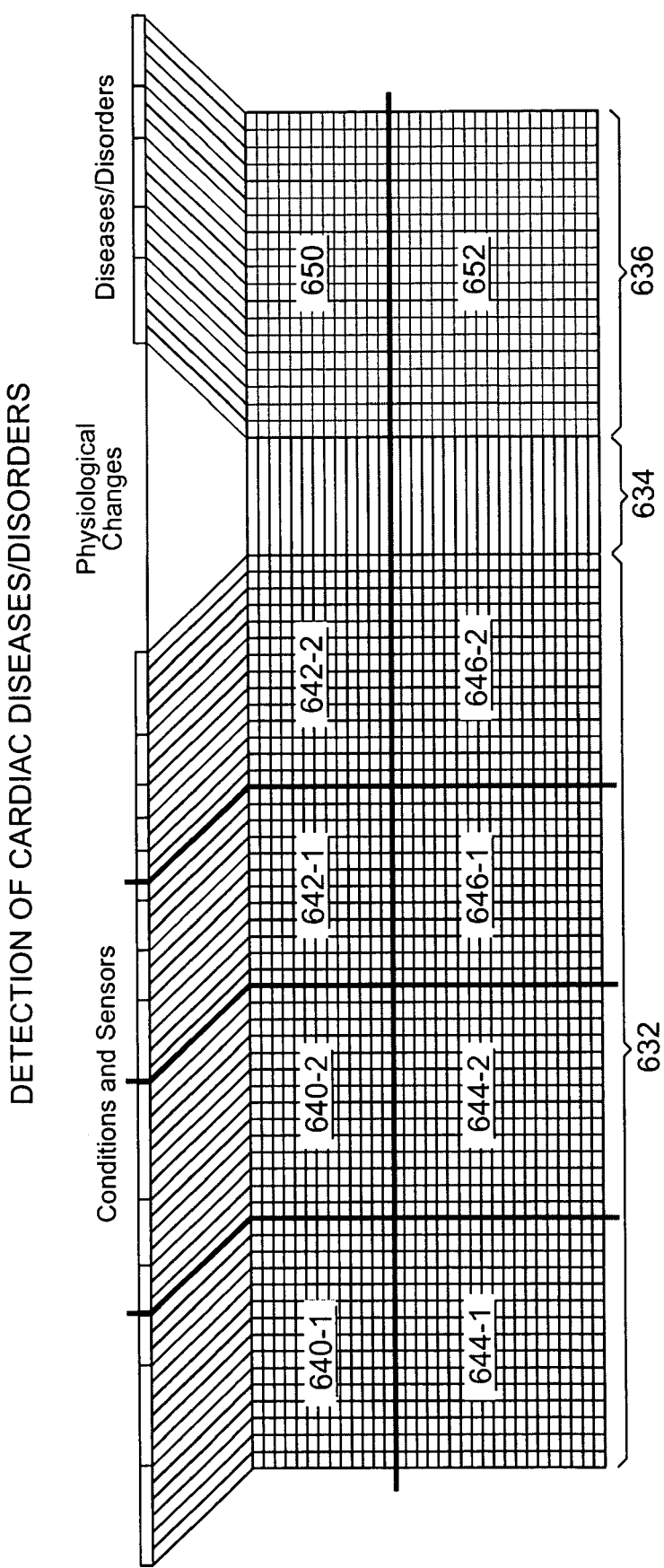
Figures 1, 6I:
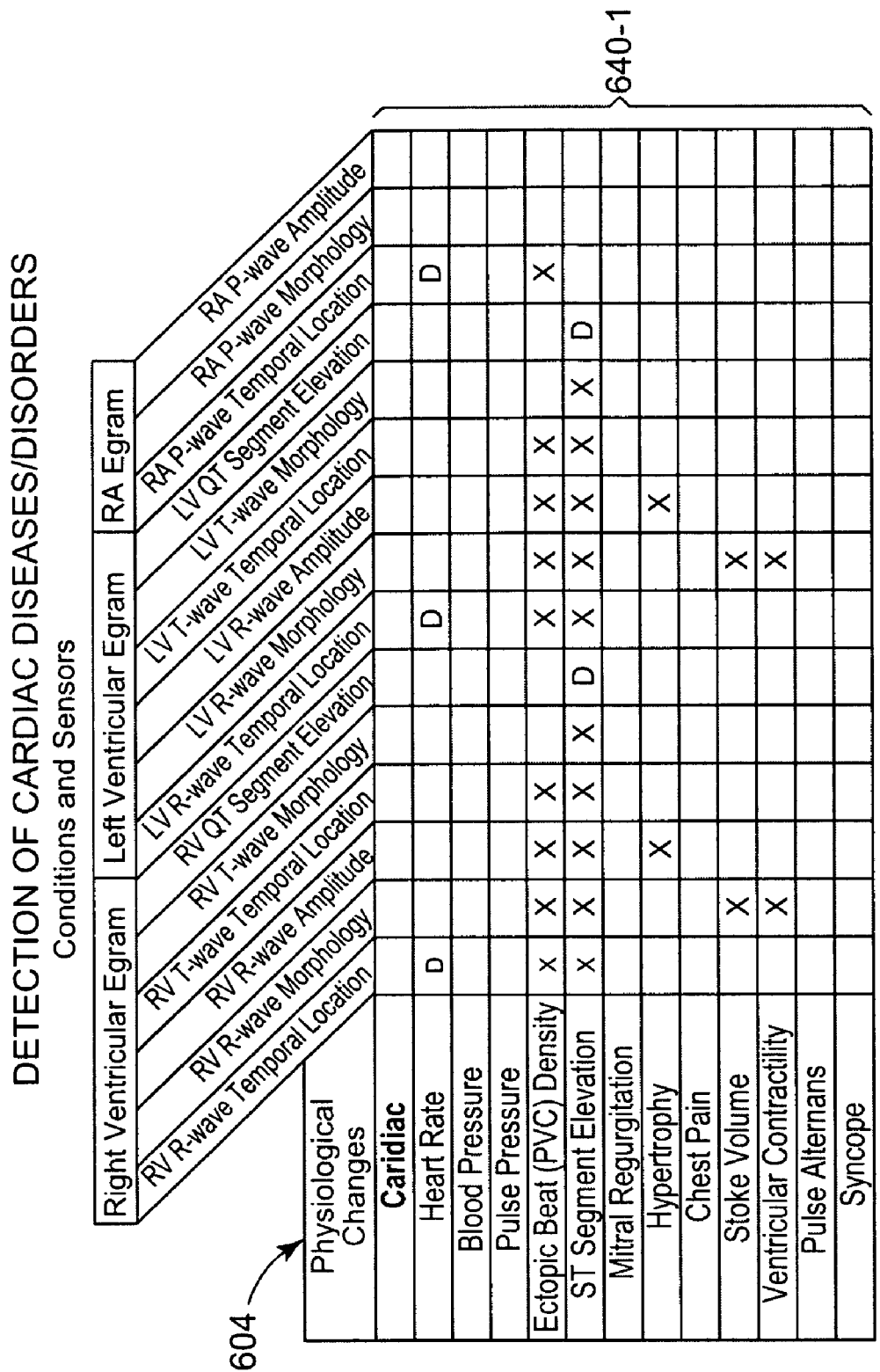
Figures 2, 6I:
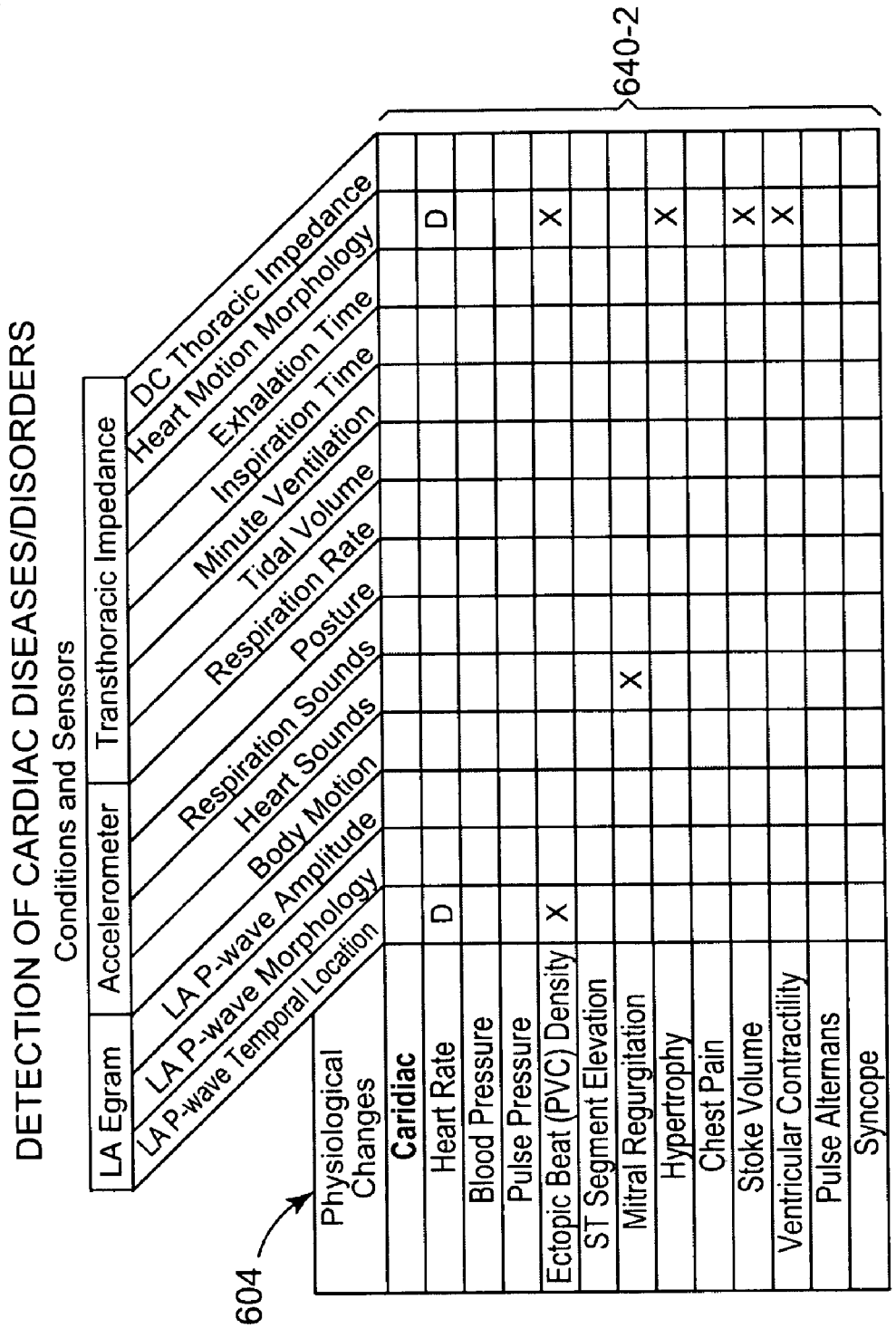
Figures 2, 6J:
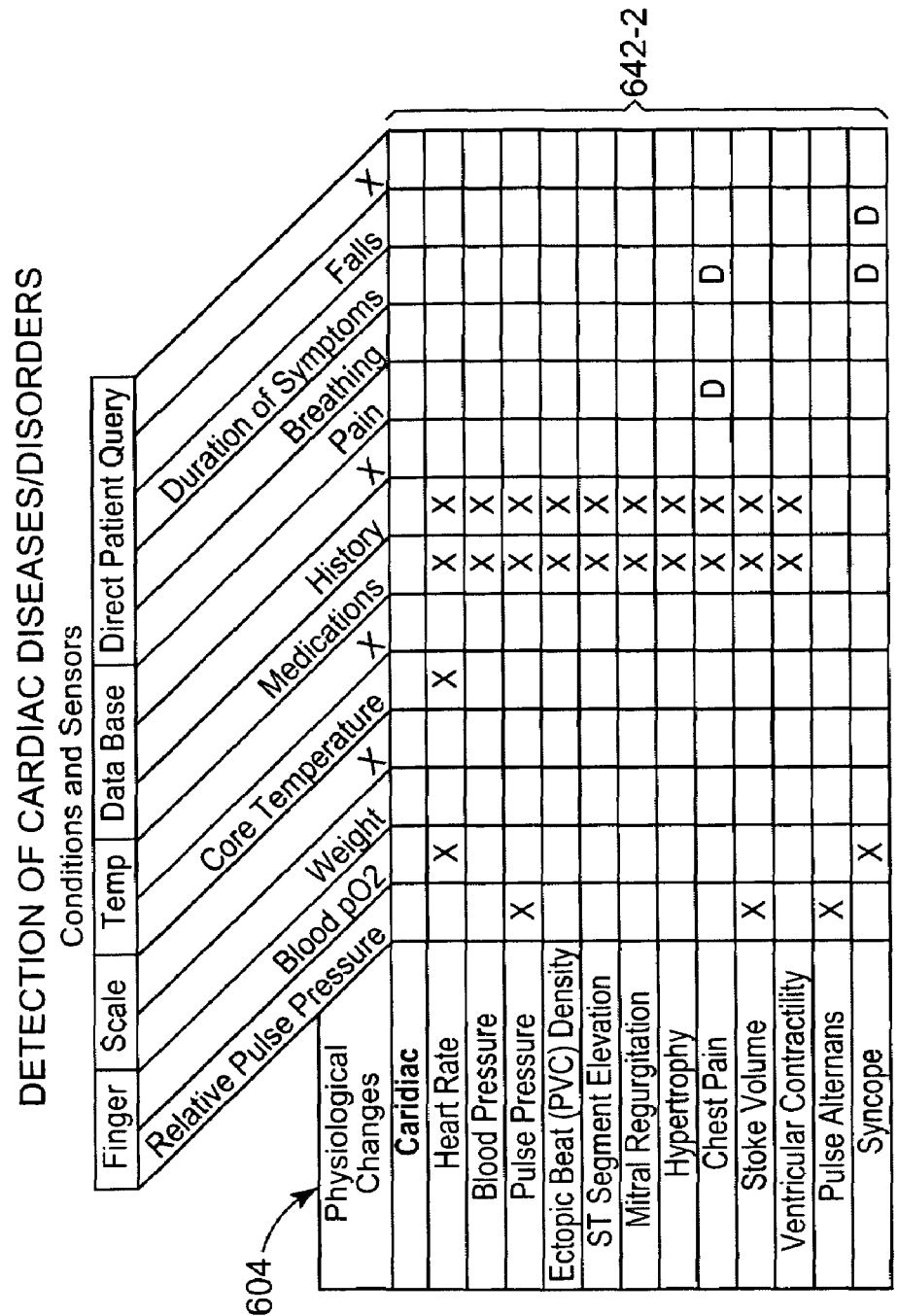
Figures 1, 6K:
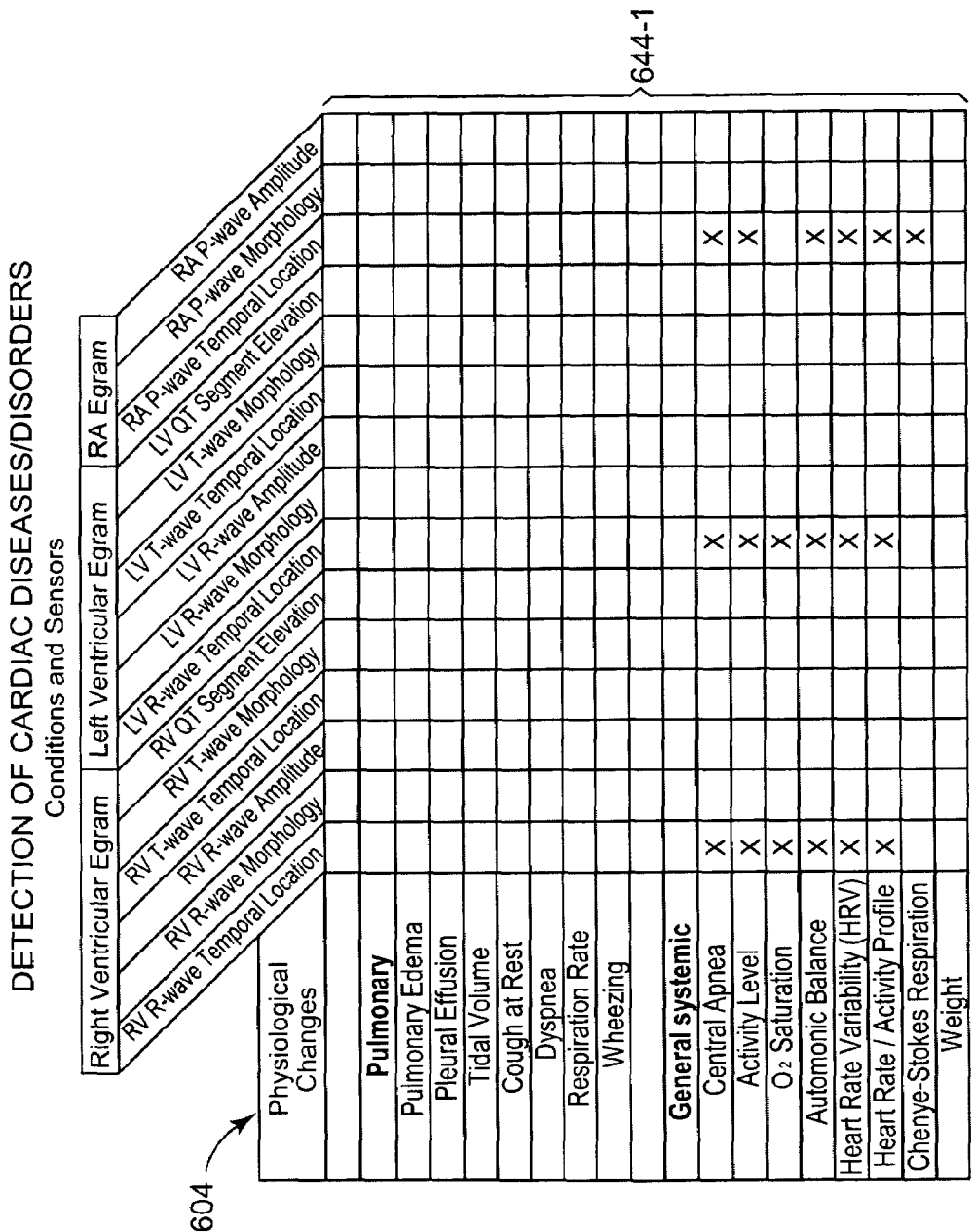
Figures 2, 6K:
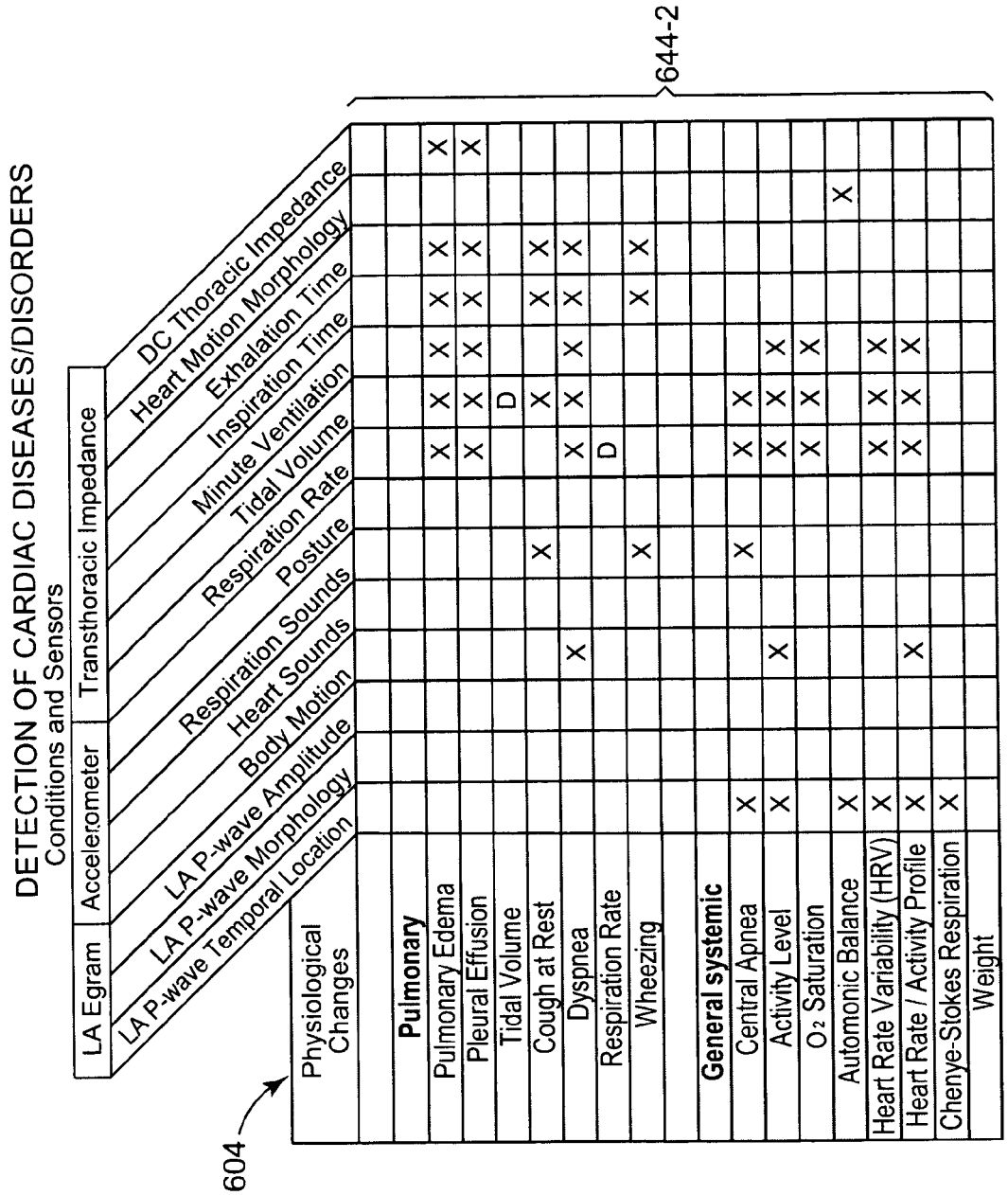
Figures 2, 6L:
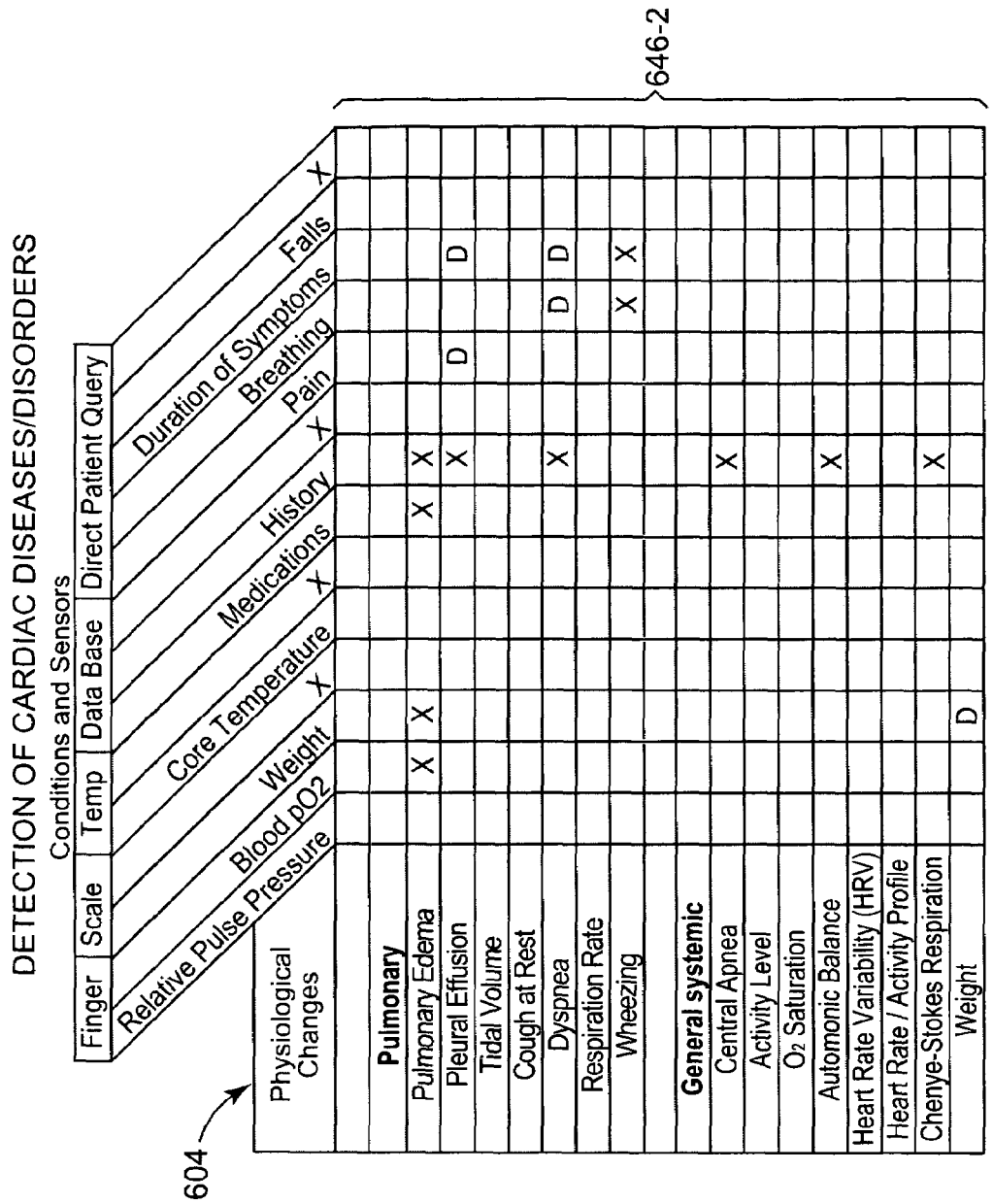
Figure 6N:
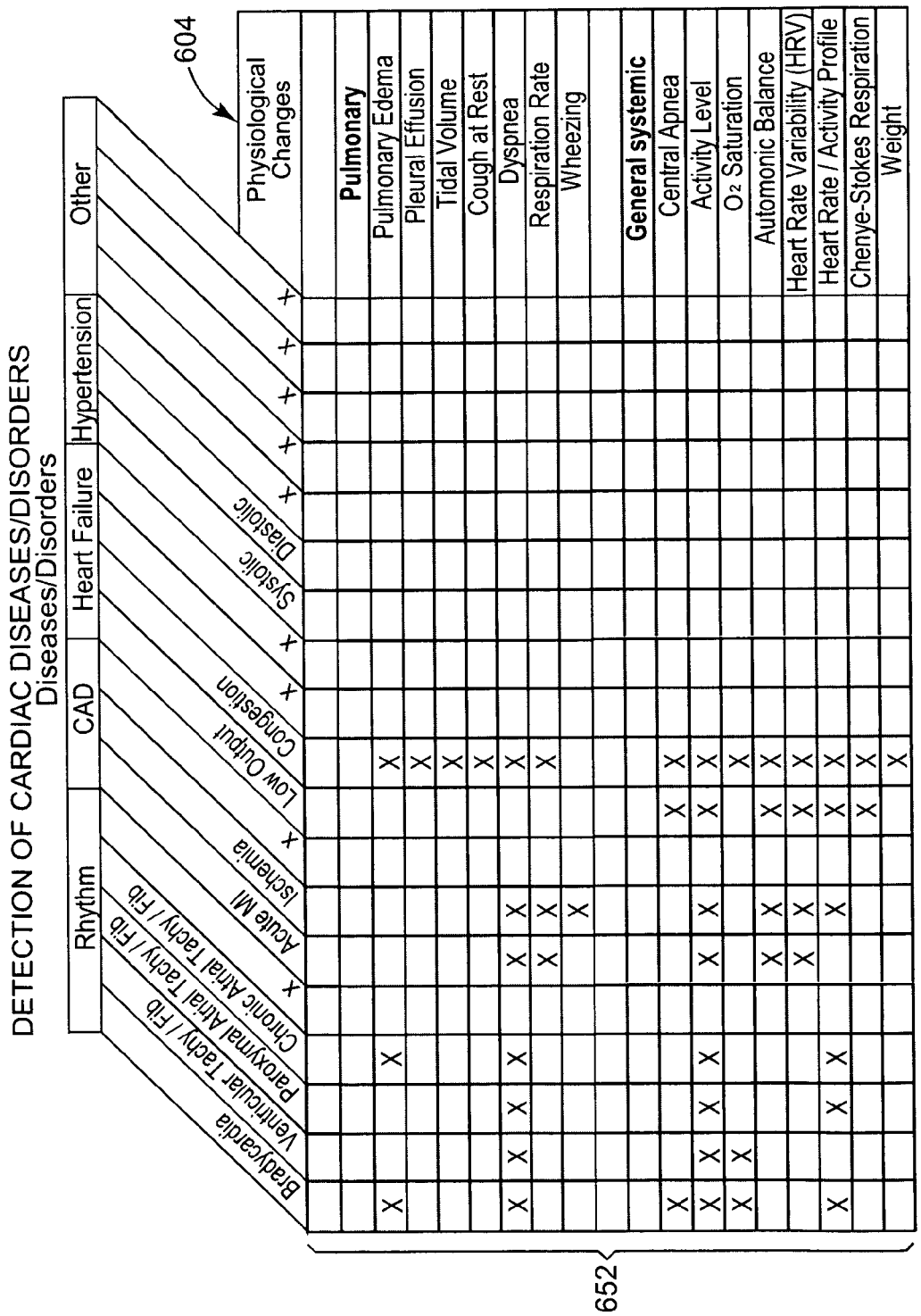

The chart provided in FIGS. 6H-6N illustrate conditions and sensors that may be used to determine physiological changes associated with various cardiac diseases and disorders. The left section 632 of FIG. 6H illustrates various conditions that may be sensed using sensors of a respiratory therapy device (CPAP), a cardiac device (CRM), or an external non-CPAP, non-CRM device. The center section 634 of FIG. 6H provides physiological changes and/or symptoms that may be evaluated using the conditions listed in the left section 632. The right section 636 of FIG. 6H lists cardiac diseases/disorders. The presence of the cardiac diseases/disorders of the right section 636 may be assessed based on the physiological changes and/or symptoms of the center section 634.

For legibility, the chart of FIG. 6H is divided into ten portions, FIGS. 6I-1-6N. FIGS. 6I-1-6I-2 represent the upper left portions 640-1 to 640-2 of the left section 632 of FIG. 6H. FIGS. 6J-1-6J-2 represent the upper right portions 642-1 to 642-2 of the left section 632 of FIG. 6H. FIGS. 6K-1-6K-2 represent the lower left portions 644-1 to 644-2 of the left section 632 of FIG. 6H. FIGS. 6L-1-6L-2 represent the lower right portions 646-1 to 646-2 of the left section 632 of FIG. 6H. FIG. 6M represents the upper portion 650 of the right section 636 of FIG. 6H. FIG. 6N represents the lower portion 652 of the right section 636 of FIG. 6H. Relevant portions of the center section 604 and the top section 601 of FIG. 6H appear in each of the FIGS. 6I-1-6N for convenience.

An example of how FIGS. 6A-6N may be used follows. Referring to FIGS. 6F-1 to 6G-2, the restrictive pulmonary disorder pneumoconiosis produces the physiological changes non-specific dyspnea (FIG. 6F-1) and cough (FIG. 6G-1). Non-specific dyspnea (FIG. 6F-1) and cough (FIG. 6G-1) are indicated by X or D marks in the column denoted pneumoconiosis in FIGS. 6F-1 and 6G-2, respectively. An "X" mark indicates that the symptom or physiological change may be derived from the sensed condition. A "D" mark indicates that the symptom or physiological change may be directly determined from the sensed condition. Non-specific dyspnea may be detected based on one or more of the conditions listed in the row for non-specific dyspnea illustrated in FIGS. 6B-1, 6B-3 and 6C-1. The conditions include duration of symptoms, abnormal breathing/coughing, blood pO2, inspiratory flow, expiratory flow, exhaled % CO2 and exhaled % O2, illustrated in FIG. 6C-1. The conditions also include arterial/venous pO2, blood pCO2, blood pO2, exhalation time, inspiration time, minute ventilation, tidal volume, respiration rate, FIG 6B-3, and/or respiration sounds 699 illustrated in FIG. 6B-1.

The presence of a disorder/disease, such as those listed in FIGS. 6A-6N, may be assessed by based on physiological changes and/or symptoms associated with the disorder/disease. The physiological changes and/or symptoms may be detected using conditions sensed by a sensor system of a respiratory therapy alone or in combination with the sensor systems of other therapeutic or diagnostic medical devices. If the sensed conditions indicate that the physiological changes or symptoms of a disease or disorder are consistent with a threshold level, the presence of the disease or disorder may be determined.

In another example, assessment of disease presence may be based on relative changes in one or more conditions indicative of physiological changes or symptoms caused by the disease. For example, assessment of a presence of a disease or disorder may be accomplished by evaluating the changes in conditions indicative of physiological changes or symptoms caused by the disease. The changes in the one or more conditions may be compared to threshold criteria. If changes in the conditions indicative of physiological changes or symptoms caused by the disease are consistent with threshold levels, a presence of the disease or disorder may be determined.

In a further example, the threshold criteria may involve relationships between the conditions indicative of physiological changes or symptoms caused by the disease. The presence of a disease may be assessed by evaluating relationships between conditions indicative of physiological changes or symptoms caused by the disease. For example, assessment of a disease may involve the determination that levels or amounts of two or more conditions have a certain relationship with one another. If relationships between the conditions indicative of physiological changes or symptoms caused by the disease are consistent with threshold relationship criteria, the disease or disorder may be present.

Techniques for assessing a presence of various pulmonary diseases, aspects of which may be incorporated into the embodiments described herein, are discussed in commonly owned U.S. patent application Ser. No. 10/930,508, entitled, "Methods and Systems for Assessing Pulmonary Disease," filed on Aug. 31, 2004 and incorporated herein by reference.

Figure 7:
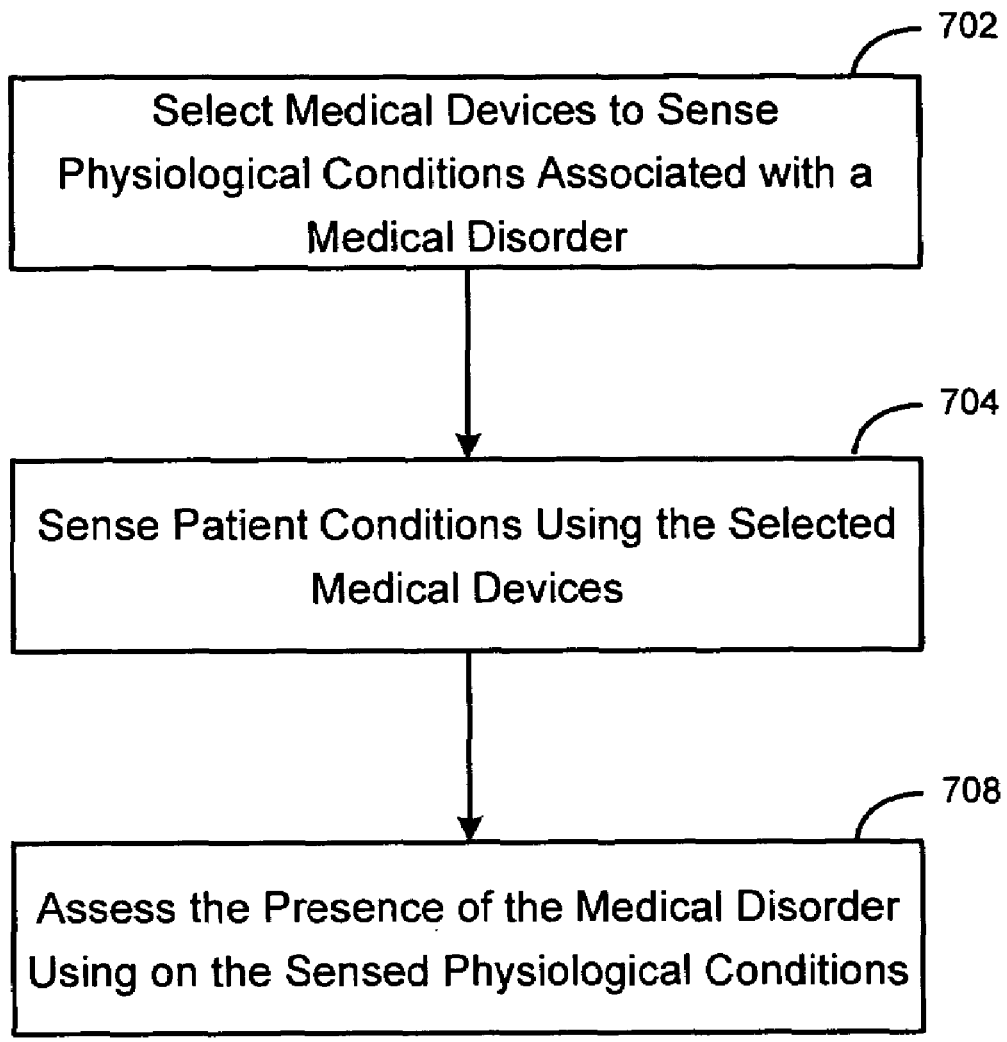
FIG. 7 is a flowchart of a method of detecting the presence of medical disorders in accordance with embodiments of the inventions.

FIG. 7 is a flowchart of a method of detecting the presence of medical disorders in accordance with embodiments of the inventions. The method involves selecting 702 one or more medical devices to sense one or more patient conditions associated with symptoms of the medical disorder. The medical devices selected may comprise for example, one or more implantable devices, one or more patient-external devices, or a combination of implantable and patient-external devices. The medical devices selected may comprise any number of therapeutic and/or diagnostic devices, including, for example, various therapeutic or diagnostic devices, including cardiac devices (pacemakers, cardioverter/defibrillators, cardiac resynchronizers, cardiac monitors), muscle stimulators, neurostimulators, implantable or patient-external drug delivery devices (drug pumps, electrically activate drug patches), patient-external respiratory devices (respiratory monitors, nebulizers, oxygen or gas therapy devices, ventilators, respirators, respiratory therapy devices providing positive and/or negative airway pressure), and the like.

The selection of the medical devices may be based, for example, on patient usage and/or on the proficiency or accuracy of the sensing system associated with a particular medical device. The one or more patient conditions are sensed 704 using the selected devices. Data may be collected based on the one or more sensed physiological conditions. The presence of a medical disorder is detected 708 based on the one or more sensed physiological conditions. Data pertaining to the sensed physiological conditions may be collected and stored, for example, continuously, or periodically, or according to some other time basis.

In some embodiments of the invention, portions of the data collection may be initiated upon detection of a medical event. For example, data collection may be initiated upon detection of an arousal event, a respiratory event, such as a sleep apnea event, and/or a cardiac event, such as a cardiac arrhythmia event.

In an embodiment of the invention, data collection may occur periodically, e.g., daily or hourly. In some implementations, the data collection may occur continuously or according to a random schedule. In some scenarios, it may be desirable to collect data only when the patient is asleep or only when the patient is awake. The system may detect sleep events to implement nocturnal and/or diurnal data collection, for example. The system may select one set of medical devices for sensing conditions during the day and alter the selection to include a second set of medical devices for sensing conditions at night.

In one example, a patient may have an implanted cardiac pacemaker and may also use, on a periodic basis, e.g., nightly, an external respiratory therapy device, such as a CPAP device. One or more conditions, including respiration may be sensed each night using the cardiac pacemaker and the CPAP device. The airflow sensor of the CPAP device may be automatically selected to sense patient respiration due to the higher accuracy of the airflow measurement in the CPAP device compared to the cardiac pacemaker. However, on some nights the patient may not use the CPAP device. If the patient does not use the CPAP device during a particular period, then patient respiration may be sensed using a surrogate measure, such as the transthoracic impedance sensor of the cardiac pacemaker. The cardiac pacemaker may be automatically selected as the medical device used for sensing patient respiration.

The medical devices used for sensing may be selected based on the proficiency of the sensing system associated with a particular medical device. For example, respiration sounds may be detectable using the accelerometer of a CRM or a patient-external microphone. If patient movements or other interference degrades respiration sound detection acquired by the CRM accelerometer, then the system may select the microphone as the preferred method of sensing respiration sounds.

In accordance with various embodiments of the invention, the presence of a medical disorder such as those listed in FIGS. 6A-6N, may be determined if symptoms of the medical disorder are present in sufficient degree. In one example, the presence of a medical disorder may be detected by comparing condition levels, e.g., blood pH level, heart rate, exhaled % O2, indicative of physiological symptoms caused by the medical disorder. The levels of the conditions are compared to threshold criteria. If the condition levels are consistent with threshold levels, the system may determine that the medical disorder is present. The threshold levels may be based on data previously acquired from the patient to establish baseline conditions. In another implementation, the threshold levels may be based on clinical data acquired from a group of subjects, for example.

Assessment of disease presence may be based on relative changes in one or more conditions indicative of physiological changes or symptoms caused by the disease. For example, detection of a presence of a medical disorder may be accomplished by evaluating the changes in one or more conditions indicative of physiological changes or symptoms caused by the disease. The changes in the one or more conditions may be compared to threshold criteria. If changes in the conditions indicative of physiological changes or symptoms caused by the disease are consistent with threshold levels, the non-rhythm pulmonary disease or disorder may be present. For example, if the levels of one or more conditions increase or decrease by a threshold amount of change, then a determination that the medical disorder is present may be made.

The threshold criteria may involve relationships between the conditions indicative of physiological changes or symptoms caused by the disease or disorder. The presence of a medical disorder may be assessed by evaluating relationships between conditions indicative of physiological changes or symptoms caused by the disease. For example, detection of the presence of a medical disorder may involve the determination that levels or amounts of two or more conditions have a certain relationship with one another. If relationships between the conditions indicative of physiological changes or symptoms caused by the disease are consistent with threshold relationship criteria, the system may determine that a particular medical disorder is present.

If the presence of a medical disease/disorder is determined, then the progression of the disease may be monitored. Monitoring the progression of the disease or disorder may involve, for example, collecting data and periodically evaluating one or more physiological changes or symptoms of the disease. Evaluating the one or more physiological changes or symptoms may be accomplished by comparing patient conditions to thresholds or other quantifiable indices. Monitoring the medical disorder may involve, for example, monitoring the progression and/or regression of the medical disorder, determining a severity of the disease, detecting disease onset and offset, and/or monitoring other aspects and/or events associated with the disorder.

As illustrated in FIGS. 6H-6N, cardiac disorders may be organized into disorders of cardiac rhythm, such as bradycardia, ventricular tachyarrhythmia, ventricular fibrillation, paroxymal atrial tachyarrhythia/fibrillation and chronic atrial tachyarrhythmia/fibrillation). Heart failure may cause contractions of the ventricles to become uncoordinated. Non-rhythm cardiac disorders include coronary artery disease (acute myocardial infarction, ischemia), and hypertension, which may be associated with systolic or diastolic types.

Pulmonary disorders may be organized into broad categories encompassing disorders of breathing rhythm and non-rhythm pulmonary diseases and/or disorders. Breathing rhythm disorders include various syndromes characterized by patterns of disordered breathing that produce insufficient respiration, for example, sleep apnea, hypopnea, and Cheyne-Stokes Respiration (CSR), among others. Breathing rhythm disorders are not necessarily accompanied by alteration of pulmonary structures.

Non-rhythm pulmonary diseases or disorders typically involve physical changes to lung structures, such as loss of elasticity of the lung tissue, obstruction of airways with mucus, limitation of the expansion of the chest wall during inhalation, fibrous tissue within the lung, excessive pressure in the pulmonary arteries, and/or other characteristics. Pulmonary diseases or disorders that are not rhythm-related are referred to herein as non-rhythm pulmonary diseases and may include obstructive pulmonary diseases, restrictive pulmonary diseases, infectious and non-infectious pulmonary diseases, pulmonary vasculature disorders, and pleural cavity disorders, for example.

According to one aspect of the invention, pulmonary function testing may be employed to detect physiological changes associated with the presence of cardiac and/or pulmonary disease. Pulmonary function tests may be used to evaluate lung mechanics, gas exchange, pulmonary blood flow, and blood gases and pH. They are used to evaluate patients in the diagnosis of pulmonary disease, assessment of disease development, or evaluation of the risk of pulmonary complications from surgery.

Pulmonary function testing is conventionally performed in a clinical setting and measures values indicative of the ability of the lungs to exchange oxygen and carbon dioxide. The total lung capacity (TLC) is divided into four volumes. The tidal volume ($V_T$) is the volume inhaled or exhaled in normal quiet breathing. The inspiratory reserve volume (IRV) is the maximum volume that can be inhaled following a normal quiet inhalation. The expiratory reserve volume (ERV) is the maximum volume that can be exhaled following a normal quiet exhalation. The residual volume (RV) is the volume remaining in the lungs following a maximal exhalation. The vital capacity (VC) is the maximum volume that can be exhaled following a maximal inhalation; VC=IRV+$V_T$+ERV. The inspiratory capacity (IC) is the maximum volume that can be inhaled following a normal quiet exhalation; IC=IRV+$V_T$. The functional residual capacity (FRC) is the volume remaining in the lungs following a normal quiet exhalation; FRC=ERV+RV.

The vital capacity and its components ($V_T$, IRV, ERV, IC) are typically measured using a spirometer, which is a device that measures the volumes of air inhaled and exhaled. The FRC is usually measured by the helium dilution method using a closed spirometry system. A known amount of helium is introduced into the system at the end of a normal quiet exhalation. When the helium equilibrates throughout the volume of the system, which is equal to the FRC plus the volume of the spirometer and tubing, the FRC is determined from the helium concentration. This test may underestimate the FRC of patients with emphysema. The FRC can be determined quickly and more accurately by body plethysmography. The residual volume and total lung capacity are determined from the FRC.

In the forced vital capacity (FVC) maneuver, the patient exhales as forcefully and rapidly as possible, beginning at maximal exhalation. Several parameters are determined from the spirogram. The FVC is the total volume of air exhaled during the maneuver; it is normally equal to the vital capacity. The forced expiratory volume (FEV) is the volume expired during a specified time period from the beginning of the test. The times used are 0.5, 1, 2, and 3 seconds; corresponding parameters are $FEV_{0.5}$, $FEV_{1.0}$, $FEV_{2.0}$, and $FEV_{3.0}$. The maximal expiratory flow rate (MEFR) is the slope of the line connecting the points where 200 ml and 1200 ml have been exhaled; it is also called $FEF_{200-1200}$ (forced expiratory flow). The maximal midexpiratory flow rate (MMFR, MMF) is the slope of the line connecting the points where 25 percent and 75 percent of the FVC have been exhaled; it is also called $FEF_{25-75}\%$.

The Maximal Voluntary Ventilation (MW) is the maximal volume of air that can be breathed by the patient, expressed in liters per minute; it was formerly called maximal breathing capacity (MBC). The patient breathes as rapidly and deeply as possible for 12 to 15 seconds and the volume exhaled is determined by spirometry.

Various parameters related to pulmonary performance, some of which may be measured using sensors of a respiratory therapy device include, for example, tidal volume, minute ventilation, inspiratory reserve volume, forced expiratory volume, residual volume, and forced vital capacity, among other parameters. According to one embodiment, testing of some pulmonary function parameters may be performed using the ventilation pressure and ventilation flow sensors of a CPAP device or other patient-external respiratory therapy device. The pulmonary function testing may be used, for example, to assess a presence of restrictive and/or obstructive pulmonary disorders as indicated in FIGS. 8A-8C.

Pulmonary performance may be evaluated based on data acquired by the respiratory therapy device during normal and forced inspiration and expiration. From such data, pulmonary parameters including tidal volume, minute ventilation, forced expiratory volume, forced vital capacity, among other parameters may be determined.

Because the results of pulmonary function tests vary with size and age, the normal values are calculated using prediction equations or nomograms, which give the normal value for a specific age, height, and sex. The prediction equations are derived using linear regression on the data from a population of normal subjects. The observed values are usually reported as a percentage of the predicted value. Abnormal test results may show either an obstructive or restrictive pattern. Sometimes, both patterns are present.

Figure 8:
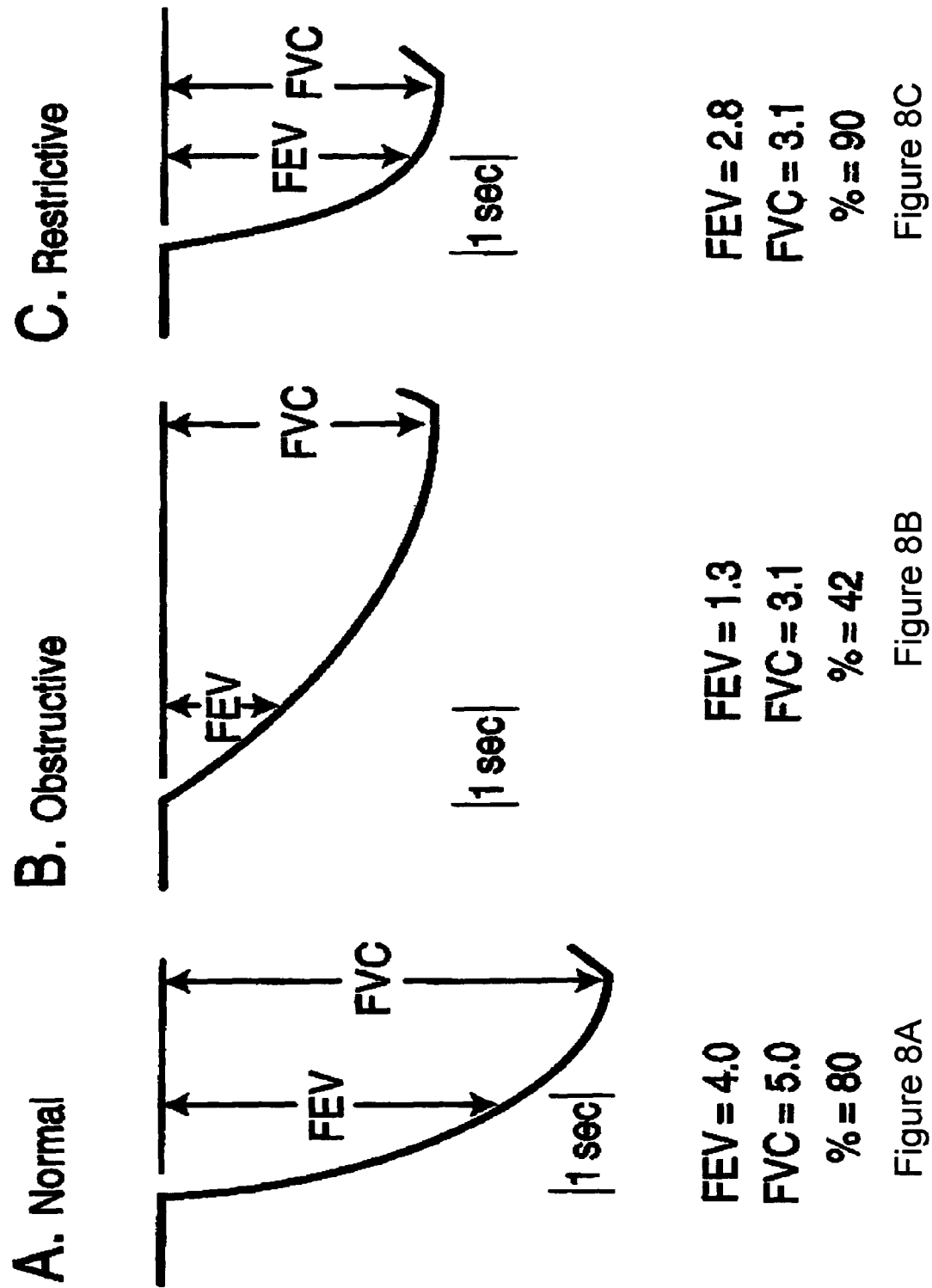
FIGS. 8A-8C illustrate normal, obstructive, and restrictive respiration patterns that may be utilized for medical disease/disorder detection and/or monitoring in connection with embodiments of the invention.

FIGS. 8A-8C are graphs of respiratory volume (y axis) with respect to time (x axis) during forced expiration. FIGS. 8A-8C illustrate normal, obstructive, and restrictive respiratory patterns, respectively. FIG. 8A illustrates a normal respiratory pattern, having normal $FEV_{1.0}$ and FVC. The volume expired at the beginning of a forced exhalation is generally large and the ratio of $FEV_{1.0}$ and FVC is normally about 80 percent. The total amount of time required for completing the forced exhalation is typically less than three seconds.

FIG. 8B illustrates an obstructive pattern. An obstructive pattern occurs when there is airway obstruction from any cause, as in asthma, bronchitis, emphysema, or advanced bronchiectasis; these conditions are grouped together in the nonspecific term chronic obstructive pulmonary disease (COPD). In this pattern, the residual volume is increased and the RV/TLC ratio is markedly increased. Owing to increased airway resistance, the flow rates are decreased. The $FEV_{1.0}$/FVC ratios, MMFR, and MEFR are all decreased; $FEV_{1.0}$/FVC may be less than 75 percent, for example, about 42 percent.

FIG. 8C illustrates a restrictive pattern. A restrictive pattern occurs when there is a loss of lung tissue or when lung expansion is limited as a result of decreased compliance of the lung or thorax or of muscular weakness. The conditions in which this pattern can occur include pectus excavatum, myasthenia gravis, diffuse idiopathic interstitial fibrosis, and space occupying lesions (tumors, effusions). In this pattern, the vital capacity and FVC are less than 80 percent of the predicted value, but the $FEV_{1.0}$/FVC ratios are normal. The TLC is decreased and the RV/TLC ratio is normal.

Embodiments of the invention utilize a patient-external respiratory therapy device to perform periodic pulmonary function testing. A CPAP or other external respiratory device may measure ventalitory pressure, ventilatory airflow, and/or ventalitory gas concentration during periodic, e.g., nightly, therapy sessions. The ventalitory pressure and/or airflow measurements may be used to measure FVC and FEV during forced expiration. From these two parameters, FEV/FVC can be derived to differentiate obstructive versus restrictive respiratory patterns as shown in the FIGS. 8B and 8C. Other measurements that are possible using the respiratory device sensors include low forced expiratory flow (FEF), high functional residual capacity (FRC), total lung capacity (TLC), and high residual volume (RV).

In one embodiment, the patient may perform forced expirations while connected to the external respiratory device. During the forced expirations, circuitry in the external respiratory device may collect measurements, including measurements useful in calculating the FEV and FVC measurements.

In addition, the forced expiratory flow ($FEF_{25-75}\%$) may be measured. The middle half by volume of the total expiration is marked, and its duration is measured. The $FEF_{25-75}\%$ is the volume in liters divided by the time in seconds. In patients with obstructive diseases, the $FEF_{25-75}\%$ is generally greater than their expected values.

Circuitry incorporated in the CPAP device may be used to compare measured FVC, FEV and $FEF_{25-75}\%$ values derived from the respiratory therapy device pressure sensors and/or airflow sensors with predicted values from normal subjects in accordance with various embodiments. The comparison provides diagnostic information of lung mechanics. Data acquired by the CPAP device may be transmitted, for example, from the respiratory therapy device to an advanced patient management (APM) system or other remote device.

The results of pulmonary function testing, along with other physiological conditions measured by the CPAP and/or other devices of the system, may be compared to initial or baseline results to detect changes and/or determine trends in the patient's cardiopulmonary status over time. The changes from baseline values may be used to discern a presence of disease processes.

According to one aspect, the system may compare sensed or measured physiological conditions to thresholds to assess the presence of a disease or disorder. In one scenario, the thresholds may be based on average, normal human data, such as may be collected in clinical studies. In another scenario, the thresholds may be based on patient specific data. Over time, a database of information about relevant conditions specific to the patient may be established. The information may be used to develop sets of criteria specific to the patient and associated with the presence of particular disease processes. Thus, in some implementations, the system may learn to recognize the presence of disease based on the history of symptoms and/or physiological changes that occur in a particular patient.

In some embodiments, pulmonary function testing may be performed using a cardiac rhythm management system (CRM) or other implantable device. In one implementation, the pulmonary function testing is performed using an implanted transthoracic impedance sensor. Transthoracic impedance sensing has been used in connection with rate-adaptive pacemakers to measure respiration cycles. An impedance sensor may be used to measure the variation in transthoracic impedance, which increases during the inspiratory and decreases during the expiratory phase of a respiration cycle. The sensor injects a sub-threshold stimulating current between the pacemaker case and an electrode on an intracardiac or subcutaneous lead, and measures the voltage across the case and another electrode on the same or another lead. Clinical investigations have shown that the impedance sensor can measure respiratory rate tidal volume, and minute ventilation accurately.

In accordance with various embodiments of the invention, pulmonary function testing may be implemented by a pacemaker or other implantable device. The pulmonary function testing may be performed using the transthoracic impedance sensor of the implantable device. Transthoracic impedance may be used to determine various respiration-related conditions, including respiration rate, respiration pattern, tidal volume, minute ventilation, among others. Transthoracic impedance may be used to measure FVC and FEV during forced expiration. From these two parameters, FEV/FVC can be derived to differentiate obstructive versus restrictive respiratory patterns as shown in the FIGS. 8B and 8C, respectively. In addition, the forced expiratory flow ($FEF_{25-75}\%$) may be measured by the implantable device.

The implantable device may be used to compare measured FVC, FEV and $FEF_{25-75}\%$ values derived from the implanted impedance sensor with predicted values from normal subjects in accordance with various embodiments. The comparison provides diagnostic information of lung mechanics.

Data acquired using the above-described techniques may be monitored, for example, monitored continuously, periodically, and/or controlled by specific events. The acquired data may be compared to initial or baseline data to assess physiological changes and/or symptoms over time. Various pulmonary performance trends may be monitored to detect physiological changes and/or changes that occur over time. The detected changes and/or symptoms may be used to assess a presence of a disease or disorder. Methods and systems for performing and/or analyzing pulmonary function tests, aspects of which may be utilized in connection with the present invention, are described in commonly owned U.S. patent application Ser. No. 10/885,145, filed Jul. 6, 2004, which is incorporated herein by reference.

Data acquired using the above-described techniques may be transmitted from the implantable device to an advanced patient management system or other remote device. Assessment of the patient's cardiopulmonary status or control of the therapy may be performed by the advanced patient management system.

In accordance with various embodiments of the invention, the presence of a medical disease or disorder, such as those listed in FIGS. 6A-6N, may be assessed by evaluating sensed conditions indicative of the a medical disease or disorder. Sensing the conditions may be accomplished using a synergistic process involving selection of one or more medical devices based on various parameters, including, for example, usage of the medical device, quality of the available sensed signals and/or other factors.

In one implementation, the presence of medical disease or disorder may be assessed by comparing levels or values associated with conditions indicative of physiological changes or symptoms caused by the medical disease/disorder to threshold criteria. If the condition levels or values are determined to be beyond threshold criteria levels, the system may determine that the non-rhythm pulmonary disease or disorder is present. The system may use the comparison of condition levels or values to threshold criteria to detect a presence of the medical disease/disorder, the progression of the medical disease/disorder, the regression of the medical disease/disorder and/or the offset of the medical disease/disorder, for example.

The system may initially determine the threshold criteria for one or more medical diseases or disorders by establishing baseline conditions for an individual patient. The baseline conditions may be established using data collected from the patient over a period of time. Clinical data acquired from a number of patients may alternatively or additionally used for establishing the threshold criteria.

In one implementation, assessment of disease presence may be based on relative changes in one or more conditions indicative of physiological changes or symptoms caused by the disease. In this implementation, the threshold criteria may involve a rate of change. For example, diagnosis of a medical disease or disorder may be accomplished by evaluating the rate of change in conditions indicative of physiological changes or symptoms caused by the disease. The changes in the one or more conditions may be compared to threshold criteria involving rate of change. If changes in the conditions indicative of physiological changes or symptoms caused by the disease are consistent with threshold criteria, then the medical disease or disorder may be present.

In a further example, the threshold criteria may involve relationships between the conditions indicative of physiological changes or symptoms caused by the medical disease/disorder. The presence of a medical disease or disorder may be assessed by evaluating relationships between conditions indicative of physiological changes or symptoms caused by the disease. For example, assessment of a medical disease or disorder may involve the determination that levels or amounts of two or more conditions have a certain relationship with one another. If relationships between the conditions indicative of physiological changes or symptoms caused by the disease are consistent with threshold relationship criteria, the medical disease or disorder may be present.

The system may establish a number of thresholds used for monitoring the progress of the disease. Following detection of the presence of the medical disease or disorder, the system may track the progression, regression and/or offset of the disease by comparing the sensed conditions to the established thresholds.

Figure 9:
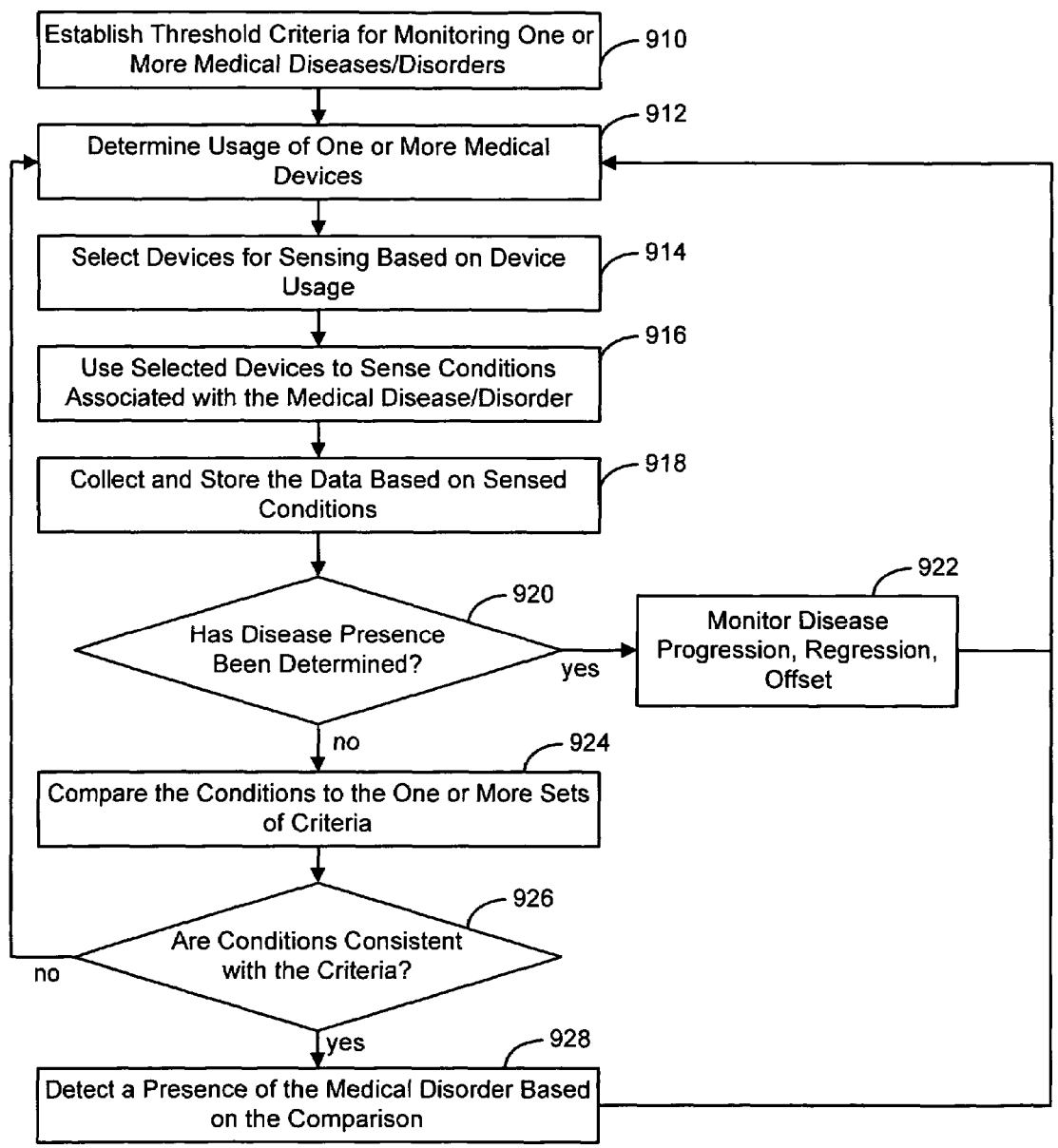
FIG. 9 is a flowchart illustrating a method of assessing a presence of a medical disease in accordance with embodiments of the invention.

FIG. 9 is a flowchart illustrating a method of assessing a presence of a medical disease in accordance with embodiments of the invention. Criteria sets for assessment of the non-rhythm pulmonary diseases are established 910. The usage of one or more medical devices is determined 912. Usage of a medical device may be implemented, for example, by determining a proximity of the patient to the medical device.

In one implementation, the proximity of the patient to an external breathing therapy device may be determined using a transmitter coupled to the external breathing therapy device and a receiver in the selection processor. If the patient is near the external breathing therapy device, the receiver receives a signal broadcast by the transmitter. The transmitter may be located on a bedside unit of the external breathing therapy device, or on the respiratory mask of the external breathing therapy device, for example.

Further, usage of an external device may be implemented in other ways, involving, for example, notification by the patient that the external device is in use, or by examining one or more sensed signals to determine if the sensed signals correspond to nominal signal values when the medical device is in use by the patient.

One or more medical devices are selected 914 to sense one or more conditions associated with a medical disorder. The selected medical devices are used to sense 916 the one or more conditions. The system may select the medical devices based on at least one of a sensing parameter of the medical devices. For example, the system may select the medical devices based on sensing characteristics including the type, quality, reliability, repeatability, efficiency, availability, accuracy, resolution, dynamic range, specificity, sensitivity or predictive value of the sensing or measurement provided by the medical device. In one implementation, a medical device may be selected based on patient usage. For example, if first and second medical devices are available to sense patient conditions, the first medical device may be selected to sense a first condition and a second medical device may be selected to sense a second condition. However, if only the first medical device is in use, then both conditions may be sensed using the first medical device.

In another implementation, medical device selection may depend on the sleep/wake cycle of the patient. A first medical device may be selected to monitor a physiological condition while the patient is awake, and a second medical device may be selected to monitor the physiological condition while the patient is asleep.

Data is collected 918 based on the sensed information. In some implementations, data collection may be initiated based on the detection of a triggering event. For example, data collection may be initiated and/or terminated based on the detection of a respiratory system event, a cardiac event, a sleep event, and/or other types of events. Methods and systems for event-based collection of medical information, aspects of which may be incorporated in medical disease detection processes of the present invention, are described in commonly owned U.S. patent applications Ser. No. 10/920,568, entitled "Medical Event Logbook System and Method," filed Aug. 17, 2004, and U.S. application Ser. No. 10/920,569, entitled "Sleep Logbook," filed Aug. 17, 2004, both of which are incorporated herein by reference.

If a presence of the medical disorder was previously determined 920, marking an onset of the medical disorder, then the progression, regression, and/or offset of the medical disorder is monitored 922.

If the presence of the disease was not previously determined 922, then the levels of the sensed conditions are compared 924 to a set of criteria associated with the disease. If levels of the conditions are consistent 926 with the threshold levels, then a presence of the medical disorder is detected 928.

The system may continue to collect data based on the sensed conditions to monitor the progression, regression and/or offset of the medical disorder. The system may modify the selection of the medical devices used to sense patient conditions before the disorder presence is detected and/or during the time that the system monitors the disorder. For example, the system may check nightly to determine the usage of a CPAP device. If the CPAP device is in use on a particular night, the CPAP device may be used to sense conditions associated with the medical disorder. However, on a different night, the patient may not use the CPAP. In this situation, the system may automatically shift the sensing function previously performed by the CPAP to another medical device.

A number of the examples presented herein involve block diagrams illustrating functional blocks used for monitoring functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention.

The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

What is claimed is:

1. An automated method for detecting a presence of a medical disorder, comprising:

detecting availability of one or more medical devices of a plurality of medical devices, each medical device configured for sensing one or more parameters indicative of a physiological condition, the plurality of medical devices comprising an implanted device and a patient external medical device;

assessing proficiency in sensing the one or more parameters indicative of the physiological condition of each of the one or more medical devices detected to be available;

selecting one of the plurality of medical devices to sense data indicative of the physiological condition associated with the medical disorder, the selection based on the proficiency assessment;

sensing data associated with the physiological condition using the selected medical device; and assessing the presence of the medical disorder based on the sensed data associated with the physiological condition.

2. The method of claim 1, wherein each of the plurality of medical devices is configured to sense a common parameter indicative of the physiological condition and the proficiency assessment comprises comparing quality of data of the common parameter sensed by each of the plurality of medical devices.

3. The method of claim 1, wherein the medical disorder comprises disordered breathing and each device of the plurality of medical devices is configured to deliver a disordered breathing therapy.

4. The method of claim 1, wherein detecting availability of the one or more medical devices comprises detecting proximity of the patient external medical device to the implanted medical device.

5. The method of claim 1, wherein the implanted device is configured to sense a first parameter indicative of the physiological condition and the patient external medical device is configured to sense a second parameter indicative of the physiological condition, wherein the first parameter is different from the second parameter, and wherein the proficiency assessment comprises comparing proficiency of each of the plurality of medical devices in assessing the physiological condition using the first and second parameters.

6. The method of claim 1, wherein selecting the medical device comprises selecting the medical device of the plurality of medical devices that is least affected by noise in sensing the one or more parameters based on the proficiency assessment.

7. The method of claim 1, further comprising selecting the implanted device of the plurality of medical devices or another implanted device based on the proficiency assessment, the implanted device selected to sense a second parameter indicative of the physiological condition, wherein based on the proficiency assessment the patient external medical device is selected to sense a first parameter indicative of the physiological condition.

8. The method of claim 1, further comprising delivering therapy to treat the detected medical disorder using one or both of the implanted device and the patient external medical device.

9. The method of claim 1, wherein assessing proficiency further comprises assessing relative quality, reliability, repeatability, efficiency, accuracy, sensitivity, specificity, or resolution of each of the medical devices in sensing the one or more parameters indicative of the physiological condition.

10. A system for assessing a disease presence, comprising:
a plurality of medical devices including an implantable medical device and a patient external medical device, each medical device comprising a sensing system configured to sense one or more parameters indicative of a physiological condition;
a selection processor coupled to the plurality of medical devices, the selection processor configured to execute program instructions stored in memory to cause the system to detect availability of at least one of the plurality of medical devices, assess proficiency of each of the medical devices detected to be available in sensing the one or more parameters indicative of the physiological condition, and select one of the medical devices to sense the one or more parameters indicative of the physiological condition based on the proficiency assessment; and
a diagnosis processor coupled to the sensing system of each of the plurality of medical devices, the diagnosis processor configured to execute stored program instructions to assess a presence of a medical disorder based on the physiological condition.

11. The system of claim 10, wherein each of the plurality of medical devices is configured to sense a common parameter indicative of the physiological condition and the selection processor is configured to execute stored program instructions to compare proficiency of each of the plurality of medical devices in sensing the common parameter as part of the proficiency assessment.

12. The system of claim 10, wherein the selection processor is further configured to execute stored program instructions to alter the selection of the one or more medical devices based on a subsequent proficiency assessment of the one or more medical devices in sensing the one or more parameters indicative of the physiological condition.

13. The system of claim 10, wherein the selection processor is further configured to execute stored program instructions to assess relative quality, reliability, repeatability, efficiency, accuracy, sensitivity, specificity, or resolution of each of the medical devices in sensing the one or more parameters indicative of the physiological condition as part of the proficiency assessment.

14. The system of claim 10, wherein the implantable medical device is configured to deliver an electrical cardiac therapy, the external medical device is configured to deliver a respiratory therapy, and the physiological condition is associated with respiration.

15. The system of claim 10, further comprising a therapy unit configured to deliver patient therapy to treat the detected medical disorder based on the assessed presence of the medical disorder.

16. The system of claim 15, wherein the therapy unit comprises the implantable medical device and the implantable medical device is configured to deliver a cardiac electrical therapy based on the assessed presence of the medical disorder.

17. The system of claim 15, wherein the therapy unit comprises the patient external medical device and the patient external medical device is configured to deliver an external respiratory therapy based on the assessed presence of the medical disorder.

18. A system for detecting a presence of a medical disorder, comprising:
means for detecting availability of a plurality of medical devices, each medical device configured for sensing one or more parameters indicative of a physiological condition associated with a medical disorder and delivering a therapy to address the medical disorder, the plurality of medical devices comprising an implantable device and a patient external medical device;
means for assessing proficiency of each of the medical devices in sensing the one or more parameters indicative of the physiological condition;
means for selecting one of the medical devices to sense data associated with the physiological condition associated with the medical disorder based on the proficiency assessment;
means for sensing the one or more physiological conditions using the selected medical device; and
means for detecting the presence of the medical disorder based on the sensed physiological condition.

19. The system of claim 18, wherein the medical condition comprises disordered breathing, each device of the plurality of medical devices is configured to deliver disordered breathing therapy, and the proficiency assessment comprises comparing quality of data sensed by the implantable device and the patient external medical device.

20. The system of claim 18, further comprising:
means for collecting data based on the physiological condition using the selected medical device;
means for trending the collected data; and
means for assessing the medical disorder based on a data trend.

* * * * *

UNITED STATES PATENT AND TRADEMARK OFFICE
CERTIFICATE OF CORRECTION

PATENT NO.      : 7,610,094 B2
APPLICATION NO. : 10/939586
DATED           : October 27, 2009
INVENTOR(S)     : Stahmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1157 days.

Signed and Sealed this

Twelfth Day of October, 2010

David J. Kappos
*Director of the United States Patent and Trademark Office*